US011180780B2

(12) United States Patent
Burgard et al.

(10) Patent No.: US 11,180,780 B2
(45) Date of Patent: Nov. 23, 2021

(54) ORGANISMS FOR THE PRODUCTION OF 1,3-BUTANEDIOL

(71) Applicant: Genomatica, Inc., San Diego, CA (US)

(72) Inventors: Anthony P. Burgard, Bellefonte, PA (US); Mark J. Burk, San Diego, CA (US); Robin E. Osterhout, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 15/616,841

(22) Filed: Jun. 7, 2017

(65) Prior Publication Data

US 2017/0275654 A1    Sep. 28, 2017

Related U.S. Application Data

(63) Continuation of application No. 14/673,600, filed on Mar. 30, 2015, now Pat. No. 9,708,632, which is a continuation of application No. 12/772,114, filed on Apr. 30, 2010, now Pat. No. 9,017,983.

(60) Provisional application No. 61/174,473, filed on Apr. 30, 2009.

(51) Int. Cl.
| | | |
|---|---|---|
| *C12N 9/88* | (2006.01) | |
| *C12N 9/90* | (2006.01) | |
| *C12P 7/16* | (2006.01) | |
| *C12N 15/00* | (2006.01) | |
| *C12P 7/18* | (2006.01) | |
| *C12N 15/52* | (2006.01) | |
| *C12N 9/04* | (2006.01) | |
| *C07C 29/80* | (2006.01) | |
| *C12N 9/02* | (2006.01) | |
| *C12N 9/10* | (2006.01) | |

(52) U.S. Cl.
CPC ............... *C12P 7/18* (2013.01); *C07C 29/80* (2013.01); *C12N 9/0006* (2013.01); *C12N 9/0008* (2013.01); *C12N 9/1029* (2013.01); *C12N 9/1096* (2013.01); *C12N 9/88* (2013.01); *C12N 15/52* (2013.01); *C12Y 101/01157* (2013.01); *C12Y 101/01* (2013.01); *C12Y 102/01* (2013.01); *C12Y 203/01* (2013.01); *C12Y 206/01* (2013.01); *C12Y 401/01* (2013.01); *C12Y 402/01* (2013.01); *C12Y 403/01* (2013.01)

(58) Field of Classification Search
CPC .. C12P 7/18; C12N 15/52; C12N 9/88; C12N 9/0006; C12Y 101/01157; C12Y 401/01; C12Y 203/01
USPC ........ 435/158, 252.2, 252.32, 252.33, 320.1, 435/157
See application file for complete search history.

(56) References Cited

U.S. PATENT DOCUMENTS

| | | |
|---|---|---|
| 5,512,669 A | 4/1996 | Sinskey et al. |
| 5,661,026 A | 8/1997 | Peoples et al. |
| 5,958,745 A | 9/1999 | Gruys et al. |
| 6,515,205 B1 | 2/2003 | Liebergesell et al. |
| 6,764,851 B2 | 7/2004 | Nikolau et al. |
| 6,835,820 B2 | 12/2004 | Cannon et al. |
| 6,998,471 B2 | 2/2006 | Hallahn et al. |
| 7,127,379 B2 | 10/2006 | Palsson et al. |

(Continued)

FOREIGN PATENT DOCUMENTS

| | | |
|---|---|---|
| WO | WO 2002/055995 | 7/2002 |
| WO | WO 2003/106998 | 12/2003 |

(Continued)

OTHER PUBLICATIONS

Devos et al., (Proteins: Structure, Function and Genetics, 2000, vol. 41: 98-107.*

(Continued)

*Primary Examiner* — Tekchand Saidha
*Assistant Examiner* — Mohammad Y Meah
(74) *Attorney, Agent, or Firm* — Greenberg Traurig LLP

(57) ABSTRACT

A non-naturally occurring microbial organism includes a microbial organism having a 1,3-butanediol (1,3-BDO) pathway having at least one exogenous nucleic acid encoding a 1,3-BDO pathway enzyme expressed in a sufficient amount to produce 1,3-BDO. The pathway includes an enzyme selected from a 2-amino-4-ketopentanoate (AKP) thiolase, an AKP dehydrogenase, a 2-amino-4-hydroxypentanoate aminotransferase, a 2-amino-4-hydroxypentanoate oxidoreductase (deaminating), a 2-oxo-4-hydroxypentanoate decarboxylase, a 3-hydroxybutyraldehyde reductase, an AKP aminotransferase, an AKP oxidoreductase (deaminating), a 2,4-dioxopentanoate decarboxylase, a 3-oxobutyraldehyde reductase (ketone reducing), a 3-oxobutyraldehyde reductase (aldehyde reducing), a 4-hydroxy-2-butanone reductase, an AKP decarboxylase, a 4-aminobutan-2-one aminotransferase, a 4-aminobutan-2-one oxidoreductase (deaminating), a 4-aminobutan-2-one ammonia-lyase, a butenone hydratase, an AKP ammonia-lyase, an acetylacrylate decarboxylase, an acetoacetyl-CoA reductase (CoA-dependent, aldehyde forming), an acetoacetyl-CoA reductase (CoA-dependent, alcohol forming), an acetoacetyl-CoA reductase (ketone reducing), a 3-hydroxybutyryl-CoA reductase (aldehyde forming), a 3-hydroxybutyryl-CoA reductase (alcohol forming), a 4-hydroxybutyryl-CoA dehydratase, and a crotonase. A method for producing 1,3-BDO, includes culturing such microbial organisms under conditions and for a sufficient period of time to produce 1,3-BDO.

22 Claims, 7 Drawing Sheets

Specification includes a Sequence Listing.

(56) References Cited

U.S. PATENT DOCUMENTS

| | | | |
|---|---|---|---|
| 7,256,016 | B2 | 8/2007 | San et al. |
| 7,309,597 | B2 | 12/2007 | Liao et al. |
| 7,709,261 | B2 | 5/2010 | San et al. |
| 7,838,279 | B2 | 11/2010 | Millis et al. |
| 7,842,497 | B2 | 11/2010 | Millis et al. |
| 7,927,862 | B2 | 4/2011 | Millis et al. |
| 7,947,483 | B2 | 5/2011 | Burgard et al. |
| 2002/0012939 | A1 | 1/2002 | Palsson |
| 2002/0168654 | A1 | 11/2002 | Maranas et al. |
| 2003/0032153 | A1 | 2/2003 | Yamamoto et al. |
| 2003/0059792 | A1 | 3/2003 | Palsson et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2004/0152159 | A1 | 8/2004 | Causey et al. |
| 2004/0199941 | A1 | 10/2004 | San et al. |
| 2007/0134768 | A1 | 6/2007 | Zelder et al. |
| 2007/0141681 | A1 | 6/2007 | Rieping et al. |
| 2008/0032374 | A1 | 2/2008 | Zelder et al. |
| 2008/0038787 | A1 | 2/2008 | Zelder et al. |
| 2008/0293101 | A1 | 11/2008 | Peters et al. |
| 2009/0011480 | A1 | 1/2009 | Trimbur et al. |
| 2009/0061493 | A1 | 3/2009 | Trimbur et al. |
| 2009/0075351 | A1 | 3/2009 | Burk et al. |
| 2009/0111154 | A1 | 4/2009 | Liao et al. |
| 2009/0155869 | A1 | 6/2009 | Buelter et al. |
| 2009/0155873 | A1 | 6/2009 | Kashiyama et al. |
| 2009/0203089 | A1 | 8/2009 | Kashiyama |
| 2009/0269823 | A1 | 10/2009 | Bramucci et al. |
| 2009/0286294 | A1 | 11/2009 | Blanchard et al. |
| 2009/0305363 | A1 | 12/2009 | Anthony et al. |
| 2010/0036174 | A1 | 2/2010 | Raamsdonk et al. |
| 2010/0062505 | A1 | 3/2010 | Gunawardena et al. |
| 2010/0086981 | A1 | 4/2010 | LaTouf et al. |
| 2010/0112654 | A1 | 5/2010 | Burk et al. |
| 2010/0129885 | A1 | 5/2010 | Khramtsov et al. |
| 2010/0143985 | A1 | 6/2010 | Lee et al. |
| 2010/0167363 | A1 | 7/2010 | Bramucci et al. |
| 2010/0167364 | A1 | 7/2010 | Bramucci et al. |
| 2010/0167365 | A1 | 7/2010 | Bramucci et al. |
| 2010/0184195 | A1 | 7/2010 | San et al. |
| 2010/0205857 | A1 | 8/2010 | Dijk et al. |
| 2010/0209983 | A1 | 8/2010 | Park et al. |
| 2010/0221800 | A1 | 9/2010 | Liao et al. |
| 2010/0248233 | A1 | 9/2010 | Muller et al. |
| 2010/0255552 | A1 | 10/2010 | Doyle et al. |
| 2010/0261241 | A1 | 10/2010 | Khramtsov et al. |
| 2010/0285549 | A1 | 11/2010 | Muramatsu et al. |
| 2010/0330635 | A1 | 12/2010 | Burgard et al. |
| 2011/0020889 | A1 | 1/2011 | Feldman et al. |
| 2011/0124060 | A1 | 5/2011 | Anthony et al. |
| 2011/0129904 | A1 | 6/2011 | Burgard et al. |
| 2011/0137088 | A1 | 6/2011 | Borden |
| 2011/0177579 | A1 | 7/2011 | Ma et al. |
| 2011/0183382 | A1 | 7/2011 | Schmalisch et al. |
| 2011/0201072 | A1 | 8/2011 | Bastian et al. |

FOREIGN PATENT DOCUMENTS

| | | |
|---|---|---|
| WO | WO 2008/115840 | 9/2008 |
| WO | WO 2009/014437 | 1/2009 |
| WO | WO 2009/094485 | 7/2009 |
| WO | WO 2010/030711 | 3/2010 |
| WO | WO 2010/071697 | 6/2010 |

OTHER PUBLICATIONS

Witkowski et al., (Biochemistry 38:11643-11650, 1999.*
Whisstock et al., (Quarterly Reviews of Biophysics 2003, vol. 36 (3): 307-340.*
Kisselev L., (Structure, 2002, vol. 10: 8-9.*
Holden et al. Acc Chem Res, 2001, 34, pp. 145-151.*
Woods et al. J. Biochem, 1986, 237, 547-557.*
Goldman et al. BMC EV biol., 2009, 9, p. 1-12.*
UniportKB_ D3VBR5(D3VBR5-XENNA, 2020, pp. 1-6.*
Kegg Enzyme , 2020 pp. 1-2.*
Aberhart and Hsu, "Stereospecific hydrogen loss in the conversion of [2H7] isobutyrate to β-hydroxyisobutyrate in Pseudomonas putida. The stereochemistry of β-hydroxyisobutyrate dehydrogenase," J. Chem. Soc. [Perkin1] 6:1404-1406 (1979).
Abiko et al., "Localization of NAD-isocitrate dehydrogenase and glutamate dehydrogenase in rice roots: candidates for providing carbon skeletons to NADH-glutamate synthase," Plant Cell Physiol. 46:1724-1734 (2005).
Agnihotri and Liu, "Enoyl-CoA Hydratase: Reaction, Mechanism, and Inhibition," Bioorg. Med. Chem. 11(1):9-20 (2003).
Ahmed and Lewis, "Fermentation of Biomass-Generated Synthesis Gas: Effects of Nitric Oxide," Biotechol. Bioeng. 97:1080-1086 (2007).
Alber et al., "Malonyl-Coenzyme A reductase in the modified 3-hydroxypropionate cycle for autotrophic carbon fixation in archaeal Metallosphaera and *Sulfolobus* spp.," J. Bacteriol. 188(24):8551-8559 (2006).
Alber et al., "Study of an alternate glyoxylate cycle for acetate assimilation by Rhodobacter sphaeroides," Mol. Microbiol. 61(2):297-309 (2006).
Alhapel et al., "Molecular and functional analysis of nicotinate catabolism in Eubacterium barkeri," Proc. Natl. Acad. Sci. USA 103(33):12341-12346 (2006).
Alper et al., "Engineering yeast transcription machinery for improved ethanol tolerance and production," Science 314(5805):1565-1568 (2006).
Andersen and Hansen, "Cloning of the lysA gene from *Mycobacterium tuberculosis*," Gene 124(1):105-109 (1993).
Ansorge and Kula, "Production of Recombinant L-Leucine Dehydrogenase from Bacillus cereus in Pilot Scale Using the Runaway Replication System *E. coli*[pIET98]," Biotechnol. Bioeng. 68:557-562 (2000).
Asano and Kato, "Crystalline 3-methylaspartase from a facultative anaerobe, *Escherichia coli* strain YG1002," FEMS Microbiol. Lett. 118(3):255-258 (1994).
Asano et al., "Alteration of substrate specificity of aspartase by directed evolution," Biomol. Eng. 22(1-3):95-101 (2005).
Asuncion et al., "Overexpression, purification, crystallization and data collection of 3-methylaspartase from Clostridium tetanomorphum," Acta. Crystallogr. D. Biol. Crystallogr. 57(Pt 5):731-733 (2001).
Asuncion, et al., "The structure of 3-methylaspartase from Clostridium tetanomorphum functions via the common enolase chemical step," J. Biol. Chem. 277(10):8306-8311 (2002).
Atsumi et al., "Non-fermentative pathways for synthesis of branched-chain higher alcohols as biofuels," Nature 451(7174):86-89 (2008).
Baker and van der Drift, "Purification and properties of L-erythro-3,5-diaminohexanoate dehydrogenase from Clostridium sticklandii," Biochemistry 13(2):292-299 (1974).
Baker et al., "Purification and properties of L-erythro-3,5-diaminohexanoate dehydrogenase from a lysine-fermenting Clostridium," J. Biol. Chem. 247:7724-7734 (1972).
Barrowman et al., "Immunological comparison of microbial TPP-dependent non-oxidative α-keto acid decarboxylase," FEMS Microbiol. Lett. 34:57-60 (1986).
Barthelmebs et al., "Exression of *Escherichia coli* of Native and chimeric Phenolic Acid Decarboxylases with Modified Enzymatic Activities and Method for Screening Recombinant E. coli Strains Expressing These Enzymes," Appl. Environ. Microbiol. 67:1063-1069 (2001).
Benner et al., "Stereospecificity and sterochemical infidelity of acetoacetate decarboxylase (AAD)," J. Am. Chem. So. 103:993-994 (1981).
Berg et al., "A 3-Hydroxypropionate/4-Hydroxybutyrate Autotrophic Carbon Dioxide Assimilation Pathway in Archaea," Science 318(5857) 1782-1786 (2007).
Bergquist and Gibbs, "Degenerate oligonucleotide gene shuffling," Meth. Mol. Biol. 352:191-204 (2007).

(56) References Cited

OTHER PUBLICATIONS

Bergquist et al., "Degenerate oligonucleotide gene shuffling (DOGS) and random drift mutagenesis (RNDM): Two complementary techniques for enzyme evolution," Biomol. Eng. 22:63-72 (2005).
Berthold et al., "Structure of the branched-chain keto acid decarboxylase (KdcA) from Lactococcus lacti prvides insights into structural basis for the chemoselective enantioselective catholigation reaction," Acta. Crystallogr. D. Biol. Crystallogr. 63(Pt 12):1217-1224 (2007).
Binstock and Schulz, "Fatty acid oxidation complex from *Escherichia coli*," Methods Enzymol. 71(Pt C):403-411 (1981).
Bonnarme et al., "Itaconate biosynthesis in Aspergillus terreus," J. Bacteriol. 177(12):3573-3578 (1995).
Botting et al., "Substrate Specificity of the 3-Methylaspartate Ammonia-Lyase Reactin: Observation of Differential relative Reaction Rates for Substrate-Product Pairs," Biochemistry 27:2953-2955 (1988).
Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobutylicum ATCC 824," J. Bacteriol. 178(11):3015-3024 (1996).
Bravo et al., "Reliable, sensitive, rapid and quantitative enzyme-based assay for gamma-hydroxybutyric acid (GHB)," J. Forensic Sci. 49:379-387 (2004).
Bredwell et al., "Reactor Design Issues for Synthesis-Gas Fermentations," Biotechnol. Prog. 15(5):834-844 (1999).
Breitkreuz et al., "A novel γ-hydroxybutyrate dehydrogenase: Identification and expression of an *Arabidopsis* cDNA and potential role under oxygen deficiency," J. Biol. Chem. 278:41552-41556 (2003).
Burgard et al., Minimal Reaction Sets for *Escherichia coli* Metabolism under Different Growth Requirements and Uptake Environments. Biotechnol. Prog. 17:791-797 (2001).
Burgard et al., "Optknock: a bilevel programming framework for identifying gene knockout strategies for microbial strain optimization," Biotechnol. Bioeng. 84(6):647-657 (2003).
Cahyanto et al., "Regulation of aspartokinase, asparate semialdehyde dehydrogenase, dihydrodipicolinate synthease and dihydropdipicolinate reductase in Lactobacillus plantarum," Microbiology. 152 (Pt 1): 105-112 (2006).
Cavin et al., "Gene cloning, transcriptional analysis, purification, and characterization of phenolic acid decarboxylase from bacillus subtilis," Appl. Environ. Microbiol. 64(4):1466-1471 (1998).
Chandra et al. "Pyruvate decarboxylase: a key enzyme for the oxidative metabolism of lactic acid by Acetobacter pasteurianus," Arch. Microbiol. 176:443-451 (2001).
Cho et al., "Critical residues for the Coenzyme specificity of NAD+-dependent 15-hydroxyprostaglandin dehydrogenase," Arch Biochem. Biophys. 419:139-146 (2003).
Chopra et al., "Expression, purification, and biochemical characterization of *Mycobacterium tuberculosis* aspartate decarboxylase, PanD," Protein Expr. Purif. 25:533-540 (2002).
Chowdhury et al., "3-Hydroxyisobutymte dehydrogenase from Pseudomonas putida E23: purification and characterization," Biosci. Biotechnol. Biochem. 60(12):2043-2047 (1996).
Chowdhury et al., "Cloning and overexpression of the 3-hydroxyisobutyrate dehydrogenase gene from pseudomonas putida E23," Biosci. Biotechnol. Biochem. 67(2):438-441 (2003).
Clarke et al., "Rational construction of a 2-Hydroxyacid Dehydrogenase With New Substrate Specificity," Biochem. Biophys. Res. Commun. 148:15-23 (1987).
Clausen et al., "PAD1 encodes phenylarcrylic acid decarboxylase which confers resistance to cinnamic acid in *Saccharomyces cerevisiae*," Gene 142:107-112 (1994).
Coco et al., "DNA shuffling method for generating highly recombined genes and evolved enzymes," Nat. Biotechnol. 19:354-359 (2001).
Conrad et al., "D- and L-Isoleucine Metabolism and Regulation of Their Pathways in Pseudomonas Putida," J. Bacteriol. 118(1):103-111 (1974).
Datar et al., "Fermentation of biomass-generated producer gas to ethanol," Biotechnol. Bioeng. 86(5):587-594 (2004).

De la Torre et al., "Identification and functional analysis of a prokaryotic-type aspartate aminotransferase: implications for plant amino acid metabolism," Plant. J. 46(3):414-425 (2006).
Diaz et al., "Gene cloning, heterologous overexpression and optimized refolding of the NAD-glutamate dehydrogenase from Haloferax mediterranei," Extremophiles 10:105-115 (2006).
Doyle et al., "Structural Basis for a Change in substrate Specificity: Crystal Structure of S113E Isocitrate Dehydrogenase in a Complex with Isopropylmalate, Mg2+ and NAPD," Biochemistry 40:4234-4241 (2001).
Drummond and Stern, "Enzymes of ketone body metabolism. II. Properties of an acetoacetate-synthesizing enzyme prepared from ox liver," J. Biol. Chem. 235:318-325 (1960).
Dusch et al., "Expression of the Corynebacterium glutamicum panD gene encoding L-aspartate-α-decarboxylase leads to pantothenate overproduction in *Escherichia coli*," Appl. Environ. Microbiol. 65(4):1530-1539 (1999).
Edegger et al., "Biocatalytic deuterium- and hydrogen-transfer using over-expressed ADH-'A': enhanced steroselectivity and 2H-labeled chiral alcohols," Chem. Commun. 22:2402-2404 (2006).
Endo et al., "Microbial Conversion with Cofactor Regeneration using Genetically Engineered Bacteria," Adv. Synth. Catal., 343(6-7):521-526 (2001).
Fitzgerald and Flanagan, "Characterization and sequence analysis of the human ornithine decarboxylase gene," DNA 8:(9):623-634 (1989).
Fong and Palsson, "Metabolic gene-deletion strains of *Escherichia coli* evolve to computationally predicted growth phenotypes," Nat. Genet. 36(10):1056-1058 (2004).
Fonknechten et al., "A conserved gene cluster rules anaerobic oxidative degradation of L-ornithine," J. Bacteriol. 191(9):3162-3167 (2009).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," J. Bacteriol. 184:821-830 (2002).
Fujii et al., "Characterization of L-lysine 6-aminotransferase and its structural gene from Flavobacterium lutescens IFO3084," J. Biochem. 128:391-397 (2000).
Fujii et al., "Error-prone rolling circle amplification: the simplest random mutagenesis protocol," Nat. Protoc. 1:2493-2497 (2006).
Fujii et al., "One-step random mutagenesis by error-prone rolling circle amplification," Nucleic Acids Res. 32:e145 (2004).
Fujita et al., "Novel Substrate Specificity of Designer 3-Isopropylmalate Dehydrogenase Derived from Thermus thermophilus HB8," Biosci. Biotechnol. Biochem. 65(12):2695-2700 (2001).
Gibbs et al., "Degenerate olignucleotide gene shuffling (DOGS): a method for enhancing the frequence of recombination with family shuffling," Gene 271:13-20 (2001).
Goda et al., "Cloning, sequencing, and expression in *Escherichia coli* of the Clostridium tetanomorphum gene encoding β-methylaspartase and characterization of the recombinant protein," Biochemistry 31(44):10747-10756 (1992).
Gokulan et al., "Crystal structure of *Mycobacterium tuberculosis* diaminipimelate decarboxylase, an essential enzyme in bacterial lysine biosynthesis," J. Biol. Chem. 278(20):18588-18596 (2003).
Green et al., "Catabolism of a-ketoglutarate by a sucA mutant of Bradyrhizobium japonicum: evidence for an alternative tricarboxylic acid cycle," J. Bacteriol. 182:2838-2844 (2000).
Guest et al., "The fumarase genes of *Escherichia coli*: location of the fumB gene and discovery of a new gene (fumC)," J. Gen. Microbiol. 131(11):2971-2984 (1985).
Guirard and Snell, "Purification and properties of ornithine decarboxylase from *Lactobacillus* sp. 30a," J. Biol. Chem. 255:5960-5964 (1980).
Gutierrez et al., "A mutant D-amino acid aminotransferase with broad substrate specificity: construction by replacement of the interdoman loop Pro119-Arg120-Pro121 by Gly-Gly-Gly," Protein Eng. 11:53-58 (1998).

(56) References Cited

OTHER PUBLICATIONS

Gutierrez et al., "Modulation of activity and substrate specificity by modifying the backbone length of the distant interdomain loop of D-amino acid aminotransferase," Eur. J. Biochem. 267(24):7218-7223 (2000).
Haller et al., "Discovering new enzymes and metabolic pathways: conversion of succinate to propionate by *Escherichia coli*," Biochem. 39(16):4622-4629 (2000).
Hammer and Bode, "Purification and characterization of an inducible L-lysine:2-oxoglutarate 6-aminotransferase from Candida utilis," J. Basic Microbiol. 32:21-27 (1992).
Hanai et al., "Engineered synthetic pathway for isopropanol production in *Escherichia coli*," Appl. Environ. Microbiol. 73(24):7814-7818 (2007).
Hashidoko et al., "Cloning of a DNA fragment carrying the 4-hydroxycinnamate decarboxylase (pofK) gene from Klebsielss oxytoca and its constitutive expression in *Escherichia coli* JM109 cells," Biosci. Biotech. Biochem. 58(1):217-218 (1994).
Hashimoto et al., "Activation of L-Lysine ε-Dehydrogenase from Agrobacterium tumefaciens by Several Amino Acids and Monocarboxylates," J. Biochem. 106:76-80 (1989).
Hasson et al., "The crystal structure of benzoylfomate decarboxylase at 1.6 Å resolution: diversity of catalytic residues in thiamin diphosphate-dependent enzymes," Biochemistry 37:9918-9930 (1998).
Hawes et al., "Mammalian 3-hydroxyisobutyrate dehydrogenase," Methods Enzymol. 324:218-228 (2000).
Hayden et al., "Glutamate dehydrogenase of Halobacterium salinarum: evidence that the gene sequence currently assigned to the NADP+-dependent enzyme is in fact that of the NAD+-dependent glutamate dehydrogenase," FEMS Microbiol. Lett. 211:37-41 (2002).
Hayes et al., "Combining computational and experimental screening for rapid optimization of protein properties," Proc. Natl. Acad. Sci. USA 99(25):15926-15931 (2002).
Henning et al., "Identification of novel benzoylformate decarboxylases by growth selection," Appl. Environ. Microbiol. 72:7510-7517 (2006).
Hermes et al., "Searching sequence space by definably random mutagenesis: Improving the catalytic potency of an enzyme," Proc. Natl. Acad. Sci. USA 87:696-700 (1990).
Heydari et al., "Highly Stable L-Lysine 6-Dehydrogenase from the thermophile Geobacillus stearothermophilus Isolated from a Japanese Hot Spring: characterization, Gene Cloning and sequencing, and Expression," Appl. Environ. Microbiol. 70(2):937-942 (2004).
Hibbert et al., "Directed evolution of biocatalytic processes," Biomol. Eng. 22:11-19 (2005).
Highbarger et al., "Mechanism of the reaction catalyzed by acetoacetate decarboxylase. Importance of lysine 116 in determining the pKa of active-site lysine 115," Biochemistry 35(1):41-46 (1996).
Hillmer and Gottschalk, "Particulate Nature of Enzymes Involved in the Fermentation of Ethanol and Acetate by Clostridium Kluyveri," FEBS Lett. 21(3):351-354 (1972).
Hillmer and Gottschalk, "Solubilization and partial characterization of particulate dehydrogenases from Clostridium kluyveri," Biochim. Biophys. Acta. 334:12-23 (1974).
Hirano et al., "Purification and characerization of the Alcohol Dehydrogenase with a Broad Substrate Specificy Originated from 2-Phenylethanol-Assimilating *Brevibacterium* sp. KU 1309," J. Biosci. Bioeng. 100(3): 318-322 (2005).
Hoffmeister et al., "Mitochondrial trans-2-enoyl-CoA reductase of wax ester fermentation from Euglena gracilis defines a new family of enzymes involved in lipid synthesis," J. Biol. Chem. 280(6):4329-4338 (2005).
Hogan et al., "Improved Specificity toward Substrates with Positively Charged Side chains by Site-Directed Mutagenesis of the L-Lactate Dehydrogenase of Bacillus stearothermophilus," Biochemistry 34:4225-4230 (1995).
Hu et al., "The catalytic intermediate stabilized by a "down" active site loop for diaminopimelate decarboxylase from Helicobacter pylori. Enzymatic characterization with crystal structure analysis," J. Biol. Chem. 283(30):21284-21293 (2008).

Huang et al., "Purification and characterization of a ferulic acid decarboxylase from Pseudomonas fluorescens," J. Bacteriol. 176:5912-5918 (1994).
Hughes et al.,"Evidence for isofunctional enzymes in the degradation of phenol, m- and p-toluate, and p-cresol via catechol meta-cleavage pathways in Alcaligenes eutrophus," J. Bacteriol. 158(1):79-83 (1984).
Hugler et al., "Malonyl-Coenzyme A Reductase from Chloroflexus aurantiacus, a Key Enzyme of the 3-Hydroxypropionate Cycle for Autotrophic CO2 Fixation," J. Bacteriol. 184(9):2404-2410 (2002).
Huisman and Lalonde, "Enzyme evolution for chemical process applications," In R.N. Patel (ed.), Biocatalysis in the pharmaceutical and biotechnology industries, CRC Press, p. 717-742 (2007).
Ichikawa et al. Catalytic reaction of 1,3-butanediol over solid acids, J. Mol. Catalysis A Chem. 256:106-112 (2006).
Ichikawa et al., "PIO study on 1,3-butanediol dehydration over CeO2 (1 1 1) surface," J. Mol. Catalysis A Chem. 231:181-189 (2005).
Iffland et al., "Directed Molecular Evolution of Cytochrome c Peroxidase," Biochemistry 39:10790-10798 (2000).
Ikai and Yamamoto, "Identification and analysis of a gene encoding L-2,4-diaminobutyrate:2-ketoglutarate 4-aminotransferase involved in the 1,3-diaminopropane production pathway in Acinetobacter baummanni," J Bacteriol. 179:5118-5125 (1997).
Ingoldsby et al., "The discovery of four distinct glutamate dehydrogenase genes in a strain of Halobacterium salinarum," Gene 349:237-244 (2005).
Ishige et al., "Wax ester production from n-alkanes by *Acinetobacter* sp. strain M-1: ultrastructure of cellular inclusions and role of acyl Coenzyme A reductase," Appl. Environ. Microbiol. 68(3):1192-1195 (2002).
Ismaiel et al., "Purification and Characterization of a Primary-Secondary Alcohol Dehydrogenase from Two Strains of Clostridium beijerinckii," J. Bacteriol. 175(16):5097-5105 (1993).
Ismail et al., "Functional genomics by NMR spectroscopy. Phenylacetate catabolism in *Escherichia coli*," Eur. J. Biochem. 270(14):3047-3054 (2003).
Jacques et al., "Characterization of yeast homoserine dehydrogenase, an antifungal target: the invariant histidine 309 is important for enzyme integrity," Biochem. Biophys. Acta 1544:28-41 (2001).
James and Viola, "Production and characterization of bifunctional enzymes. Domain swapping to produce new bifunctional enzymes in the aspartate pathway," Biochemistry 41(11) 3720-3725 (2002).
Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," Biochemistry 13(14):2898-2903 (1974).
Jeon et al., "Heterologous expression of the alcohol dehydrogenase (adhI) gene from Geobacillius thermoglucosidasius strain M10EXG," J. Biotechnol. 135:127-133 (2008).
Jiang et al., "De Novo Computational Design of Retro-Aldol Enzymes," Science 319: 1387-1391 (2008).
Johnson et al., "Alteration of a single amino acid changes the substrate specificity of dihydroflavonol 4-reductase," Plant J. 25(3):325-333 (2001).
Jones and Woods,"Acetone-butanol fermentation revisited," Microbiol. Rev. 50(4):484-524 (1986).
Kalapos, "On the mammalian acetone metabolism: from chemistry to clinical implications," Biochim. Biophys. Acta 1621(2):122-139 (2003).
Kanamasa et al., "Cloning and functional characterization of the cis-aconitic acid decarboxylase (CAD) gene from Aspergillus terreus," Appl. Microbiol. Biotechnol. 80(2):223-229 (2008).
Kato and Asano, "3-Methylaspartate ammonia-lyase as a marker enzyme of the mesaconate pathway for (S)-glutamate fermentation in Enterobacteriaceae," Arch. Microbiol. 168(6):457-463 (1997).
Kazahaya et al, "Aerobic Dissimilation of Glucose by Heterolactic Bacteria III. Aldehyde dehydrogenase and alcohol dehydrogenase of luconostoc mesenteroids" J. Gen. Appl. Microbiol. 18(1):43-55 (1972).
Kefala et al., "Cloning, expression, purification, crystallization and preliminary x-ray diffraction analysis of LysA (Rv1293) from

(56) References Cited

OTHER PUBLICATIONS

*Mycobacterium tuberculosis*," Acta. Crystallogr. Sect. F. Struct. Biol. Cryst. Commun. 61(Pt 8):782-784 (2005).

Kenklies et al., "Proline biosynthesis from L-ornithine in Clostridium sticklandii. purification of Δ1-pyrroline-5-carboxylate reductase, and sequence and expression of encoding gene, prof," Microbiology 145(Pt 4):819-826 (1999).

Kessler et al., "Pyruvate-formate-lyase-deactivase and acetyl-CoA reductase activities of *Escherichia coli* reside on a polymeric protein particle encoded by adhE," FEBS Lett. 281(1-2):59-63 (1991).

Khan et al., "Molecular Properties and Enhancement of Thermostability by Random Mutagenesis of Glutamate Dehydrogenase from Bacillus subtilis," Biosci. Biotechnol. Biochem. 69(10):1861-1870 (2005).

Killenberg-Jabs et al., "Active oligomeric states of pyruvate decarboxylase and their functional characterization," Eur. J. Biochem. 268:1698-1704 (2001).

Kim, "Purification and Properties of a diamine α-Ketoglutarate Transminase from *Escherichia coli*," J. Biol. Chem. 239(3):783-786 (1964).

Kino et al. Synthesis of DL-tryptophan by modified broad specificity amino acid racemase from Pseudomonas putida IFO 12996, Appl. Microbiol. Biotechnol. 73:1299-1305 (2007).

Kinoshita, "Purification of two alcohol dehydrogenases from Zymomonas mobilis and their properties," Appl. Microbiol. Biotechnol. 22:249-254 (1985).

Klatt et al., "Comparative genomics provides evidence for the 3-hydroxypropionate autotrophic pathway in filamentous anoxygenic phototrophic bacteria and in hot spring microbial mats," Environ. Microbiol. 9:2067-2078 (2007).

Kobayashi et al., "Physicochemical, catalytic, and immunochernical properties of fumarases crystallized separately from mitochondrial and cytosolic fractions of rat liver," J. Biochem. 89(6):1923-1931 (1981).

Kollmann-Koch et al.,"Nicotinic acid metabolism. Dimethylmaleate hydratase," Hoppe Seylers Z Physiol Chem. 365:s.847-857 (1984).

Koo et al., "Cloning and characterization of the bifunctional alcohol/acetaldehyde dehydrogenase gene (adhE) in Leuconostoc mesenteroides isolated from kimchi," Biotechnol. Lett. 27(7):505-510 (2005).

Korbert et al., "Crystallization of the NADP+-dependent Glutamate Dehydrogenase from *Escherichia coli*," J. Mol. Biol. 234:1270-1273 (1993).

Kort et al., "Glutamate dehydrogenase from the hyperthermophilic bacterium Thermotoga maritima: molecular characterization and phylogenetic implications," Extremophiles 1:52-60 (1997).

Kosaka et al., "Characterization of the sol operon in butanol-hyperproducing Clostridium saccharoperbutylacetonicum strain N1-4 and its degeneration mechanism," Biosci. Biotechnol. Biochem. 71:58-68 (2007).

Kosjek et al., "Purification and characterization of a chemotolerant alcohol dehydrogenase applicable to coupled redox reactions," Biotechnol. Bioeng. 86(1):55-62 (2004).

Kreimeyer et al., "Identification of the Last Unknown Genes in the Fermentation Pathway of Lysine," J. Biol. Chem. 282(10):7191-7197 (2007).

Kretz et al., "Gene site saturation mutagenesis: a comprehensive mutagenesis approach," Methods Enzymol. 388:3-11 (2004).

Krieger et al., "Pyruvate decarboxylase from Kluyveromyces lactis an enzyme with an extraordinary substrate activation behaviour," Eur. J. Biochem. 269:3256-3263 (2002).

Kumamaru et al., "Enhanced degradation of polychlorinated biphenyls by directed evolution of biphenyl dioxygenase," Nat. Biotechnol. 16:663-666 (1998).

Kuznetsova et al., "Enzyme genomics: Application of general enzymatic screens to discover new enzymes," FEMS Microbiol. Rev. 29(2):263-279 (2005).

Kwok and Hanson, "GFP-labelled Rubisco and aspartate aminotransferase are present in plastid stromules and traffic between plastids," J. Exp. Bot. 55(397):595-604 (2004).

Lamed and Zeikus, "Novel NADP-linked alcohol-aldehyde/ketone oxidoreductase in thermophilic ethanologenic bacteria," Biochem. J. 195:183-190 (1981).

Lebbink et al., "Engineering activity and stability of Thermotoga maritima glutamate dehydrogenase I. Introduction of a six-residue ion-pair network in the hinge region," J. Mol. Biol. 280:287-296 (1998).

Lee and Cho, "Identification of essential active-site residues in ornithine decarboxylase of Nicotiana glutinosa decarboxylating both L-ornithine and L-lysine," Biochem. J. 360:657-665 (2001).

Lee et al., "A new approach to directed gene evolution by recombined extension on truncated templates (RETT)," J. Molec. Catalysis 26:119-129 (2003).

Lee et al., "Phylogenetic diversity and the structural basis of substrate specificity in the β/α-barrel fold basic amino acid decarboxylases," J. Biol. Chem. 282:27115-27125 (2007).

Li and Jordan, "Effects of substitution of tryptophan 412 in the substrate activation pathway of yeast pyruvate decarboxylase," Biochemistry 38:10004-10012 (1999).

Lian et al., "Stereochemical and Isotopic Labeling Studies of 4-Oxalocrotonate Decarboxylase and Vinylpyruvate hydratase: Analysis and Mechanistic Implications," J. Am. Chem Soc. 116:10403-10411 (1994).

Lin et al., "Functional Expression of Horseradish Peroxidase in *E. coli* by Directed Evolution," Biotechnol. Prog. 15:467-471 (1999).

Lin et al., "Fed-batch culture of a metabolically engineered *Escherichia coli* strain designed for high-level succinate production and yield under aerobic conditions," Biotechnol. Bioeng. 90:775-779 (2005).

Lingen et al., "Alteration of the substrate specificity of benzoylformate decarboxylase from Pseudomonas putida by directed evolution," Chembiochem. 4:721-726 (2003).

Lingen et al., "Improving the calboligase activity of benzoylformate decarboxylase from Pseudomonas putida by a combination of directed evolution and site-directed mutagenesis," Protein Eng. 15:585-593 (2002).

Lokanath et al., "Crystal structure of novel NADP-dependent 3-hydroxyisobutyrate dehydrogenase from Thermus thermophilus HB8," J. Mol. Biol. 352(4):905-917 (2005).

Low et al., "Mimicking somatic hypermutation: Affinity maturation of antibodies displayed on baceriophage using a bacterial mutator strain," J. Mol. Biol. 260(3):359-368 (1996).

Lu et al., "Functional Analysis and Regulation of the Divergent spuABCDEFGH-spuI Operons for Polyamine Uptake and Utilization in Pseudomonas aeruginosa PAO1," J. Bacteriol. 184(14):3765-3773 (2002).

Lutz et al., "Creating multiple-crossover DNA libraries independent of sequence identity," Proc. Natl. Acad. Sci USA 98:11248-11253 (2001).

Lutz et al., "Rapid generation of incremental truncation libraries for protein enginering using α-phosphothioate nucleotides," Nucleic Acids Res. 29:E16 (2001).

Ma et al., "Induced rebuilding of aspartase conformation," Ann. NY Acad. Sci. 672:60-65 (1992).

Manning and Pollitt, "Tracer studies of the interconversion of R- and S-methylmalonic semialdehydes in man," Biochem. J. 231(2):481-484 (1985).

Marks et al., "Molecular cloning and characterization of (R)-3-hydroxybutyrate dehydrogenase from human heart," J. Biol. Chem. 267(22):15459-15463 (1992).

Martinez-Carrion and Jenkins, "D-Alanine-D-glutamate transminase I Purification and characterization," J. Biol. Chem. 240(9):3538-3546 (1965).

Matiasek et al., "Volatile ketone formation in bacteria: release of 3-oxopentanoate by soil pseudomonads during growth on heptanoate," Curr. Microbiol. 42:276-281 (2001).

Matsuyama et al., "Industrial production of (R)-1,3-butanediol by new biocatalysts," J. Molecular Catalysis B: Enzymatic, 11:513-521 (2001).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," Appl. Environ. Microbiol. 58(5):1435-1439 (1992).

(56) References Cited

OTHER PUBLICATIONS

McPherson and Wootton, "Complete nucleotide sequence of the *Escherichia coli* gdhA gene," Nucleic Acids Res. 11:5257-5266 (1983).
Meng and Chuang, "Site-directed Mutagenesis and Functional Analysis of the Active-Site Residues of the E2 Component of Bovine Branched-Chain α-Keto Acid Dehydrogenase Complex," Biochemistry 33:12879-12885 (1994).
Merkel and Nichols, "Characterization and sequence of the *Escherichia coli* panBCD gene cluster," FEMS Microbiol. Lett. 143(2-3):247-252 (1996).
Metz et al., "Purification of a jojoba embryo fatty acyl-Coenzyme A reductase and expression of its cDNA in high erucic acid rapeseed," Plant Phys. 122:635-644 (2000).
Misono and Nagasaki, "Occurrence of L-Lysine ε-Dehydrogenase in Agrobacterium tumefaciens," J. Bacteriol. 150(1):398-401 (1982).
Miyazaki et al., "α-Aminoadipate aminotransferase from an extremely thermophilic bacterium, Thermus thermophilus," Microbiology 150:2327-2334 (2004).
Mizobata et al., "Purification and characterization of a thermostable class II fumarase from Thermus thermophilus," Arch. Biochem. Biophys. 355(1):49-55 (1998).
Momany et al., "Crystallization of diaminopimelate decarboxylase from *Escherichia coli*, a stereo specific D-amino-acid decarboxylase," Acta. Crystallogr. D. Biol. Crystallogr. 58(Pt 3):549-552 (2002).
Muller et al., "Nucleotide exchange and excisiion technology (NExT) DNA shuffling; a robust method for DNA fragmentation and directed evolution," Nucleic Acids Res. 33:e117 (2005).
Najafpour and Younesi, "Ethanol and acetate synthesis from waste gas using batch culture of Clostridium ljungdahlii," Enzyme Microb. Technol. 38:223-228 (2006).
Ness et al., "Synthetic shuffling expands functional protein diversity by allowing amino acids to recombine independently," Nat. Biotechnol. 20:1251-1255 (2002).
Nowicki et al., "Recombinant tyrosine aminotransferase from Trypanosoma cruzi: structural characterization and site directed mutagenesis of a broad substrate specificity enzyme," Biochim. Biophysica Acta 1546:268-281 (2001).
Oku and Kaneda, "Biosynthesis of branched-chain fatty acids in bacillus subtilis. A decarboxylase is essential for branched-chain fatty acid synthetase," J. Biol. Chem. 263:18386-18396 (1988).
Okuno et al., "2-Aminoadipate-2-oxoglutarate aminotransferase isoenzymes in human liver: a plausible physiological role in lysine and tryptophan metabolism." Enzyme Protein 47:136-148 (1993).
Olivera et al., "Molecular characterization of the phenylacetic acid catabolic pathway in Pseudomonas putida U: the phenylacetyl-CoA catabolon," Proc. Natl. Acad. Sci. USA 95(11):6419-6424 (1998).
Onuffer and Kirsch, "Redesign of the substrate specificity of *Escherichia coli* aspartate aminotransferase to that of *Escherichia coli* tyrosine aminotransferase by homology modeling and site-directed mutagenesis," Protein Sci. 4:1750-1757 (1995).
Ostermeier et al., "A Combinatorial approach to hybrid enzymes independent of DNA homology," Nat. Biotechnol. 17:1205-1209 (1999).
Ostermeier et al., "Combinatorial protein engineering by incremental truncation," Proc. Natl. Acad. Sci. USA 96:3562-3567 (1999).
Otten and Quax, "Directed evolution:selecting today's biocatalysts," Biomol. Eng. 22:1-9 (2005).
Park and Lee, "Biosynthesis of poly(3-hydroxybutyrate- co-3-hydroxyalkanoates) by metabolically engineered *Escherichia coli* strains," Appl. Biochem. Biotechnol. 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," J. Bacteriol. 185(18):5391-5397 (2003).
Park and Lee, "New FadB homologous enzymes and their use in enhanced biosynthesis of medium-chain-length polyhydroxyalkanoates in FadB mutant *Escherichia coli*," Biotechnol. Bioeng. 86(6):681-686 (2004).

Paxton et al., "Role of branched-chain 2-oxo acid dehydrogenase and pyruvate dehydrogenase in 2-oxobutyrate metabolism," Biochem. J. 234:295-303 (1986).
Peisach et al., "Crystallographic study of steps along the reaction pathway of D-amino acid aminotransferase," Biochemistry 37(14)4958-4967 (1998).
Peoples and Sinskey, "Fine structural analysis of the Zoogloea ramigera phbA-phbB locus encoding β-ketothiolase and acetoacetyl-CoA reductase: nucleotide sequence of phbB," Mol. Microbiol. 3:349-357 (1989).
Peretz and Burstein, "Amino acid sequence of alcohol dehydrogenase from the thermophilic bacterium Thermoanaerobium brockii," Biochemistry 28(16):6549-6555 (1989).
Perez et al., "*Escherichia coli* YqhD exhibits aldehyde reductase activity and protects from the harmful effect of lipid peroxidation-derived aldehydes," J. Biol. Chem. 283(12):7346-7353 (2008).
Petersen and Bennett, "Purification of acetoacetate decarboxylase from clostridium acetobutylicum ATCC 824 and cloning of the acetoacetate decarboxylase gene in *Escherichia coli*," Appl. Environ. Microbiol. 56:3491-3498 (1990).
Ploux et al., "The NADPH-linked acetoacetyl-CoA reductase from Zoogloea ramigera, Characterization and mechanistic studies of the cloned enzyme over-produced in *Escherichia coli*," Eur. J. Biochem. 174:177-182 (1988).
Polovnikova et al., "Structural and kinetic analysis of catalysis by a thiamine diphosphate-deptendent enzyme, benzoylformate decarboxylase," Biochemistry 42:1820-1830 (2003).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," J. Bacteriol. 175(2):377-385 (1993).
Pritchard et al., "A general model of error-prone PCR," J. Theor. Biol. 234:497-509 (2005).
Pucci et al., "*Staphylococcus haemolyticus* contains two D-glutamic acid biosynthetic activities, a glutamate racemase and a D-amino acid transminase," J. Bacteriol. 177(2):336-342 (1995).
Purnell et al., "Modulation of higher-plant NAD(H)-dependent glutamate dehydrogenase activity in transgenic tobacco via alteration of β subunit levels," Planta 222:167-180 (2005).
Qu et al., "Inhibition of human ornthine decarboxylase activity by enantiomers of difluoromethylornithine," Biochem. J. 375:465-470 (2003).
Rajpal et al., "A general method for greatly improving the affinity of antibodies by using combinatorial libraries," Proc. Natl. Acad. Sci. USA 102:8466-8471 (2005).
Ramjee et al., "*Escherichia coli* L-aspartate-α-decarboxylase: preprotein processing and observation of reaction intermediates by electrospray mass spectrometry," Biochem. J. 323(Pt 3):661-669 (1997).
Ravagnani et al., "Spo0A directly controls the switch from acid to solvent production in solvent-forming clostridia," Mol. Microbiol. 37(5):1172-1185 (2000).
Recasens et al., "Cystein Sulfinate Aminotransferase and Aspartate Aminotransferase Isoenzymes of Rat Brain. Purification, Characterization, and Further Evidence of Identity," Biochemistry 19:4583-4589 (1980).
Reetz and Carballeira, "Iterative saturation mutagenesis (ISM) for rapid directed evolution of functional enzymes," Nat. Protoc. 2:891-903 (2007).
Reetz et al., "Creation of Enantioselective Biocatalysts for Organic Chemistry by In Vitro Evolution," Angew. Chem. Int. Ed. Engl. 36:2830-2832 (1997).
Reetz et al., "Directed Evolution of an Enantioselective Enzyme through Combinatorial Multiple-Cassette Mutagenesis," Angew. Chem. Int. Ed. Engl. 40:3589-3591 (2001).
Reetz et al., "Expanding the Range of Substrate Acceptance Enzymes: Cominatorial Active-Site Saturation Test," Angew. Chem. Int. Ed. 44:4192-4196 (2005).
Reetz et al., "Iterative saturation mutagenesis on the basis of B factors as a strategy for incresing protein thermostability," Angew. Chem. Int. Ed. 45:7745-7751 (2006).
Reidhaar-Olson and Sauer, "Combinatorial cassette mutagenesis as a probe of the informational content of protein sequences," Science 241:53-57 (1988).

(56) References Cited

OTHER PUBLICATIONS

Reidhaar-Olson et al., "Random mutagenesis of protein sequences using oligonucleotide cassettes," Methods Enzymmol. 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase," J. Bacteriol. 179(9):2969-2975 (1997).
Roberts et al, "The Role of Enoyl-CoA Hydratase in the Metabolism of Isoleucine by Pseudomonas putida," Arch. Microbiol. 117:99-108 (1978).
Roca et al., "Metabolic engineering of ammonium assimilation in xylose-fermenting Saccharomyces cerevisiae improves ethanol production," Appl. Environ. Microbiol. 69:4732-4736 (2003).
Rodriguez et al., "Characterization of the p-Coumaric Acid Decarboxylase from Lactobacillus plantarium CECT 748T," J. Agric. Food Chem. 56:3068-3072 (2008).
Romero et al., "Partial purification and characterization and nitrogen regulation of the lysine e-aminotransferase of Streptomyces clavuligers, " J. Ind. Microbiol. Biotechnol. 18:241-246 (1997).
Rozell and Benner, "Stereochemical Imperative in Enzymic Decarboxylation. Stereochemical Course of Decarboxylation Catalyzed by Acetoacetate Decarboxylase," J. Am. Chem. Soc. 106:4937-4941 (1984).
Ruldeekulthamrong et al., "Molecular characterization of lysine 6-dehydrogenase from Achromobacter denitrificans," BMB Reports 790-795 (2008).
Sakai et al, "Acetate and Ethanol Production from H2 and CO2 by Morrella sp. Using a Repeated Batch Culture," J. Biosci. Bioeng. 99:252-258 (2005).
Samsonova et al., "Molecular cloning and characterization of Escherichia coli K12 ygjG gene," BMC Microbiol. 3:2 (2003).
Sariaslani, "Development of a Combined biological and Chemical Process for Production of Industrial aromatics from Renewable Resources," Annu. Rev. Microbiol. 61:51-69 (2007).
Scherf and Buckel, "Purification and properties of an iron-sulfur and FAD-containing 4-hydroxybutyryl-CoA dehadratase/vinylacetyl-CoA Δ3-Δ2-isomerase from Clostridium aminobutricum," Eur. J. Biochem. 215:421-429 (1993).
Scherf et al, "Succinate-ethanol fermentation in clostridium kluyveri: purification and characterisation of 4-hydroxybutyryl-CoA dehydratase/vinylacetyl-CoA Δ3-Δ2-isomerase," Arch. Microbiol. 161(3):239-245 (1994).
Schmitzberger et al., "Structural constraints on protein self-processing in L-aspartate-α-decarboxylase," EMBO J. 22:6193-6204 (2003).
Selifonova et al., "Rapid evolution of novel traits in microorganisms," Appl Environ Microbiol. 67:3645-3649 (2001).
Sen et al., "Developments in directed evolution for improving enzyme functins," Appl. Biochem. Biotechnol. 143:212-223 (2007).
Shao et al., "Random-priming in vitro recombination: an effective tool for directed evolution," Nucleic Acids Res. 26:681-683 (1998).
Shiba et al., "Engineering of the pyruvate dehydrogenase bypass in Saccharomyces cerevisiae for high-level production of isoprenoids," Metabolic Engineering 9:160-168 (2007).
Shigeoka and Nakano, "Characterization and molecular properties of 2-oxoglutarate decarboxylase from Euglena gracilis," Arch. Biochem. Biophys. 288:22-28 (1991).
Shimoyama et al., "MmcBC in Pelotomaculum thermopropionicum represents a novel group of prokaryotic fumarases," FEMS Microbiol Lett. 270(2):207-213 (2007).
Shingler et al., "Nucleotide sequence and functional analysis of the complete phenol/3,4-dimethylphenol catabolic pathway of Pseudomonas sp. strain CF600," J. Bacteriol. 174(3):711-724 (1992).
Sibilli et al., "Two regions of the bifunctional protein aspartokinase I-homoserine dehydrogenase I are connected by a short hinge," J. Biol. Chem. 256 (20):10228-10230 (1981).
Sieber et al., "Libraries of hybrid proteins from distantly related sequences," Nat. Biotechnol. 19:456-460 (2001).
Siegert et al., "Exchanging the substrate specificities of pyruvate decarboxylase from Zymomonas mobilis and benzoylformate decarboxylase from Pseudomonas putida," Protein. Eng. Des. Sel. 18:345-357 (2005).
Sinclair et al., Purification and characterization of the branched chain α-ketoacid dehydrogenase complex from Saccharomyces cerevisiae, Biochem. Mol. Biol. Int. 31(5):911-922 (1993).
Sjöström et al., "Purification and characterisation of a plasminogen-binding protein from Haemophilus influenzae. Sequence determination reveals identity with aspartase," Biochim. Biophys. Acta. 1324(2):182-190 (1997).
Smit et al., "Identification, cloning and characterization of Lactococcus lactis branched-chain α-keto acid decarboxylase involved in flavor formation," Appl. Environ. Microbiol. 71:303-311 (2005).
Smith et al., "Fumarate metabolism and the microaerophily of Campylobacter species," Int. J. Biochem. Cell Biol. 31(9):961-975 (1999).
Soda and Misono,"L-Lysine:α-ketoglutarate aminotransferase. II. Purification, crystallization, and properties," J. Bacteriol. 7:4110-4119 (1968).
Söhling and Gottschalk, "Molecular analysis of the anaerobic succinate degradation pathway in Clostridium kluyveri," J. Bacteriol. 178:871-880 (1996).
Stanley et al., "Expression and stereochemical and isotope effect studies of active 4-oxalocrotonate decarboxylase," Biochemistry 39(12):3514 (2000).
Starnes et al., "Threonine-sensitive aspartokinase-homoserine dehydrogenase complex, amino acid composition, molecular weight, and subunit composition of the complex," Biochemistry 11:677-687 (1973).
Steinbüchel and Schlegel, "NAD-linked L(+)-lactate dehydrogenase from the strict aerobe alcaligenes eutrophus. 2. Kinetic properties and inhibition by oxaloacetate," Eur. J. Biochem. 130(2):329-334 (1983).
Stemmer, "DNA shuffling by random fragmentation and reassembly: in vitro recombination for molecular evolution," Proc. Natl. Acad. Sci. USA 91:10747-10751 (1994).
Stemmer, "Rapid evolution of a protein in vitro by DNA shuffling," Nature 370:389-391 (1994).
Stoyan et al., "Cloning, sequencing and overexpression of the leucine dehydrogenase gene from Bacillus cereus," J. Biotechnol. 54:77-80 (1997).
Strauss and Fuchs, "Enzymes of a novel autotrophic CO2 fixation pathway in the phototrophic bacterium Chloroflexus aurantiacus, the 3-hydroxypropionate cycle," Eur. J. Biochem. 215:633-643 (1993).
Suda et al., "Purification and properties of α-ketoadipate reductase, a newly discovered enzyme from human placenta," Arch. Biochem. Biophys. 176(2):610-620 (1976).
Suda et al., "Subcellular localization and tissue distribution of a-ketoadipate reduction and oxidation in the rat," Biochem. Biophys. Res. Commun. 77(2):586-591 (1977).
Sulzenbacher et al., "Crystal structure of E. coli alcohol dehydrogenase YqhD: evidence of a covalently modified NADP Coenzyme," J. Mol. Biol. 342(2):489-502 (2004).
Takagi et al, "Purification, crystallization, and molecular properties of aspartase from Pseudomonas fluorescens," J. Biochem. 96(2):545-552 (1984).
Takagi et al., "Isolation of a versatile Serratia marcescens mutant as a host and molecular cloning of the aspartase gene," J. Bacteriol. 161:1-6 (1985).
Takahashi and Yamada, "Metabolic pathways for cytoxic and end product formation from glutamate- and aspartate-containing peptides by Porphyromonas gingivalis," J. Bacteriol. 182:4704-4710 (2000).
Takatsuka et al., "Identification of the amino acid residues conferring substrate specificity upon Selenomonas ruminantium lysine decarboxylase," Bioxci. Biotechnol. Biochem. 63:1843-1846 (1999).
Tanaka et al., "Lysine decarboxylase of Vibrio parahaemolyticus: kinetics of transcription and role in acid resistance," J. Appl. Microbiol. 104:1283-1293 (2008).
Tani et al., "Thermostable NADP+-dependent medium-chain alcohol dehydrogenase from Acinetobacter sp. strain M-1: purification

(56) References Cited

OTHER PUBLICATIONS and characterization and gene expression in *Escherichia coli*," Appl. Environ. Microbiol. 66(12):5231-5235 (2000).
Tanizawa et al., "The primary structure of thermostable D-amino acid aminotransferase from a thermophilic *Bacillus* species and its correlation with L-amino acid aminotransferases," J. Biol. Chem. 264(5):2450-2454 (1989).
Taylor and Fotheringham, "Nucleotide sequence of the Bacillus licheniformis ATCC 10716 dat gene and comparison of the predicted amino acid sequence with thos of other bacterial species," Biochim. Biophys. Acta 1350(1):38-40 (1997).
Ter Schure et al., "Pyruvate decarboxylase catalyzes decarboxylation of branched-chain 2-oxo acids but is not essential for fusel alcohol production by *Saccharomyces cerevisiae*," Appl. Environ. Microbiol. 64:1303-1307 (1998).
Thauer, "Microbiology. A Fifth Pathway of Carbon Fixation," Science 318:1732-1733 (2007).
Tian et al., "Variant tricarboxylic acid cycle in *Mycobacterium tuberculosis*: identification of α-ketoglutarate decarboxylase," Proc. Natl. Acad. Sci. USA 102:10670-10675 (2005).
Tobin et al., "Localization of the Lysine ε-Aminotransferase (lat) and δ-Aminoadipyl)-L-Cysteinyl-D-Valine Synthetase (pcbAB) Genes from Streptomyces clavuligerus and Production of Lysine E-Aminotransferase Activity in *Escherichia coli*," J. Bacteriol. 173(19):6223-6229 (1991).
Toth et al., "The ald Gene, Encoding a Coenzyme A-Acylating Aldehyde Dehydrogenase, Distinguishes Clostridium beijerinckii and Two Other Solvent-Producing Clostridia from Clostridium acetobutylicum," App. Environ. Microbiol. 65(11):4973-4980 (1999).
Tseng et al., "Oxygen- and growth rate-dependent regulation of *Escherichia coli* fumarase (FumA, FumB, and BumC) activity," J. Bacteriol. 183(2):461-467 (2001).
Tsujimoto et al., "L-Lysine biosynthetic pathway of Methylophilus methylotrophus and construction of an L-Lysine producer," J. Biotechnol. 124:327-337 (2006).
Uchiyama et al., "Identification of the 4-Hydroxycinnamate Decarboxylase (PAD) Gene of Klebsiella oxytoca," Biosci. Biotechnol. Biochem. 72: 116-123 (2008).
Van der Voorhorst et al., "Genetic and biochemcial characterization of a short-chain alcohol dehydrogenase from the hyperthermophilic archaeon Pyrococcus furiosus," Eur. J. Biochem. 268:3062-3068 (2001).
Vernal et al., "Cloning and heterologous expression of a broad specificity aminotransferase of Leishmania mexicana promastigotes," FEMS Microbiol. Lett. 229:217-222 (2003).
Vernal et al., "Isolation partial characterization of a broad specificity aminotransferase from leishmania mexicana promastigotes," Mol. Biochem. Parasitol. 96:83-92 (1998).
Volkov et al., "Random chimeragenesis by heteroduplex recombination," Methods Enzymol. 328:456-463 (2000).
Volkov et al., "Recombination and chimeragenesis by in vitro heteroduplex formation and in vivo repair," Nucleic Acids Res. 27:e18 (1999).
Wakil et al., "Studies on the fatty acid oxidizing system of animal tissues. VI. β-Hydroxyacyl. Coenzyme A dehydrogenase," J. Biol. Chem. 207(2):631-638 (1954).
Walter et al., "Molecular characterization of two Clostridium acetobutylicum ATCC 824 butanol dehydrogenase isozyme genes," J. Bacteriol. 174(22):7149-7158 (1992).
Wang and Barker, "Purification and Properties of L-citramalate hydrolase," J. Biol. Chem. 244(10):2516-2526 (1969).

Ward et al., "Molecular analysis of the rele of two aromatic aminotransferases and a broad-specificity aminotransferase in the aromatic amino acitd metabolism of Pyococcus furiosus," Archaea 1:133-141 (2002).
Weaver, "Structure of free fumarase C from *Escherichia coli*," Acta. Crystallogr. D. Biol. Crystallogr. 61(Pt 10):1395-1401 (2005).
Whalen and Berg, "Analysis of an avtA::Mu d1(Ap lac) Mutant: Metabolic Role of Transaminase C," J. Bacteriol. 150(2):739-746 (1982).
Whalen and Berg, "Gratuitous repression of avtA in *Escherichia coli* and *Salmonella typhimurium*," J. Bacteriol. 158(2):571-574 (1984).
Wilkie and Warren, "Recombinant expression, purification, and characterization of three isoenzymes of aspartate aminotransferase from *Arabidopsis thaliana*," Protein Expr. Purif. 12:381-389 (1998).
Wilks et al., "A specific, Highly Active Malate Dehydrogenase by Redesign of a Lactate Dehydrogenase Framework," Science 242:1541-1544 (1988).
Wilks et al., "Design of a Specific Phenyllactate Dehydrogenase by Peptide Loop Exchange on the Bacillus stearothermophilus Lactate Dehydrogenase Framework," Biochemistry 31:7802-7806 (1992).
Wilks et al., "Designs for a Broad Substrate Specificity Keto Acid Dehydrogenase," Biochemistry 29:8587-8591 (1990).
Willke and Vorlop, "Biotechnological production of itaconic acid," Appl. Microbiol. Biotechnol. 56(3-4):289-295 (2001).
Wolff and Kenealy, "Purification and characterization of the oxygen-sensitive 4-hydroxybutanoate dehydrogenase from Clostridium kluyveri," Protein Expr. Purif. 6:206-212 (1995).
Wong et al., "Sequence saturation mutagenesis with tunable mutation frequencies," Anal. Biochem. 341:187-189 (2005).
Wong et al., "Transversion-enriched sequence saturation mutagenesis (SeSaM-Tv+): a random mutagenesis method with consecutive nucleotide exchanges that complements the bias of error-prone PCR," Biotechnol. J. 3:74-82 (2008).
Woods et al., "Two biochemically distinct classes of fumarase in *Escherichia coli*," Biochim. Biophys. Acta 954(1):14-26 (1988).
Yagi et al., "Aspartate: 2-oxoglutarate aminotransferase from bakers' yeast: crystallization and characterization," J. Biochem. 92(1):35-43 (1982).
Yagi et al., "Crystallization and properties of aspartate aminotransferase from *Escherichia coli* B," FEBS Lett. 100(1):81-84 (1979).
Yagi et al., "Glutamate-aspartate transaminase from microorganisms," Methods Enzymol. 113:83-89.
Yamamoto et al., "Synthesis of (R)-1,3-butanediol by enantioselective oxidation using whole recombinant *Escherichia coli* cells expressing (S)-specific secondary alcohol dehydrogenase," Biosci. Biotechnol. Biochem., 66(4):925-927 (2002).
Yang et al., "Aspartate Dehydrogenase, a Novel Enzyme Identified from Structural and Functional Studies of TM1643," J. Biol. Chem. 278(10):8804-8808 (2003).
Yano et al., "Directed evolution of an aspartate aminotransferase with new substrate specificities," Proc. Natl. Acad. Sci. USA 95:5511-5515 (1998).
Youngleson et al., "Homology between hydroxybutyryl and hydroxyacyl Coenzyme A dehydrogenase enzymes from Clostridium acetobutylicum fermentation and vertebrate fatty acid β-oxidation pathways," J. Bacteriol. 171(12):6800-6807 (1989).
Zhang et al., "Directed evolution of a fucosidase from a galactosidase by DNA shuffling and screening," Proc. Natl. Acad. Sci. USA 94(9):4504-4509 (1997).
Zhao et al., "Molecular evolution by staggered extension process (StEP) in vitro recombination," Nat. Biotechnol. 16:258-261 (1998).

* cited by examiner

US 11,180,780 B2

ORGANISMS FOR THE PRODUCTION OF 1,3-BUTANEDIOL

STATEMENT OF RELATED APPLICATIONS

This application is a continuation of U.S. Non-provisional application Ser. No. 14/673,600, filed Mar. 30, 2015, which is a continuation of U.S. Non-provisional application Ser. No. 12/772,114, filed Apr. 30, 2010, now U.S. Pat. No. 9,017,983, which claims the benefit of priority of U.S. Provisional Application No. 61/174,473, filed Apr. 30, 2009, the entire contents of which are incorporated herein by reference.

BACKGROUND OF THE INVENTION

The present invention relates generally to biosynthetic processes and organisms capable of producing organic compounds. More specifically, the invention relates to non-naturally occurring organisms that can produce the commodity chemical 1,3-butanediol.

1,3-butanediol (1,3-BDO) is a four carbon diol traditionally produced from acetylene via its hydration. The resulting acetaldehyde is then converted to 3-hydroxybutyraldehdye which is subsequently reduced to form 1,3-BDO. In more recent years, acetylene has been replaced by the less expensive ethylene as a source of acetaldehyde. 1,3-BDO is commonly used as an organic solvent for food flavoring agents. It is also used as a co-monomer for polyurethane and polyester resins and is widely employed as a hypoglycaemic agent. Optically active 1,3-BDO is a useful starting material for the synthesis of biologically active compounds and liquid crystals. A substantial commercial use of 1,3-butanediol is subsequent dehydration to afford 1,3-butadiene (Ichikawa et al., *J. of Molecular Catalysis A—Chemical*, 256:106-112 (2006); Ichikawa et al., *J. of Molecular Catalysis A—Chemical*, 231:181-189 (2005)), a 25 billion lb/yr petrochemical used to manufacture synthetic rubbers (e.g., tires), latex, and resins. The reliance on petroleum based feedstocks for either acetylene or ethylene warrants the development of a renewable feedstock based route to 1,3-butanediol and to butadiene.

Thus, there exists a need to develop microorganisms and methods of their use to produce 1,3-BDO. The present invention satisfies this need and provides related advantages as well.

SUMMARY OF THE INVENTION

In some embodiments, the present invention is directed to a non-naturally occurring microbial organism that includes a microbial organism having a 1,3-butanediol (1,3-BDO) pathway having at least one exogenous nucleic acid encoding a 1,3-BDO pathway enzyme expressed in a sufficient amount to produce 1,3-BDO. The 1,3-BDO pathway includes an enzyme selected from the group consisting of a 2-amino-4-ketopentanoate (AKP) thiolase, an AKP dehydrogenase, a 2-amino-4-hydroxypentanoate aminotransferase, a 2-amino-4-hydroxypentanoate oxidoreductase (deaminating), a 2-oxo-4-hydroxypentanoate decarboxylase, a 3-hydroxybutyraldehyde reductase, an AKP aminotransferase, an AKP oxidoreductase (deaminating), a 2,4-dioxopentanoate decarboxylase, a 3-oxobutyraldehyde reductase (ketone reducing), a 3-oxobutyraldehyde reductase (aldehyde reducing), a 4-hydroxy-2-butanone reductase, an AKP decarboxylase, a 4-aminobutan-2-one aminotransferase, a 4-aminobutan-2-one oxidoreductase (deaminating), a 4-aminobutan-2-one ammonia-lyase, a butenone hydratase, an AKP ammonia-lyase, an acetylacrylate decarboxylase, an acetoacetyl-CoA reductase (CoA-dependent, aldehyde forming), an acetoacetyl-CoA reductase (CoA-dependent, alcohol forming), an acetoacetyl-CoA reductase (ketone reducing), a 3-hydroxybutyryl-CoA reductase (aldehyde forming), a 3-hydroxybutyryl-CoA reductase (alcohol forming), a 4-hydroxybutyryl-CoA dehydratase, and a crotonase.

In some embodiments, the present invention is directed to a method for producing 1,3-BDO that includes culturing such a non-naturally occurring microbial organism, under conditions and for a sufficient period of time to produce 1,3-BDO.

DETAILED DESCRIPTION OF THE INVENTION

This invention is directed, in part, to non-naturally occurring microorganisms that express genes encoding enzymes that catalyze 1,3-butanediol (1,3-BDO) production. Pathways for the production of 1,3-butanediol disclosed herein are based on three precursors: (i) D-alanine, (ii) acetoacetyl-CoA, and (iii) 4-hydroxybutyryl-CoA. Successfully engineering these pathways entails identifying an appropriate set of enzymes with sufficient activity and specificity, cloning their corresponding genes into a production host, optimizing fermentation conditions, and assaying for product formation following fermentation.

Figure 1:
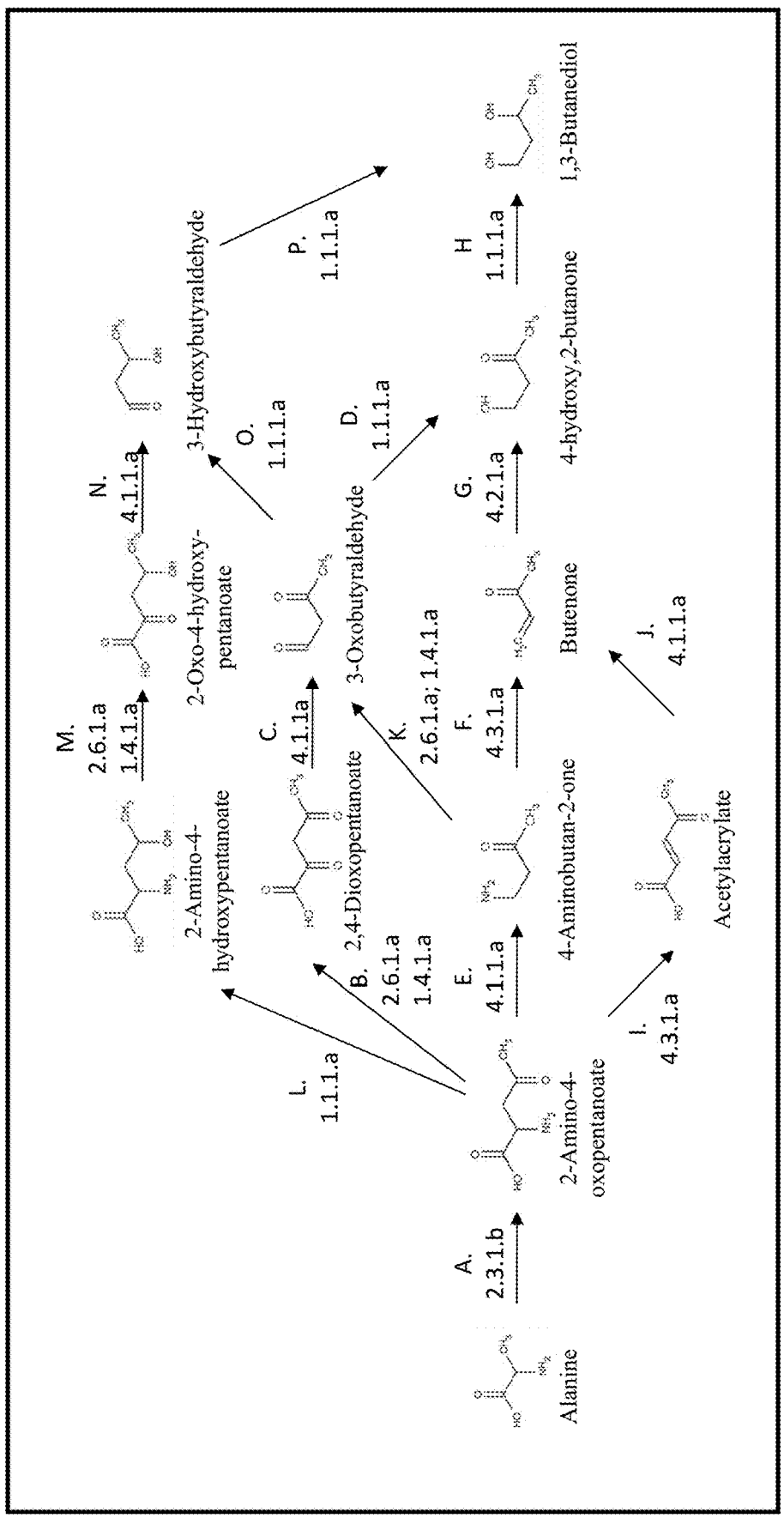
FIG. 1 shows pathways to 1,3-BDO from alanine. Enzymes are: A) AKP thiolase, B) AKP aminotransferase or AKP oxidoreductase (deaminating), C) 2,4-dioxopentanoate decarboxylase, D) 3-oxobutyraldehyde reductase (aldehyde reducing), E) AKP decarboxylase, F) 4-aminobutan-2-one ammonia-lyase, G) Butenone hydratase, H) 4-hydroxy,2-butanone reductase, I) AKP ammonia-lyase, J) acetylacrylate decarboxylase, K) 4-aminobutan-2-one aminotransferase or 4-aminobutan-2-one oxidoreductase (deaminating), L) AKP dehydrogenase, M) 2-amino-4-hydroxypentanoate aminotransferase or 2-amino-4-hydroxypentanoate oxidoreductase (deaminating), N) 2-oxo-4-hydroxypentanoate decarboxylase, O) 3-oxobutyraldehyde reductase (ketone reducing), and P) 3-hydroxybutyraldehdye reductase.

The conversion of alanine to 1,3-BDO can be accomplished by a number of pathways in about five enzymatic steps as shown in FIG. 1. In the first step of all pathways (Step A), alanine and acetyl-CoA are combined by 2-amino-4-ketopentanoate thiolase, a highly selective enzyme. The product of this reaction, 2-amino-4-oxopentanoate (AKP) can then be transaminated, reduced, decarboxylated or deaminated as shown in FIG. 1. Further synthetic steps for the production of 1,3-BDO are discussed in detail below. The theoretical yield of 1,3-BDO from each of these pathways is calculated to be about 1.09 mole/mole of glucose consumed.

Figure 2:
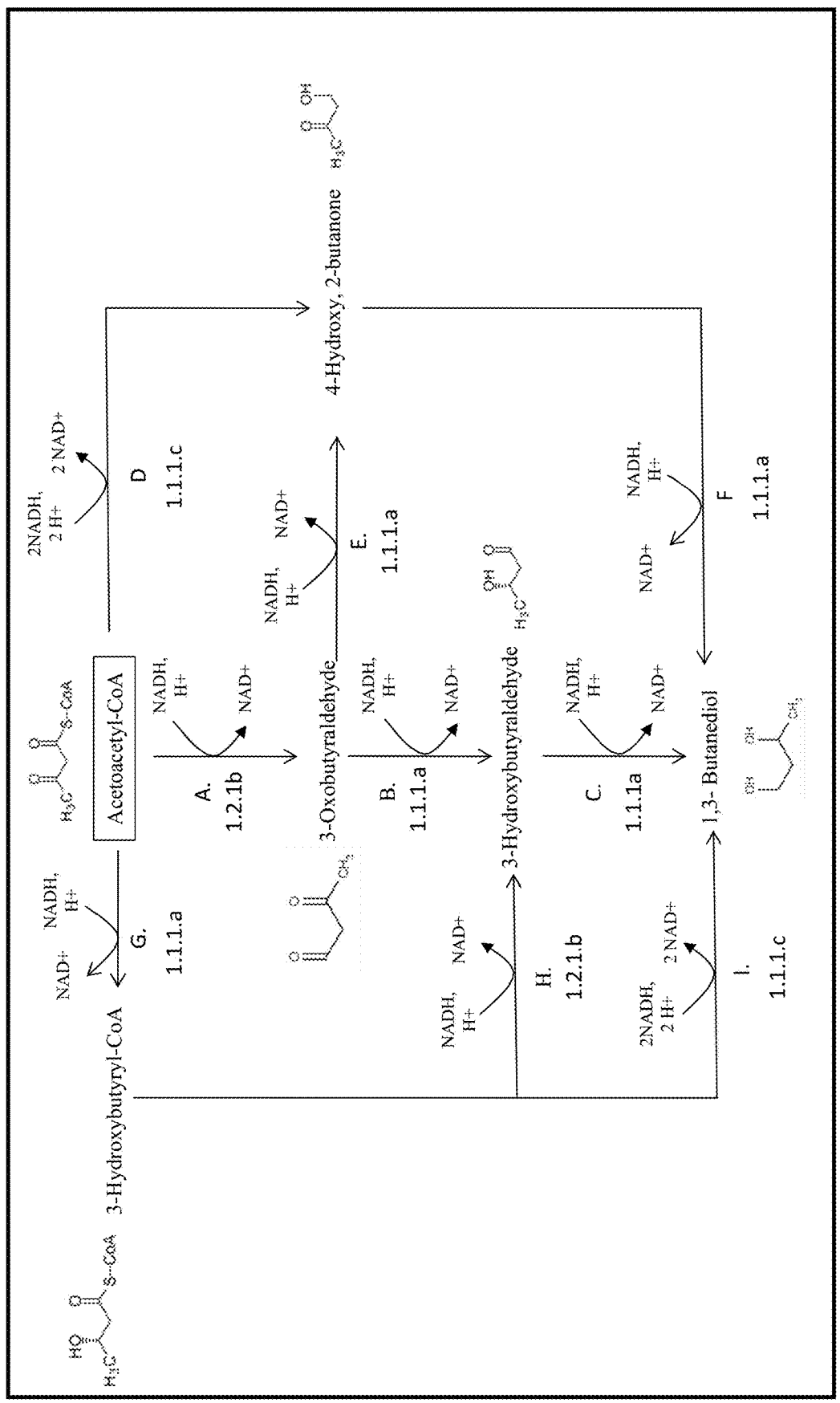
FIG. 2 shows pathways from acetoacetyl-CoA to 1,3-butanediol. Enzymes are: A) acetoacetyl-CoA reductase (CoA-dependent, aldehyde forming), B) 3-oxobutyraldehyde reductase (ketone reducing), C) 3-hydroxybutyraldehyde reductase, D) acetoacetyl-CoA reductase (CoA-dependent, alcohol forming), E) 3-oxobutyraldehyde reductase (aldehyde reducing), F) 4-hydroxy,2-butanone reductase, G) acetoacetyl-CoA reductase (ketone reducing), H) 3-hydroxybutyryl-CoA reductase (aldehyde forming), and I) 3-hydroxybutyryl-CoA reductase (alcohol forming).

FIG. 2 outlines multiple routes for producing 1,3-BDO from acetoacetyl-CoA. Each of these pathways from acetoacetyl-CoA to 1,3-BDO utilizes three reducing equivalents and provides a theoretical yield of 1 mole of 1,3-BDO per mole of glucose consumed. Other carbon substrates such as syngas can also be used for the production of acetoacetyl-CoA. Gasification of glucose to form syngas will result in the maximum theoretical yield of 1.09 moles of 1,3-BDO per mole of glucose consumed, assuming that 6 moles of CO and 6 moles of $H_2$ are obtained from glucose

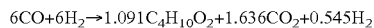

$$6CO+6H_2 \rightarrow 1.091C_4H_{10}O_2+1.636CO_2+0.545H_2$$

Figure 3:
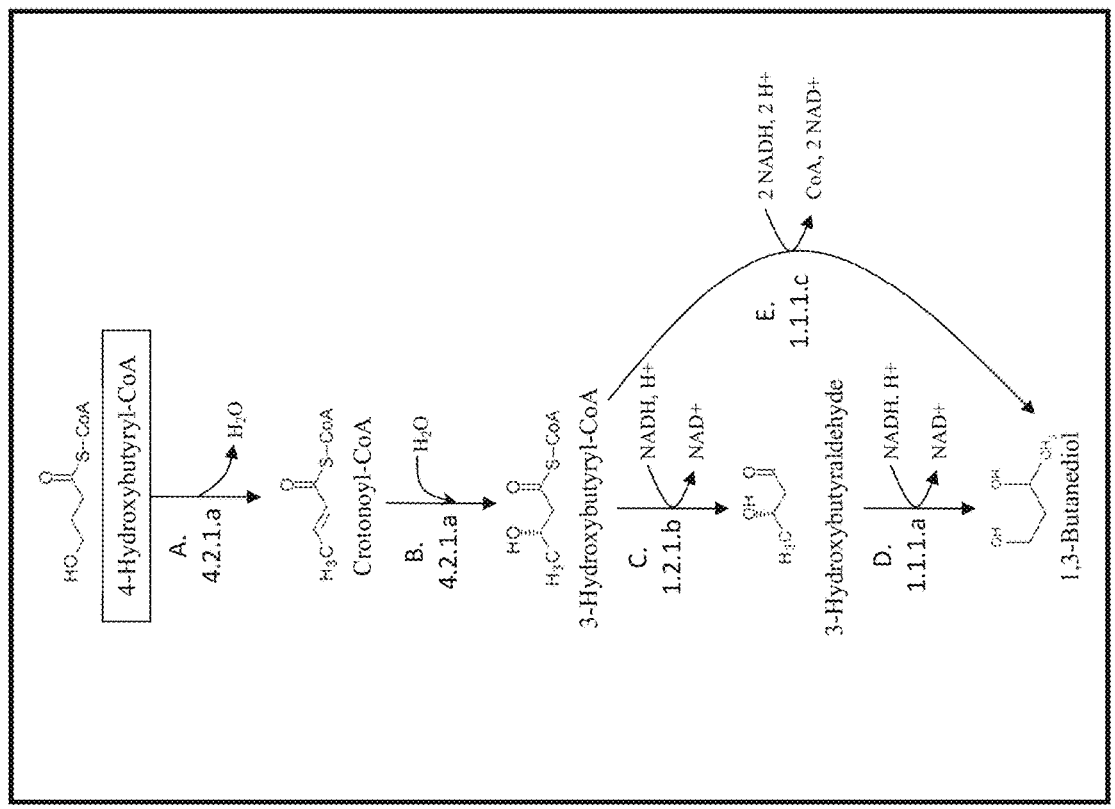
FIG. 3 shows pathways from 4-hydroxybutyryl-CoA to 1,3-butanediol. Enzymes are: A) 4-hydroxybutyryl-CoA dehydratase, B) crotonase, C) 3-hydroxybutyryl-CoA reductase (aldehyde forming), D) 3-hydroxybutyraldehyde reductase, and E) 3-hydroxybutyryl-CoA reductase (alcohol forming).

4-Hydroxybutyryl-CoA is an important starting metabolite from which a number of industrially useful compounds can be made, including 1,3-BDO as shown in FIG. 3. Although 4-hydroxybutyryl-CoA is not a highly common central metabolite, methods for engineering strains that synthesize 4-hydroxybutyryl-CoA have been described previously by Applicants in U.S. Patent Application No. 2009/0075351. The 4-hydroxybutyryl-CoA to 1,3-butanediol pathway has a theoretical yield of 1.09 mol/mol product yield assuming glucose as the carbohydrate feedstock.

This invention is also directed, in part, to methods for producing 1,3-BDO through culturing of these non-naturally occurring microbial organisms. Dehydration of 1,3-BDO produced by the organisms and methods described herein, provides an opportunity to produce renewable butadiene in small end-use facilities obviating the need to transport this flammable and reactive chemical.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a 1,3-butanediol biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 1,3-BDO biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the present invention provides a non-naturally occurring microbial organism that includes a microbial organism having a 1,3-butanediol (1,3-BDO) pathway with at least one exogenous nucleic acid encoding a 1,3-BDO pathway enzyme expressed in a sufficient amount to produce 1,3-BDO. The 1,3-BDO pathway includes an enzyme selected from the group consisting of a 2-amino-4-ketopentanoate (AKP) thiolase, an AKP dehydrogenase, a 2-amino-4-hydroxypentanoate aminotransferase, a 2-amino-4-hydroxypentanoate oxidoreductase (deaminating), a 2-oxo-4-hydroxypentanoate decarboxylase, a 3-hydroxybutyraldehyde reductase, an AKP aminotransferase, an AKP oxidoreductase (deaminating), a 2,4-dioxopentanoate decarboxylase, a 3-oxobutyraldehyde reductase (ketone reducing), a 3-oxobutyraldehyde reductase (aldehyde reducing), a 4-hydroxy-2-butanone reductase, an AKP decarboxylase, a 4-aminobutan-2-one aminotransferase, a 4-aminobutan-2-one oxidoreductase (deaminating), a 4-aminobutan-2-one ammonia-lyase, a butenone hydratase, an AKP ammonia-lyase, an acetylacrylate decarboxylase, an acetoacetyl-CoA reductase (CoA-dependent, aldehyde forming), an acetoacetyl-CoA reductase (CoA-dependent, alcohol forming), an acetoacetyl-CoA reductase (ketone reducing), a 3-hydroxybutyryl-CoA reductase (aldehyde forming), a 3-hydroxybutyryl-CoA reductase (alcohol forming), a 4-hydroxybutyryl-CoA dehydratase, and a crotonase.

Any combination and any number of the aforementioned enzymes can be introduced into a host microbial organism to complete a 1,3-BDO pathway, as exemplified in FIGS. 1-3.

For example, the non-naturally occurring microbial organism can include one, two, three, four, five, up to all of the nucleic acids in a 1,3-BDO pathway, each nucleic acid encoding a 1,3-BDO pathway enzyme. Such nucleic acids can include heterologous nucleic acids, additional copies of existing genes, and gene regulatory elements, as explained further below. The pathways of the non-naturally occurring microbial organisms of the invention are also suitably engineered to be cultured in a substantially anaerobic culture medium.

In some embodiments, the non-naturally occurring microbial organisms having a 1,3-BDO pathway include a set of 1,3-BDO pathway enzymes. A set of 1,3-BDO pathway enzymes represents a group of enzymes that can convert alanine, acetoacetyl-CoA, or 4-hydroxybutyryl-CoA to 1,3-BDO, as show in FIGS. 1-3. Exemplary sets of 1,3-BDO pathway enzymes to convert alanine to 1,3-BDO, according to FIG. 1 include (a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase; (b) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase; (c) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase; (d) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase; (e) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase; (f) (1) a 2-amino-4-ketopentanoate (AKP) thiolase; (2) an AKP decarboxylase; (3) a 4-aminobutan-2-one ammonia-lyase; (4) a butenone hydratase; and (5) a 4-hydroxy-2-butanone reductase; and (g) (1) a 2-amino-4-ketopentanoate (AKP) thiolase; (2) an AKP ammonia-lyase; (3) an acetylacrylate decarboxylase; (4) a butenone hydratase; and (5) a 4-hydroxy-2-butanone reductase;

Exemplary sets of 1,3-BDO pathway enzymes to convert acetoacetyl-CoA to 1,3-BDO, according to FIG. 2 include (h) (1) an acetoacetyl-CoA reductase (CoA-dependent, aldehyde forming); (2) a 3-oxobutyraldehyde reductase (ketone reducing); and (3) a 3-hydroxybutyraldehyde reductase; (i) (1) an acetoacetyl-CoA reductase (CoA dependent, alcohol forming) and (2) a 4-hydroxy-2-butanone reductase; (j) (1) an acetoacetyl-CoA reductase (CoA-dependent, aldehyde forming); (2) a 3-oxobutyraldehyde reductase (aldehyde reducing); and (3) a 4-hydroxy-2-butanone reductase; (k) (1) an acetoacetyl-CoA reductase (ketone reducing) and (2) a 3-hydroxybutyryl-CoA reductase (alcohol forming); and (1) (1) an acetoacetyl-CoA reductase (ketone reducing); (2) a 3-hydroxybutyryl-CoA reductase (aldehyde forming); and (3) a 3-hydroxybutyraldehyde reductase;

Exemplary sets of 1,3-BDO pathway enzymes to convert 4-hydroxybutyryl-CoA to 1,3-BDO, according to FIG. 3 include (m) (1) a 4-hydroxybutyryl-CoA dehydratase; (2) a crotonase; and (3) a 3-hydroxybutyryl-CoA reductase (alcohol forming); and (n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase.

The conversion of alanine to 1,3-BDO can be accomplished by a number of pathways involving about five enzymatic steps as shown in FIG. 1. In the first step of all pathways (Step A), alanine and acetyl-CoA are combined by 2-amino-4-ketopentanoate thiolase, a highly selective enzyme. The product of this reaction, 2-amino-4-oxopentanoate (AKP) can then be transaminated, reduced, decarboxylated or deaminated as shown in FIG. 1.

In one route, AKP converted to 2,4-dioxopentanoate, a 2-keto acid similar in structure to alpha-ketoglutarate, by an aminotransferase or deaminating oxidoreductase (Step B). 2,4-Dioxopentanoate is then converted to 3-oxobutyraldehyde by a 2-ketoacid decarboxylase (Step C). Reduction of the ketone and aldehyde groups to their corresponding alcohols yields 1,3-butanediol. These reductions can occur in either order to form the intermediates 3-hydroxybutyraldehyde (Steps O and P) or 4-hydroxy,2-butanone (Steps D and H).

In another route, the 4-oxo group of AKP is first reduced to a secondary alcohol by AKP dehydrogenase (Step L). The product, 2-amino-4-hydroxypentanoate, is then converted to 2-oxo-4-hydroxypentanoate (Step M). The resulting 2-ketoacid is decarboxylated to 3-hydroxybutyraldehyde (Step N). In the final step of this route, the aldehyde of 3-hydroxybutyraldehyde is reduced to a primary alcohol by 3-hydroxybutyraldehyde reductase, forming 1,3-butanediol (Step P).

Yet another route involves decarboxylation of AKP by an amino acid decarboxylase (Step E). The decarboxylation product, 4-aminobutan-2-one, can either be transaminated or oxidatively deaminated to 3-oxobutyraldehyde (Step K) or deaminated to butenone (Step F). When 3-oxobutyraldehyde is formed, two alcohol-forming reduction steps are used to form 1,3-butanediol, as described previously (Steps O and P, or Steps D and H). The deamination product, butenone, is then hydrolyzed to 4-hydroxy,2-butanone (Step G), which is reduced to 1,3-butanediol by 4-hydroxy-2-butanone reductase (Step H).

Yet another route involves the deamination of AKP to acetylacrylate (Step I). Acetylacrylate is decarboxylated to butenone (Step J), which is then converted to 1,3-butandiol by butenone hydratase (Step G) and 4-hydroxy,2-butanone reductase (Step H).

Based on the routes described above for the production 1,3-BDO from alanine, in some embodiments, the non-naturally occurring microbial organism has a set of 1,3-BDO pathway enzymes that includes (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In other embodiments non-naturally occurring microbial organism has a set of 1,3-BDO pathway enzymes that includes (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In still other embodiments, the non-naturally occurring microbial organism has a set of 1,3-BDO pathway enzymes that includes (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In yet further embodiments, the non-naturally occurring microbial organism has a set of 1,3-BDO pathway enzymes that includes (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In yet still further embodiments, the non-naturally occurring microbial organism has a set of 1,3-BDO pathway enzymes that includes (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In still further embodiments, the non-naturally occurring microbial organism has a set of 1,3-BDO pathway enzymes that includes (1) a 2-amino-4-ketopentanoate (AKP) thiolase; (2) an AKP decarboxylase; (3) a 4-aminobutan-2-one ammonia-lyase; (4) a butenone hydratase; and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In yet still further embodiments, the non-naturally occurring microbial organism has a set of 1,3-BDO pathway enzymes that includes (1) a 2-amino-4-ketopentanoate (AKP) thiolase; (2) an AKP ammonia-lyase; (3) a an acetylacrylate decarboxylase; (4) a butenone hydratase; and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

FIG. 2 outlines multiple routes for producing 1,3-butanediol from acetoacetyl-CoA. One route through steps A, B and C utilizes (i) CoA-dependent, aldehyde forming acetoacetyl-CoA reductase to convert acetoacetyl-CoA into 3-oxobutyraldehyde (FIG. 2, Step A), (ii) 3-oxobutyraldehyde reductase to reduce 3-oxobutyraldehyde to 3-hydroxybutyraldehyde (FIG. 2, Step B), and (iii) finally, 3-hydroxybutyraldehyde reductase to form 1,3-butanediol (FIG. 2, Step C).

Alternatively, acetoacetyl-CoA can be reduced via the aldehyde forming acetoacetyl-CoA reductase to form 4-hydroxy,2-butanone (FIG. 2, Step D). 4-hydroxy,2-butanone can also be formed by the reduction of 3-oxobutyraldehyde by the aldehyde reducing 3-oxobutyraldehyde reductase (FIG. 2, Step E). Eventually, 4-hydroxy,2-butanone can be reduced to form 1,3-BDO by 4-hydroxy-2-butanone reductase (FIG. 2, Step F).

Yet another set of 1,3-BDO forming routes rely on the reduction of acetoacetyl-CoA to 3-hydroxybutyryl-CoA by the ketone reducing acetoacetyl-CoA reductase (FIG. 2, Step G). This enzyme reduces the ketone function in acetoacetyl-CoA to a hydroxyl group. 3-hydroxybutyryl-CoA can be reduced by the bifunctional alcohol-forming 3-hydroxybutyryl-CoA reductase to form 1,3-butanediol (FIG. 2, Step I). Alternatively, it can first be reduced to 3-hydroxybutyraldehyde via the aldehyde forming 3-hydroxybutyryl-CoA reductase (Step H) and 3-hydroxybutyraldehyde can then be reduced as shown in Step C.

Based on the routes described above for the production 1,3-BDO from acetoacetyl-CoA, in some embodiments, the non-naturally occurring microbial organism has a set of 1,3-BDO pathway enzymes that includes (1) an acetoacetyl-CoA reductase (CoA-dependent, aldehyde forming); (2) a 3-oxobutyraldehyde reductase (ketone reducing); and (3) a 3-hydroxybutyraldehyde reductase. Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

In other embodiments, the non-naturally occurring microbial organism has a set of 1,3-BDO pathway enzymes that includes (1) an acetoacetyl-CoA reductase (CoA dependent, alcohol forming) and (2) a 4-hydroxy-2-butanone reductase. Any number of nucleic acids encoding these enzymes can be introduced into a host microbial organism including one or both of the nucleic acids that encode these enzymes. Where one exogenous nucleic acid is introduced, such a nucleic acid can be either of the two nucleic acids.

In further embodiments, the non-naturally occurring microbial organism has a set of 1,3-BDO pathway enzymes that includes (1) an acetoacetyl-CoA reductase (CoA-dependent, aldehyde forming); (2) a 3-oxobutyraldehyde reductase (aldehyde reducing); and (3) a 4-hydroxy-2-butanone reductase. Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

In yet further embodiments, the non-naturally occurring microbial organism has a set of 1,3-BDO pathway enzymes that includes (1) an acetoacetyl-CoA reductase (ketone reducing) and (2) a 3-hydroxybutyryl-CoA reductase (alcohol forming). Any number of nucleic acids encoding these enzymes can be introduced into a host microbial organism including one or both of the nucleic acids that encode these enzymes. Where one exogenous nucleic acid is introduced, such a nucleic acid can be either of the two nucleic acids.

In still further embodiments, the non-naturally occurring microbial organism has a set of 1,3-BDO pathway enzymes that includes (1) an acetoacetyl-CoA reductase (ketone reducing); (2) a 3-hydroxybutyryl-CoA reductase (aldehyde forming); and (3) a 3-hydroxybutyraldehyde reductase. Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

4-hydroxybutyryl-CoA is an important starting metabolite from which a number of industrially useful compounds can be made. Although 4-hydroxybutyryl-CoA is not a highly common central metabolite, methods for engineering strains that synthesize 4-hydroxybutyryl-CoA have been described in Burk et al. (US 20090075351). An exemplary method involves synthesizing 4-hydroxybutyryl-CoA from succinyl-CoA by employing genes encoding succinic semialdehyde dehydrogenase (CoA-dependent), 4-hydroxybutyrate dehydrogenase, 4-hydroxybutyrate kinase, and phosphotransbutyrylase activities.

The first step in the pathway involves the dehydration of 4-hydroxybutyryl-CoA (Step A, FIG. 3) followed by the hydration of crotonoyl-CoA to form 3-hydroxybutyryl-CoA (Step B). 3-hydroxybutyryl-CoA then undergoes two reduction steps to form 1,3-butanediol carried out by either two enzymes (Steps C and D) or a single dual-function enzyme (Step E).

Thus, in some embodiments, the non-naturally occurring microbial organism has a set of 1,3-BDO pathway enzymes that includes (1) a 4-hydroxybutyryl-CoA dehydratase; (2) a crotonase; and (3) a 3-hydroxybutyryl-CoA reductase (alcohol forming). Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

In other embodiments, the non-naturally occurring microbial organism has a set of 1,3-BDO pathway enzymes that includes (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase. Any number of nucleic acids encoding these enzymes can be introduced into a host microbial organism including one, two, three up to all four of the nucleic acids that encode these enzymes. Where one, two, or three exogenous nucleic acids are introduced, such nucleic acids can be any permutation of the four nucleic acids.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 2-amino-4-hydroxypentanoate, 2-amino-4-hydroxypentanoate to 2-oxo-4-hydroxypentanoate, 2-oxo-4-hydroxypentanoate to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 2,4-dioxopentanoate, 2,4-dioxopentanoate to 3-oxobutyraldehyde, 3-oxobutyraldehyde to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 2,4-dioxopentanoate, 2,4-dioxopentanoate to 3-oxobutyraldehyde, 3-oxobutyraldehyde to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 4-aminobutan-2-one, 4-aminobutan-2-one to 3-oxobutyraldehyde, 3-oxobutyraldehyde to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 4-aminobutan-2-one, 4-aminobutan-2-one to 3-oxobutyraldehyde, 3-oxobutyraldehyde to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 4-aminobutan-2-one, 4-aminobutan-2-one to butenone, butenone to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to acetylacrylate, acetylacrylate to butenone, butenone to 4-hydroxy-2-butanone, and 4-hydroxy-2-butanone to 1,3-BDO.

Thus, the invention provides a non-naturally occurring microbial organism containing at least one exogenous nucleic acid encoding an enzyme or protein, where the enzyme or protein converts the substrates and products of a 1,3-BDO pathway converting alanine to 1,3-BDO, as exemplified by the pathways shown in FIG. 1.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-oxobutyraldehyde, 3-oxobutyraldehyde to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-oxobutyraldehyde, 3-oxobutyraldehyde to 3-hydroxybutryaldehyde, and 3-hydroxybutryaldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-hydroxybutyryl-CoA, 3-hydroxybutyryl-CoA to 3-hydroxybutryaldehyde, and 3-hydroxybutryaldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-hydroxybutyryl-CoA, and 3-hydroxybutyryl-CoA to 1,3-BDO.

Thus, the invention provides a non-naturally occurring microbial organism containing at least one exogenous nucleic acid encoding an enzyme or protein, where the enzyme or protein converts the substrates and products of a 1,3-BDO pathway converting acetoacetyl-CoA to 1,3-BDO, as exemplified by the pathways shown in FIG. 2.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of 4-hydroxybutyryl-CoA to crotonoyl-CoA, crotonoyl-CoA to 3-hydroxybutyryl-CoA, 3-hydroxybutyryl-CoA to 3-hydroxybutryaldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of 4-hydroxybutyryl-CoA to crotonoyl-CoA, crotonoyl-CoA to 3-hydroxybutyryl-CoA, and 3-hydroxybutyryl-CoA to 1,3-BDO.

Thus, the invention provides a non-naturally occurring microbial organism containing at least one exogenous nucleic acid encoding an enzyme or protein, where the enzyme or protein converts the substrates and products of a 1,3-BDO pathway, the pathway converting 4-hydroxybutyryl-CoA to 1,3-BDO, as exemplified by the pathways shown in FIG. 3.

Successfully engineering any of these pathways entails identifying an appropriate set of enzymes with sufficient activity and specificity, cloning their corresponding genes into a production host, optimizing fermentation conditions, and assaying for product formation following fermentation. To engineer a production host for the production of any of the aforementioned products, one or more exogenous DNA sequence(s) can be expressed in microorganisms. In addition, the microorganisms can have endogenous gene(s) functionally deleted. These modifications will enable the production of 1,3-BDO using renewable feedstocks.

Below, we describe a number of biochemically characterized genes capable of encoding enzymes that catalyze each of the steps shown in FIGS. 1, 2 and 3. Although we describe this method for *E. coli*, one skilled in the art can apply these teachings to essentially any other organism. Specifically, genes are listed that are native to *E. coli* in addition to genes in other organisms that can be applied to catalyze the appropriate transformations when properly cloned and expressed.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

All transformations depicted in FIGS. 1-3 fall into the 8 general categories of transformations shown in Table 1. Below is described a number of biochemically characterized genes in each category. Specifically listed are genes that can be applied to catalyze the appropriate transformations in FIGS. 1-3 when properly cloned and expressed. Exemplary genes for each of the steps in FIGS. 1-3 are provided further below in Tables 35-37.

Table 1 shows the enzyme types useful to convert common central metabolic intermediates into 1,3-butanediol. The first three digits of each label correspond to the first three Enzyme Commission number digits which denote the general type of transformation independent of substrate specificity.

TABLE 1

| LABEL | FUNCTION |
|---|---|
| 1.1.1.a | Oxidoreductase (ketone to hydroxyl or aldehyde to alcohol) |
| 1.1.1.c | Oxidoreductase (2 step, acyl-CoA to alcohol) |
| 1.2.1.b | Oxidoreductase (acyl-CoA to aldehyde) |
| 1.4.1.a | Oxidoreductase (deaminating) |
| 2.3.1.b | Acyltransferase |
| 2.6.1.a | Aminotransferase |
| 4.1.1.a | Carboxy-lyase |
| 4.2.1.a | Hydro-lyase |
| 4.3.1.a | Ammonia-lyase |

Numerous transformation in FIGS. 1, 2 and 3 fall into the category of oxidoreductases that reduce an aldehyde to alcohol. For example, Steps D and P in FIG. 1 catalyzed by 3-oxobutyraldehyde reductase (aldehyde reducing) and 3-hydroxybutyraldehyde reductase respectively fall into this category. Similarly, Steps C and E in FIG. 2 catalyzed by 3-hydroxybutyraldehyde reductase and 3-oxobutyraldehdye reductase (aldehyde reducing) respectively are also oxidoreductases that convert the aldehyde functionality to alcohol. Pathways in FIG. 3 involve oxidoreductases such as 3-hydroxybutyraldehdye reductase in Step D.

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.*, 66:5231-5235 (2000)), ADH2 from *Saccharomyces cerevisiae* (Atsumi et al., *Nature*, 451:86-89 (2008)), yqhD from *E. coli* which has preference for molecules longer than C3 (Sulzenbacher et al., *J. of Molecular Biology*, 342:489-502 (2004)), and bdh I and bdh II from *C. acetobutylicum* which converts butyraldehyde into butanol (Walter et al., *J. of Bacteriology*, 174:7149-7158 (1992)). The gene product of yqhD catalyzes the reduction of acetaldehyde, malondialdehyde, propionaldehyde, butyraldehyde, and acrolein using NADPH as the cofactor (Perez et al., *J. Biol. Chem.*, 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol*, 22:249-254 (1985)). Additional aldehyde reductase candidates are encoded by bdh in *C. saccharoperbutylacetonicum* and Cbei_1722, Cbei_2181 and Cbei_2421 in *C. beijerinckii*.

Data related to the sequences for each of these exemplary gene products can be found using the following GenBank accession numbers shown in Table 2.

TABLE 2

| Protein | GENBANK ID | GI NUMBER | ORGANISM |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

TABLE 2-continued

| Protein | GENBANK ID | GI NUMBER | ORGANISM |
|---|---|---|---|
| bdh | BAF45463.1 | 124221917 | Clostridium saccharoperbutylacetonicum |
| Cbei_1722 | YP_001308850 | 150016596 | Clostridium beijerinckii |
| Cbei_2181 | YP_001309304 | 150017050 | Clostridium beijerinckii |
| Cbei_2421 | YP_001309535 | 150017281 | Clostridium beijerinckii |

Enzymes exhibiting 3-hydroxybutyraldehyde reductase activity (EC 1.1.1.61) also fall into this category. Such enzymes have been characterized in *Ralstonia eutropha* (Bravo et al., *J. Forensic Sci.*, 49:379-387 (2004)), *Clostridium kluyveri* (Wolff et al., *Protein Expr. Purif.*, 6:206-212 (1995)) and *Arabidopsis thaliana* (Breitkreuz et al., *J. Biol. Chem.*, 278:41552-41556 (2003)). Yet another gene is the alcohol dehydrogenase adhI from *Geobacillus thermoglucosidasius* (Jeon et al., *J. Biotechnol.*, 135:127-133 (2008)). Data related to the sequences for each of these exemplary gene products can be found using the following GenBank accession numbers shown in Table 3.

TABLE 3

| PROTEIN | GENBANK ID | GI NUMBER | ORGANISM |
|---|---|---|---|
| 4hbd | YP_726053.1 | 113867564 | Ralstonia eutropha H16 |
| 4hbd | L21902.1 | 146348486 | Clostridium kluyveri DSM 555 |
| 4hbd | Q94B07 | 75249805 | Arabidopsis thaliana |
| adhI | AAR91477.1 | 40795502 | Geobacillus thermoglucosidasius M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J. Mol. Biol.*, 352:905-917 (2005)). The reversibility of the human 3-hydroxyisobutyrate dehydrogenase was demonstrated using isotopically-labeled substrate (Manning et al., *Biochem J.*, 231:481-484 (1985)). Additional genes encoding this enzyme include 3hidh in *Homo sapiens* (Hawes et al., *Methods Enzymol*, 324:218-228 (2000)) and *Oryctolagus cuniculus* (Hawes et al., supra; Chowdhury et al., *Biosci. Biotechnol Biochem.*, 60:2043-2047 (1996)), mmsB in *Pseudomonas aeruginosa* and *Pseudomonas putida* (Liao et al., US patent 20050221466), and dhat in *Pseudomonas putida* (Aberhart et al., *J. Chem. Soc.*, 6:1404-1406 (1979); Chowdhury et al., supra; Chowdhury et al., *Biosci. Biotechnol Biochem.*, 67:438-441 (2003)). Data related to the sequences for each of these exemplary gene products can be found using the following GenBank accession numbers shown in Table 4.

TABLE 4

| PROTEIN | GENBANK ID | GI NUMBER | ORGANISM |
|---|---|---|---|
| P84067 | P84067 | 75345323 | Thermus thermophilus |
| 3hidh | P31937.2 | 12643395 | Homo sapiens |
| 3hidh | P32185.1 | 416872 | Oryctolagus cuniculus |
| mmsB | P28811.1 | 127211 | Pseudomonas aeruginosa |
| mmsB | NP_746775.1 | 26991350 | Pseudomonas putida |
| dhat | Q59477.1 | 2842618 | Pseudomonas putida |

Oxidoreductases that convert a ketone functionality to the corresponding hydroxyl group are also synthetic steps in the disclosed pathways. Notably, Reactions L, O and H in FIG. 1 catalyzed by AKP dehydrogenase, 3-oxobutyraldehyde reductase (ketone reducing), 4-hydroxy-2-butanone reductase respectively are transformations of this category. The two latter transformations are also encountered in Steps B and F respectively in FIG. 2. On similar lines, the acetoacetyl-CoA reductase in Step G of FIG. 2 reduces acetoacetyl-CoA to 3-hydroxybutyryl-CoA.

The reduction of 4-oxo group of 2-amino-4-oxopentanoate (AKP) by a dehydrogenase yields 2-amino-4-hydroxypentanoate (FIG. 1, step L). This reaction is very similar to the NAD(P)H-dependent reduction of aspartate semialdehyde to homoserine catalyzed by homoserine dehydrogenase (EC 1.1.13). In many organisms, including *E. coli*, homoserine dehydrogenase is a bifunctional enzyme that also catalyzes the ATP-dependent conversion of aspartate to aspartyl-4-phosphate (Starnes et al., *Biochemistry*, 11:677-687 (1973)). The functional domains are catalytically independent and connected by a linker region (Sibilli et al., *J. Biol. Chem.*, 256:10228-10230 (1981)) and both domains are subject to allosteric inhibition by threonine. The homoserine dehydrogenase domain of the *E. coli* enzyme, encoded by thrA, was separated from the aspartate kinase domain, characterized, and found to exhibit high catalytic activity and reduced inhibition by threonine (James et al., *Biochemistry*, 41:3720-3725 (2002)). This can be applied to other bifunctional threonine kinases including, for example, hom1 of *Lactobacillus plantarum* (Cahyanto et al., *Microbiology*, 152:205-112 (2006)) and *Arabidopsis thaliana*. The monofunctional homoserine dehydrogenases encoded by hom6 in *S. cerevisiae* (Jacques et al., *Biochem. Biophys. Acta*, 1544:28-41 (2001)) and hom2 in *Lactobacillus plantarum* (Cahyanto et al., supra) have been functionally expressed and characterized in *E. coli*. Data related to the sequences for each of these exemplary gene products can be found using the following GenBank accession numbers shown in Table 5.

TABLE 5

| PROTEIN | GENBANK ID | GI NUMBER | ORGANISM |
|---|---|---|---|
| thrA | AAC73113.1 | 1786183 | Escherichia coli K12 |
| akthr2 | O81852 | 75100442 | Arabidopsis thaliana |
| hom6 | CAA89671 | 1015880 | Saccharomyces cerevisiae |
| hom1 | CAD64819 | 28271914 | Lactobacillus plantarum |
| hom2 | CAD63186 | 28270285 | Lactobacillus plantarum |

Acetoacetyl-CoA reductase (Step G, FIG. 2) catalyzing the reduction of acetoacetyl-CoA to 3-hydroxybutyryl-CoA participates in the acetyl-CoA fermentation pathway to butyrate in several species of *Clostridia* and has been studied in detail (Jones et al., *Microbiol. Rev.*, 50:484-524 (1986)). The enzyme from *Clostridium acetobutylicum*, encoded by hbd, has been cloned and functionally expressed in *E. coli* (Youngleson et al., *J. Bacteriol.*, 171:6800-6807 (1989)). Additionally, subunits of two fatty acid oxidation complexes in E. coli, encoded by fadB and fadJ, function as 3-hydroxyacyl-CoA dehydrogenases (Binstock et al., Methods Enzymol., 71C:403-411 (1981)). Yet other genes demonstrated to reduce acetoacetyl-CoA to 3-hydroxybutyryl-CoA are phbB from Zoogloea ramigera (Ploux et al., Eur. J. Biochem., 174:177-182 (1988)) and phaB from Rhodobacter sphaeroides (Alber et al., Mol. Microbiol., 61:297-309 (2006)). The former gene is NADPH-dependent, its nucleotide sequence has been determined (Peoples et al., Mol. Microbiol. 3:349-357 (1989)) and the gene has been expressed in E. coli. Substrate specificity studies on the gene led to the conclusion that it could accept 3-oxopropionyl-CoA as a substrate besides acetoacetyl-CoA (Ploux et al., supra). Additional genes include Hbd1 (C-terminal domain) and Hbd2 (N-terminal domain) in Clostridium kluyveri (Hillmer and Gottschalk, Biochim. Biophys. Acta 3334:12-23 (1974)) and HSD17B10 in Bos taurus (Wakil et al., J. Biol. Chem., 207:631-638 (1954)). Data related to the sequences for each of these exemplary gene products can be found using the following GenBank accession numbers shown in Table 6.

TABLE 6

| Protein | GENBANK ID | GI NUMBER | ORGANISM |
| --- | --- | --- | --- |
| fadB | P21177.2 | 119811 | Escherichia coli |
| fadJ | P77399.1 | 3334437 | Escherichia coli |
| Hbd2 | EDK34807.1 | 146348271 | Clostridium kluyveri |
| Hbd1 | EDK32512.1 | 146345976 | Clostridium kluyveri |
| hbd | P52041.2 | | Clostridium acetobutylicum |
| HSD17B10 | O02691.3 | 3183024 | Bos Taurus |
| phbB | P23238.1 | 130017 | Zoogloea ramigera |
| phaB | YP_353825.1 | 77464321 | Rhodobacter sphaeroides |

A number of similar enzymes have been found in other species of Clostridia and in Metallosphaera sedula (Berg et al., Archaea. Science, 318:1782-1786 (2007)) as shown in Table 7.

TABLE 7

| Protein | GenBank ID | GI number | Organism |
| --- | --- | --- | --- |
| Hbd | NP_349314.1 | NP_349314.1 | Clostridium acetobutylicum |
| Hbd | AAM14586.1 | AAM14586.1 | Clostridium beijerinckii |
| Msed_1423 | YP_001191505 | YP_001191505 | Metallosphaera sedula |
| Msed_0399 | YP_001190500 | YP_001190500 | Metallosphaera sedula |
| Msed_0389 | YP_001190490 | YP_001190490 | Metallosphaera sedula |
| Msed_1993 | YP_001192057 | YP_001192057 | Metallosphaera sedula |

An exemplary alcohol dehydrogenase that converts a ketone to a hydroxyl group is the secondary alcohol dehydrogenase that was shown to convert acetone to isopropanol in C. beijerinckii (Ismaiel et al., J. Bacteriol., 175:5097-5105 (1993)) and T. brockii (Lamed et al., Biochem. J., 195:183-190 (1981); Peretz et al., Biochemistry, 28:6549-6555 (1989)). The gene product of adhA from Pyrococcus furiosus, which exhibits maximum activity on 2-pentanol and pyruvaldehyde, was shown to have very broad specificity which includes isopropanol and acetone (Van der et al., Eur. J. Biochem., 268:3062-3068 (2001)). Yet another secondary alcohol dehydrogenase with activity on isopropanol and acetone is encoded by the gene product of adh-A from Rhodococcus ruber (Edegger et al., Chem. Commun. (Camb), 2402-2404 (2006); Kosjek et al., Biotechnol. Bioeng., 86:55-62 (2004)). These genes along with others are listed below in Table 8.

TABLE 8

| Protein | GenBank ID | GI number | Organism |
| --- | --- | --- | --- |
| adh | AAA23199.2 | 60592974 | Clostridium beijerinckii NRRL B593 |
| adh | P14941.1 | 113443 | Thermoanaerobacter brockii HTD4 |
| adhA | AAC25556 | 3288810 | Pyrococcus furiosus |
| adh-A | CAD36475 | 21615553 | Rhodococcus ruber |

Alternatively, there exist several exemplary alcohol dehydrogenases that convert a ketone to a hydroxyl functional group. Two such enzymes from E. coli are encoded by malate dehydrogenase (mdh) and lactate dehydrogenase (ldhA). In addition, lactate dehydrogenase from Ralstonia eutropha has been shown to demonstrate high activities on substrates of various chain lengths such as lactate, 2-oxobutyrate, 2-oxopentanoate and 2-oxoglutarate (Steinbuchel et al., Eur. J. Biochem., 130:329-334 (1983)). Conversion of the oxo functionality to the hydroxyl group can also be catalyzed by 2-keto1,3-butanediol reductase, an enzyme reported to be found in rat and in human placenta (Suda et al., Arch. Biochem. Biophys., 176:610-620 (1976); Suda et al., Biochem. Biophys. Res. Commun., 77:586-591 (1977)). All of these enzymes can provide a 3-oxobutyraldehyde reductase, and a 4-hydroxy-2-butanone reductase. An additional enzyme for these steps is the mitochondrial 3-hydroxybutyrate dehydrogenase (bdh) from the human heart which has been cloned and characterized (Marks et al., J. Biol. Chem. 267:15459-15463 (1992)). This enzyme is a dehydrogenase that operates on a 3-hydroxyacid. Data related to the sequences for each of these exemplary gene products can be found using the following GenBank accession numbers shown in Table 9.

TABLE 9

| Protein | GenBank ID | GI number | Organism |
| --- | --- | --- | --- |
| mdh | AAC76268.1 | 1789632 | Escherichia coli |
| ldhA | NP_415898.1 | 16129341 | Escherichia coli |
| ldh | YP_725182.1 | 113866693 | Ralstonia eutropha |
| bdh | AAA58352.1 | 177198 | Homo sapiens |

A number of organisms can catalyze the reduction of 4-hydroxy-2-butanone to 1,3-butanediol, including those belonging to the genus Bacillus, Brevibacterium, Candida, and Klebsiella among others, as described by Matsuyama et al. (1995).

Several transformations in FIGS. 2 and 3 rely on the two-step reduction of acyl-CoA to the corresponding alcohol. For example, Steps D and I in FIG. 2, involving the acetoacetyl-CoA reductase (CoA-dependent, alcohol forming) and 3-hydroxybutyryl-CoA reductase (alcohol forming), and Step E in FIG. 3 involving 3-hydroxybutyryl-CoA reductase (alcohol forming), shows such a transformation.

Exemplary two-step oxidoreductases that convert an acyl-CoA to alcohol include those that transform substrates such as acetyl-CoA to ethanol (e.g., adhE from E. coli (Kessler et al., FEBS. Lett., 281:59-63 (1991)) and butyryl-CoA to butanol (e.g. adhE2 from C. acetobutylicum (Fontaine et al., J. Bacteriol., 184:821-830 (2002)). In addition to reducing acetyl-CoA to ethanol, the enzyme encoded by adhE in

*Leuconostoc mesenteroides* has been shown to oxidize the branched chain compound isobutyraldehyde to isobutyryl-CoA (Kazahaya et al., *J. Gen. Appl. Microbiol.*, 18:43-55 (1972); Koo et al., *Biotechnol. Lett.*, 27:505-510 (2005)). Data related to the sequences for each of these exemplary gene products can be found using the following GenBank accession numbers shown in Table 10.

TABLE 10

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.*, 184:2404-2410 (2002); Strauss et al., *Eur. J. Biochem.*, 215:633-643 (1993)). This enzyme, with a mass of 300 kDa, is highly substrate-specific and shows little sequence similarity to other known oxidoreductases (Hugler et al., supra). No enzymes in other organisms have been shown to catalyze this specific reaction; however there is bioinformatic evidence that other organisms can have similar pathways (Klatt et al., *Environ. Microbiol.*, 9:2067-2078 (2007)). Enzymes in other organisms including *Roseiflexus castenholzii*, *Erythrobacter* sp. NAP1 and marine gamma proteobacterium HTCC2080 can be inferred by sequence similarity. Data related to the sequences for each of these exemplary gene products can be found using the following GenBank accession numbers shown in Table 11.

TABLE 11

| Protein | GenBank ID | GI Number | Organism |
|---|---|---|---|
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiology*, 122:635-644 (2000)) (FAR, AAD38039.1, 5020215, *Simmondsia chinensis*).

The pathways disclosed herein involve numerous oxidoreductase-type transformations that convert an acyl-CoA to an aldehyde. Specifically, Steps A and H in FIG. 2 catalyzed by acetoacetyl-CoA reductase (aldehyde forming) and 3-hydroxybutyryl-CoA reductase (aldehyde forming), and Step C from FIG. 3 showing the transformation catalyzed by 3-hydroxybutyryl-CoA reductase.

Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser et al., *J. of Bacteriology*, 179:2969-2975 (1997)), the *Acinetobacter* sp. M-1 fatty acyl-CoA reductase (Ishige et al., *Appl. Environ. Microbiol.*, 68:1192-1195 (2002)), and a CoA- and NADP-dependent succinate semialdehyde dehydrogenase encoded by the sucD gene in *Clostridium kluyveri* (Sohling et al., *J. Bacteriol.*, 178:871-880 (1996)). SucD of *P. gingivalis* is another succinate semialdehyde dehydrogenase (Takahashi et al., *J. Bacteriol.*, 182:4704-4710 (2000)). The enzyme acylating acetaldehyde dehydrogenase in *Pseudomonas* sp, encoded by bphG, is yet another enzyme demonstrated to oxidize and acylate acetaldehyde, propionaldehyde, butyraldehyde, isobutyraldehyde and formaldehyde (Powlowski et al., *J. Bacteriol.*, 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., supra; Koo et al., supra). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.*, 71:58-61 (2007)). Additional aldehyde dehydrogenase enzyme candidates are found in *Desulfatibacillum alkenivorans*, *Citrobacter koseri*, *Salmonella enterica*, *Lactobacillus brevis* and *Bacillus selenitireducens*. Data related to the sequences for each of these exemplary gene products can be found using the following GenBank accession numbers shown in Table 12.

TABLE 12

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| ald | ACL06658.1 | 218764192 | *Desulfatibacillum alkenivorans* AK-01 |
| ald | YP_001452373 | 157145054 | *Citrobacter koseri* ATCC BAA-895 |
| pduP | NP_460996.1 | 16765381 | *Salmonella enterica* Typhimurium |
| pduP | ABJ64680.1 | 116099531 | *Lactobacillus brevis* ATCC 367 |
| BselDRAFT_1651 | ZP_02169447 | 163762382 | *Bacillus selenitireducens* MLS10 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., supra; Thauer, R. K., Science, 318:1732-1733 (2007)). The enzyme utilizes NADPH as a cofactor and has been characterized in Metallosphaera and Sulfolobus spp (Alber et al., J. Bacteriol., 188:8551-8559 (2006); Hugler et al., supra). The enzyme is encoded by Msed_0709 in Metallosphaera sedula (Alber et al., supra; Berg et al., supra). A gene encoding a malonyl-CoA reductase from Sulfolobus tokodaii was cloned and heterologously expressed in E. coli (Alber et al., supra). This enzyme has also been shown to catalyze the conversion of methylmalonyl-CoA to its corresponding aldehyde (2007). Although the aldehyde dehydrogenase functionality of these enzymes is similar to the bifunctional dehydrogenase from Chloroflexus aurantiacus, there is little sequence similarity. Both malonyl-CoA reductase enzymes have high sequence similarity to aspartate-semialdehyde dehydrogenase, an enzyme catalyzing the reduction and concurrent dephosphorylation of aspartyl-4-phosphate to aspartate semialdehyde. Additional genes can be found by sequence homology to proteins in other organisms including Sulfolobus solfataricus and Sulfolobus acidocaldarius and have been listed below. Yet another enzyme for CoA-acylating aldehyde dehydrogenase is the ald gene from Clostridium beijerinckii (Toth et al., Appl. Environ. Microbiol., 65:4973-4980 (1999)). This enzyme has been reported to reduce acetyl-CoA and butyryl-CoA to their corresponding aldehydes. This gene is very similar to eutE that encodes acetaldehyde dehydrogenase of Salmonella typhimurium and E. coli (Toth et al., supra). Data related to the sequences for each of these exemplary gene products can be found using the following GenBank accession numbers shown in Table 13.

TABLE 13

| Protein | GenBank ID | GI Number | Organism |
| --- | --- | --- | --- |
| MSED_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 9473535 | Clostridium beijerinckii |
| eutE | AAA80209 | 687645 | Salmonella typhimurium |
| eutE | P77445 | 2498347 | Escherichia coli |

The oxidative deamination of amino groups to their corresponding oxo groups is catalyzed by deaminating oxidoreductases in the EC class 1.4.1. Such enzymes utilize $NAD^+$, $NADP^+$ or $FAD^+$ as acceptor. Enzymes in this class can convert 2-amino-4-oxopentanoate to 2,4-dioxopentanoate (FIG. 1, Step B), 2-amino-4-hydroxypentanoate to 2-oxo-4-hydroxypentanoate (FIG. 1, Step M) and 4-aminobutan-2-one to 3-oxobutyraldehyde (FIG. 1, Step K). Exemplary oxidoreductases operating on similar substrates include glutamate dehydrogenase (deaminating), encoded by gdhA, leucine dehydrogenase (deaminating), encoded by ldh, and aspartate dehydrogenase (deaminating), encoded by nadX. The gdhA gene product from Escherichia coli (McPherson et al., Nucleic. Acids Res. 11:5257-5266 (1983); Korber et al., J. Mol. Biol. 234:1270-1273 (1993)), gdh from Thermotoga maritima (Kort et al., Extremophiles 1:52-60 (1997); Lebbink et al., J. Mol. Biol. 280:287-296 (1998); Lebbink et al., J. Mol. Biol. 289:357-369 (1999)), and gdhA1 from Halobacterium salinarum (Ingoldsby et al., Gene. 349:237-244 (2005)) catalyze the reversible interconversion of glutamate to 2-oxoglutarate and ammonia, while favoring NADP(H), NAD(H), or both, respectively. Additional glutamate dehydrogenase gene candidates are found in Bacillus subtilis (Khan et al., Biosci. Biotechnol Biochem. 69:1861-1870 (2005)), Nicotiana tabacum (Purnell et al., Planta 222:167-180 (2005)), Oryza sativa (Abiko et al., Plant Cell Physiol 46:1724-1734 (2005)), Haloferax mediterranei (Diaz et al., Extremophiles. 10:105-115 (2006)), Halobacterium salinarum (Hayden et al., FEMS Microbiol Lett. 211:37-41 (2002)) and yeast (Roca et al., Appl Environ. Microbiol 69:4732-4736 (2003)). The Nicotiana tabacum enzyme is composed of alpha and beta subunits encoded by gdh1 and gdh2 (Purnell et al., Planta 222:167-180 (2005)). The ldh gene of Bacillus cereus encodes the LeuDH protein that accepts a wide of range of substrates including leucine, isoleucine, valine, and 2-aminobutanoate (Stoyan et al., J. Biotechnol 54:77-80 (1997); Ansorge et al., Biotechnol Bioeng. 68:557-562 (2000)). The nadX gene from Thermotoga maritime encoding for the aspartate dehydrogenase is involved in the biosynthesis of NAD (Yang et al., J. Biol. Chem. 278:8804-8808 (2003)). Data related to the sequences for each of these exemplary gene products can be found using the GenBank accession numbers shown below in Table 14.

TABLE 14

| Protein | GenBank ID | GI Number | Organism |
| --- | --- | --- | --- |
| gdhA | P00370 | 118547 | Escherichia coli |
| gdh | P96110.4 | 6226595 | Thermotoga maritima |
| gdhA1 | NP_279651.1 | 15789827 | Halobacterium salinarum |
| rocG | NP_391659.1 | 16080831 | Bacillus subtilis |
| gdh1 | AAR11534.1 | 38146335 | Nicotiana tabacum |
| gdh2 | AAR11535.1 | 38146337 | Nicotiana tabacum |
| GDH | Q852M0 | 75243660 | Oryza sativa |
| GDH | Q977U6 | 74499858 | Haloferax mediterranei |
| GDH | P29051 | 118549 | Halobactreium salinarum |
| GDH2 | NP_010066.1 | 6319986 | Saccharomyces cerevisiae |
| ldh | P0A393 | 61222614 | Bacillus cereus |
| nadX | NP_229443.1 | 15644391 | Thermotoga maritima |

An enzyme with 4-aminobutan-2-one oxidoreductase (deaminating) activity is required to convert 4-aminobutan-2-one to its corresponding aldehyde (FIG. 1, Step K). Exemplary candidates include 3,5-diaminohexanoate dehydrogenase (EC 1.4.1.11) and lysine 6-dehydrogenase (EC 1.4.1.18). 3,5-Diaminohexanoate dehydrogenase interconverts 3-amino acids and 3-oxoacids and has been characterized in organisms that ferment lysine. The gene encoding 3,5-diaminohexanoate dehydrogenase, kdd, was recently identified in Fusobacterium nucleatum (Kreimeyer et al., J Biol. Chem. 282:7191-7197 (2007)). The enzyme has been purified and characterized in other organisms (Baker et al., J Biol. Chem. 247:7724-7734 (1972); Baker et al., Biochemistry 13:292-299 (1974)) but the genes associated with these enzymes are not known. Candidates in other sequenced organisms can be inferred by sequence homology. Lysine 6-dehydrogenase, encoded by the lysDH genes, catalyzes the conversion of primary amines to their corresponding aldehydes. This enzyme naturally catalyzes the reversible oxidative deamination of the 6-amino group of L-lysine to form 2-aminoadipate-6-semialdehyde (Misono et al., J Bacteriol. 150:398-401 (1982)). Exemplary enzymes are found in Geobacillus stearothermophilus (Heydari et al., Appl Environ. Microbiol 70:937-942 (2004)), *Agrobacterium tumefaciens* (Hashimoto et al., *J Biochem.* 106:76-80 (1989); Misono and Nagasaki, *J Bacteriol.* 150:398-401 (1982)), and *Achromobacter denitrificans* (Ruldeekultham-rong et al., *BMB. Rep.* 41:790-795 (2008)). Data related to the sequences for each of these exemplary gene products can be found using the following GenBank accession numbers shown in Table 15.

TABLE 15

| Protein | GenBank ID | GI Number | Organism |
| --- | --- | --- | --- |
| kdd | AAL93966.1 | 19713113 | *Fusobacterium nucleatum* |
| lysDH | BAB39707 | 13429872 | *Geobacillus stearothermophilus* |
| lysDH | NP_353966 | 15888285 | *Agrobacterium tumefaciens* |
| lysDH | AAZ94428 | 74026644 | *Achromobacter denitrificans* |

2-Amino-4-oxopentanoate (AKP) thiolase or AKP thiolase (AKPT) (Step 1, FIG. 1) is a pyridoxal phosphate-dependent enzyme participating in ornithine degradation in *Clostridium sticklandii* (Jeng et al., *A. Biochemistry*, 13:2898-2903 (1974); Kenklies et al., *Microbiology*, 145:819-826 (1999)). A gene cluster encoding the alpha and beta subunits of AKPT (or-2 (ortA) and or-3 (ortB)) was recently identified and the biochemical properties of the enzyme were characterized (Fonknechten et al., *J. Bacteriol.*, In Press (2009)). The enzyme is capable of operating in both directions and reacts with the D-isomer of alanine. Enzyme engineering can be performed to optimize function with L-alanine as a substrate. AKPT from *Clostridium sticklandii* has been characterized but its protein sequence has not yet been published. Enzymes with high sequence homology are found in *Clostridium difficile*, *Alkaliphilus metalliredigenes* QYF, *Thermoanaerobacter* sp. X514, and *Thermoanaerobacter tengcongensis* MB4 (Fonknechten et al, supra). Data related to the sequences for each of these exemplary gene products can be found using the following GenBank accession numbers shown in Table 16.

TABLE 16

| Protein | GenBank ID | GI Number | Organism |
| --- | --- | --- | --- |
| ortA (A) | YP_001086914.1 | 126698017 | *Clostridium difficile* 630 |
| ortB (β) | YP_001086915.1 | 126698018 | *Clostridium difficile* 630 |
| Amet_2368 (α) | YP_001320181.1 | 150390132 | *Alkaliphilus metalliredigenes* QYF |
| Amet_2369 (β) | YP_001320182.1 | 150390133 | *Alkaliphilus metalliredigenes* QYF |
| Teth514_1478 (α) | YP_001663101.1 | 167040116 | *Thermoanaerobacter* sp. X514 |
| Teth514_1479 (β) | YP_001663102.1 | 167040117 | *Thermoanaerobacter* X514 |
| TTE1235 (α) | NP_622858.1 | 20807687 | *Thermoanaerobacter tengcongensis* MB4 |
| thrC (β) | NP_622859.1 | 20807688 | *Thermoanaerobacter tengcongensis* MB4 |

The conversion of 2-amino-4-oxopentanoate (AKP) to 2,4-dioxopentanoate (Step B, FIG. 1) is accomplished by 2-amino-4-oxopentanoate aminotransferase or oxidoreductase (deaminating). Selection of an appropriate enzyme for this transformation is dependent on the stereochemistry of the substrate. For example, if the substrate is in the D-configuration, a D-amino acid aminotransferase (EC 2.6.1.21) can be utilized, whereas the L-stereoisomer can utilize an L-aminotransferase such as aspartate aminotransferase (EC 2.6.1.1).

Aspartate aminotransferase transfers an amino group from aspartate to alpha-ketoglutarate, forming glutamate and oxaloacetate. Aspartate is similar in structure to 2-amino-4-oxopentanoate. This conversion is catalyzed by, for example, the gene products of aspC from *Escherichia coli* (Yagi et al., *FEBS Lett.*, 100:81-84 (1979); Yagi et al., *Methods Enzymol.*, 133:83-89 (1985)), AAT2 from *Saccharomyces cerevisiae* (Yagi et al., *J. Biochem.*, 92:35-43 (1982)) and ASP5 from *Arabidopsis thaliana* (Kwok et al., *J. Exp. Bot.*, 55:595-604 (2004); De la et al., *Plant J.*, 46:414-425 (2006); Wilkie et al., *Protein Expr. Purif.*, 12:381-389 (1998)). The enzyme from *Rattus norvegicus* has been shown to transaminate alternate substrates such as 2-aminohexanedioic acid and 2,4-diaminobutyric acid (Recasens et al., *Biochemistry*, 19:4583-4589 (1980)). Aminotransferases that work on other amino-acid-like substrates can also catalyze this transformation. Valine aminotransferase catalyzes the conversion of valine and pyruvate to 2-ketoisovalerate and alanine. The *E. coli* gene, avtA, encodes one such enzyme (Whalen et al., *J. Bacteriol.*, 150:739-746 (1982)). This gene product also catalyzes the amination of α-ketobutyrate to generate α-aminobutyrate, although the amine donor in this reaction has not been identified (Whalen et al., *J. Bacteriol.*, 158:571-574 (1984)). An additional candidate is alpha-aminoadipate transaminase (EC 2.6.1.39), an enzyme that participates in lysine biosynthesis and degradation in some organisms. The enzyme from *Thermus thermophilus*, encoded by lysN, is active with several alternate substrates including oxaloacetate, 2-oxoisocaproate, 2-oxoisovalerate, and 2-oxo-3-methylvalerate (Miyazaki et al., *Microbiol.* 150:2327-2334 (2004)). A similar enzyme from *Homo sapiens* has been characterized (Okuno et al., *Enz. Prot.* 47:136-148 (1993)). Data related to the sequences for each of these exemplary gene products can be found using the following GenBank accession numbers shown in Table 17.

TABLE 17

| Protein | GenBank ID | GI Number | Organism |
| --- | --- | --- | --- |
| aspC | NP_415448.1 | 16128895 | *Escherichia coli* |
| AAT2 | P23542.3 | 1703040 | *Saccharomyces cerevisiae* |
| ASP5 | P46248.2 | 20532373 | *Arabidopsis thaliana* |
| got2 | P00507 | 112987 | *Rattus norvegicus* |
| avtA | YP_026231.1 | 49176374 | *Escherichia coli* |
| lysN | BAC76939.1 | 31096548 | *Thermus thermophilus* |
| AadAT-II | Q8N5Z0.2 | 46395904 | *Homo sapiens* |

When the substrate is present as the D-stereoisomer, transamination can be catalyzed by D-aminotransferase (EC 2.6.1.21), also known as D-amino acid aminotransferase and D-alanine aminotransferase (DAAT). This class of enzymes is noted for its broad substrate specificity, which is species-specific. The D-aminotransferase from *Bacillus* species YM-1, encoded by dat, has been cloned, sequenced (Tanizawa et al., *J. Biol. Chem.*, 264:2450-2454 (1989)) and the crystal structure has been solved (Peisach et al., *Biochemistry*, 37:4958-4967 (1998)). This enzyme has also been the subject of protein engineering studies to alter the substrate specificity (Gutierrez et al., *Eur. J. Biochem*, 267:7218-7223 (2000); Gutierrez et al., *Protein Eng.*, 11:53-58 (1998)). Additional genes are found in *Bacillus licheniformis* ATCC 10716 (Taylor et al., *Biochim. Biophys. Acta.*, 1350:38-40 (1997)), *Staphylococcus haemolyticus* (Pucci et al., *J. Bacteriol.*, 177:336-342 (1995)) and *Bacillus subtilis* (Martinez-Carrion et al., *J. Biol. Chem.*, 240:3538-3546 (1965)). Data related to the sequences for each of these exemplary gene products can be found using the following GenBank accession numbers shown in Table 18.

TABLE 18

| Protein | GenBank ID | GI Number | Organism |
|---|---|---|---|
| dat | P19938 | 118222 | *Bacillus* sp. YM-1 |
| dat | P54692 | 1706292 | *Bacillus licheniformis* ATCC 10716 |
| dat | P54694 | 1706294 | *Staphylococcus haemolyticus* |
| dat | O07597.1 | 3121979 | *Bacillus subtilis* |

In reaction K of FIG. 1, 4-aminobutan-2-one is transaminated to form 3-oxobutanal. This transformation can likely be catalyzed by an aminotransferase that interconverts terminal amines and aldehydes. Exemplary candidate enzymes are beta-alanine/alpha-ketoglutarate aminotransferase, GABA aminotransferase, 3-amino-2-methylpropionate transaminase, lysine-6-aminotransferase, 2,4-diaminobutanoate transaminase, putrescine aminotransferase and diamine aminotransferase.

Cargill has developed and patented a beta-alanine/alpha-ketoglutarate aminotransferase for producing 3-HP from beta-alanine via malonyl-semialdehyde (Chandra et al., *ARch. Microbiol.*, 176:443-451 (2001)). The gene product of SkPYD4 in *Saccharomyces kluyveri* was also shown to preferentially use beta-alanine as the amino group donor (Aberhart et al., *J. Chem. Soc.* 6:1404-1406 (1979)). SkUGA1 encodes a homologue of *Saccharomyces cerevisiae* GABA aminotransferase, UGA1 (Ichikawa et al., *J. Mol. Catalysis A—Chem.*, 256:106-112 (2006)), whereas SkPYD4 encodes an enzyme involved in both β-alanine and GABA transamination (Aberhart et al., Supra). 3-amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Chopra et al., *Protein Expr. Purif.*, 25:533-540 (2002), Kuznetsova et al., *FEMS Microbiol. Rev.*, 29:263-279 (2005)). Enzyme candidates in other organisms with high sequence homology to 3-amino-2-methylpropionate transaminase include Gta-1 in *C. elegans* and gabT in *Bacillus subtilus*. Additionally, one of the native GABA aminotransferases in *E. coli*, encoded by gene gabT, has been shown to have broad substrate specificity (Fontaine et al., *J. Bacteriol.*, 184:821-830 (2002), Kanamasa et al., *Appl. Microbiol Biotechnol.*, 80:223-229 (2008)). The gene puuE encodes the other 4-aminobutyrate transaminase in *E. coli* (Drummond et al., *J. Biol. Chem.*, 235:318-325 (1960)).

Lysine-6-aminotransferase converts lysine to alpha-aminoadipate semialdehyde. Candidate enzymes have been characterized in *Candida utilis* (Hammer et al., *J Basic Microbiol* 32:21-27 (1992)), *Flavobacterium lutescens* (Fujii et al., *J Biochem.* 128:391-397 (2000)) and *Streptomyces clavuligenus* (Romero et al., *J Ind. Microbiol Biotechnol* 18:241-246 (1997)). A recombinant lysine-6-aminotransferase from *S. clavuligenus* was functionally expressed in *E. coli* (Tobin et al., *J Bacteriol.* 173:6223-6229 (1991)). The *F. lutescens* enzyme is specific to alpha-ketoglutarate as the amino acceptor (Soda et al., *Biochemistry* 7:4110-4119 (1968)). An enzyme with diaminobutanoate transaminase activity is encoded by the dat gene product in *Acinetobacter baumanii* (Ikai et al., *J Bacteriol.* 179:5118-5125 (1997)). In addition to its natural substrate, 2,4-diaminobutyrate, DAT transaminates the terminal amines of lysine, 4-aminobutyrate and ornithine. Candidate putrescine aminotransferase enzymes are encoded by ygjG in *E. coli* and spuC of *Pseudomonas aeruginosa* (Lu et al., *J Bacteriol.* 184:3765-3773 (2002)). The ygjG gene product reacts with the alternate substrates cadaverine, spermidine and 1,7-diaminoheptanoate (Samsonova et al., *BMC. Microbiol* 3:2 (2003); Kim, *J Biol. Chem.* 239:783-786 (1964)).

Data related to the sequences for each of these exemplary gene products can be found using the following GenBank accession numbers shown in Table 19.

TABLE 19

| Protein | GenBank ID | GI Number | Organism |
|---|---|---|---|
| SkyPYD4 | ABF58893.1 | 98626772 | *Saccharomyces kluyveri* |
| SkUGA1 | ABF58894.1 | 98626792 | *Saccharomyces kluyveri* |
| UGA1 | NP_011533.1 | 6321456 | *Saccharomyces cerevisiae* |
| Abat | P50554.3 | 122065191 | *Rattus norvegicus* |
| Abat | P80147.2 | 120968 | *Sus scrofa* |
| Gta-1 | Q21217.1 | 6016091 | *Caenorhabditis elegans* |
| gabT | P94427.1 | 6016090 | *Bacillus subtilis* |
| gabT | P22256.1 | 16130576 | *Escherichia coli* K12 |
| puuE | NP_415818.1 | 16129263 | *Escherichia coli* K12 |
| lat | BAB13756.1 | 10336502 | *Flavobacterium lutescens* |
| lat | AAA26777.1 | 153343 | *Streptomyces clavuligenus* |
| dat | P56744.1 | 6685373 | *Acinetobacter baumanii* |
| ygjG | NP_417544 | 145698310 | *Escherichia coli* |
| spuC | AAG03688 | 9946143 | *Pseudomonas aeruginosa* |

In FIG. 1, Step C, 2,4-dioxopentanoate is decarboxylated to form 3-oxobutyraldehyde by 2,4-dioxopentanoate decarboxylase. 2,4-dioxopentanoate is similar to the native substrates of pyruvate decarboxylase (EC 4.1.1.1) and benzoylformate decarboxylase (EC 4.1.1.7). Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (Li et al., *Biochemistry*, 38:10004-10012 (1999)). This enzyme has been extensively studied, engineered for altered activity, and functionally expressed in *E. coli* (Killenberg-Jabs et al., *Eur. J. Biochem.*, 268:1698-1704 (2001); Li et al., supra; Schure et al., *Appl. Environ. Microbiol.*, 64:1303-1307 (1998)). The PDC from *Zymomonas mobilus*, encoded by pdc, also has a broad substrate range and has been a subject of directed engineering studies to alter the affinity for different substrates (Siegert et al., *Protein Eng. Des. Sel.*, 18:345-357 (2005)). The crystal structure of this enzyme is available (Killenberg-Jabs, supra). Other well-characterized PDC enzymes include the enzymes from *Acetobacter pasteurians* (Chandra et al., *Arch. Microbiol.* 176:443-451 (2001)) and *Kluyveromyces lactis* (Krieger et al., *Eur. J. Biochem.*, 269:3256-3263 (2002)). Data related to the sequences for each of these exemplary gene products can be found using the following GenBank accession numbers shown in Table 20.

TABLE 20

| Protein | GenBank ID | GI Number | Organism |
|---|---|---|---|
| pdc | P06672.1 | 118391 | *Zymomonas mobilis* |
| pdc1 | P06169 | 30923172 | *Saccharomyces cerevisiae* |
| pdc | Q8L388 | 20385191 | *Acetobacter pasteurians* |
| pdc1 | Q12629 | 52788279 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Polovnikova et al., *Biochemistry* 42:1820-1830 (2003); Hasson et al., *Biochemistry*, 37:9918-9930 (1998)). Site-directed mutagenesis of two residues in the active site of the *Pseudomonas putida* enzyme altered the affinity (Km) of naturally and non-naturally occurring substrates (Siegert et al., supra). The properties of this enzyme have been further modified by directed engineering (Lingen et al., *Chembiochem*, 4:721-726 (2003); Lingen et al., *Protein Eng.*, 15:585-593 (2002)). The enzyme from *Pseudomonas aeruginosa*, encoded by mdlC, has also been characterized experimentally (Barrowman et al., *FEMS Microbiology Letters*, 34:57-60 (1986)). Additional genes from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.*, 72:7510-7517 (2006)). Data related to the sequences for each of these exemplary gene products can be found using the following GenBank accession numbers shown in Table 21.

TABLE 21

| Protein | GenBank ID | GI Number | Organism |
|---|---|---|---|
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian et al., *Proc. Natl. Acad. Sci. USA*, 102:10670-10675 (2005)) has been cloned and has been functionally expressed in *E. coli* at Genomatica. KDC enzyme activity has been detected in several species of *Rhizobia* including *Bradyrhizobium japonicum* and *Mesorhizobium loti* (Green et al., *J. Bacteriol.*, 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka et al., *Arch. Biochem. Biophys.*, 288:22-28 (1991)). The first twenty amino acids starting from the N-terminus were sequenced MTYKAPVKDVKFLL-DKVFKV (Shigeoka et al., supra). The gene can be identified by testing genes containing this N-terminal sequence for KDC activity. Data related to the sequences for each of these exemplary gene products can be found using the following GenBank accession numbers shown in Table 22.

TABLE 22

| Protein | GenBank ID | GI Number | Organism |
|---|---|---|---|
| kgd | O50463.4 | 160395583 | *Mycobacterium tuberculosis* |
| kgd | NP_767092.1 | 27375563 | *Bradyrhizobium japonicum* USDA110 |
| kgd | NP_105204.1 | 13473636 | *Mesorhizobium loti* |

A fourth enzyme for catalyzing this step is the branched chain alpha-ketoacid decarboxylase (BCKA). This class of enzymes has been shown to act on a variety of compounds varying in chain length from 3 to 6 carbons (Oku et al., *J. Biol. Chem.*, 263:18386-18396 (1988); Smit et al., *Appl. Environ. Microbiol.*, 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., supra). The enzyme has been structurally characterized (Berthold et al., *D. Biol. Crystallogr.*, 63:1217-1224 (2007)). Sequence alignments between the *Lactococcus lactis* enzyme and the pyruvate decarboxylase of *Zymomonas mobilis* indicate that the catalytic and substrate recognition residues are nearly identical (Siegert et al., supra), so this enzyme is readily amenable to directed engineering. Additional BCKA genes can be identified by homology to the *Lactococcus lactis* protein sequence (kdcA, AAS49166.1, 44921617, *Lactococcus lactis*). Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

2-amino-4-ketopentanoate is decarboxylated to form 4-aminobutan-2-one by AKP decarboxylase in Step E of FIG. 1. This transformation can be catalyzed by an amino acid decarboxylase. Selection of an appropriate decarboxylase depends on the stereochemical configuration of 4-amino-4-oxopentanoate. When this compound is in a D-configuration, a D-amino acid decarboxylase can be utilized. One such D-amino acid decarboxylase is diaminopimelate decarboxylase (DDC, EC 4.1.1.20). This enzyme decarboxylates the D-stereocenter of meso-diaminopimelate, catalyzing the final step of lysine biosynthesis. DDC has been studied in many organisms including *E. coli* (Momany et al., *D. Biol. Crystallogr.*, 58:549-552 (2002)), *Mycobacterium tuberculosis* (Kefala et al., *Acta. Crystallogr. Sect. F. Struct. Biol. Cryst. Commun.*, 61:782-784 (2005); Gokulan et al., *J. Biol. Chem.*, 278:18588-18596 (2003); Andersen et al., *Gene*, 124:105-109 (1993)), *Methylophilus methylotrophus* (Tsujimoto et al., *J. Biotechnol*, 124:327-337 (2006)), and *Helicobacter pylori* (Hu et al., *J. Biol. Chem.*, 283:21284-21293 (2008)). Alternately, the ornithine decarboxylase (EC 4.1.1.17) from *Homo sapiens* has a weak activity on the D-isomer of ornithine (Qu et al., *Biochem. J.*, 375:465-470 (2003); Fitzgerald et al., *DNA*, 8:623-634 (1989)) and can be used for the decarboxylation in step E. Data related to the sequences for each of these exemplary gene products can be found using the following GenBank accession numbers shown in Table 23.

TABLE 23

| Protein | GenBank ID | GI Number | Organism |
|---|---|---|---|
| lysA | NP_417315.1 | 16130742 | *Escherichia coli* |
| lysA | AAA25361.1 | 149964 | *Mycobacterium tuberculosis* |
| lysA | BAC92756.1 | 37196770 | *Methylophilus methylotrophus* |

TABLE 23-continued

| Protein | GenBank ID | GI Number | Organism |
|---|---|---|---|
| lysA | ABW70801.1 | 158523325 | Helicobacter pylori |
| odc1 | AA59969.1 | 386989 | Homo sapiens |

When 2-amino-4-ketopentanoate exhibits L-stereochemistry, an amino acid decarboxylase such as aspartate decarboxylase (EC 4.1.1.11), ornithine decarboxylase (EC 4.1.1.17) or lysine decarboxylase (EC 4.1.1.18) can be utilized. An exemplary enzyme is aspartate decarboxylase (EC 4.1.1.11). 2-Amino-4-ketopentanoate bears structural similarity to aspartate, the native substrate of this enzyme. Aspartate decarboxylase participates in pantothenate biosynthesis and is encoded by panD in *Escherichia coli* (Dusch et al., *Appl. Environ. Microbiol.*, 65:1530-1539 (1999); Ramjee et al., *Biochem. J.*, 323:661-669 (1997); Merkel et al., *FEMS Microbiol. Lett.*, 143:247-252 (1996); Schmitzberger et al., *EMBO J.*, 22:6193-6204 (2003)). The enzymes from *Mycobacterium tuberculosis* (Chopra et al., *Protein Expr. Purif.*, 25:533-540 (2002)) and *Corynebacterium glutanicum* (Dusch et al., supra) have been expressed and characterized in *E. coli*. Lysine decarboxylase enzymes are encoded in the *E. coli* genome by genes cadA and ldcC. A lysine decarboxylase analogous to CadA was recently identified in *Vibrio parahaemolyticus* (Tanaka et al., *J. Appl. Microbiol.* 104:1283-1293 (2008)). The lysine decarboxylase from *Selenomonas ruminantium*, encoded by ldc, bears sequence similarity to eukaryotic ornithine decarboxylases, and accepts both L-lysine and L-ornithine as substrates (Takatsuka et al., *Biosci. Biotechnol Biochem.* 63:1843-1846 (1999)). Ornithine decarboxylase enzyme candidates are found in *Nicotiana glutinosa* (Lee et al., Biochem. J. 360: 657-665 (2001)), *Lactobacillus* sp. 30a (Guirard et al., *J Biol. Chem.* 255:5960-5964 (1980)) and *Vibrio vulnificus* (Lee et al., *J Biol. Chem.* 282:27115-27125 (2007)). The residues involved in substrate specificity *Vibrio vulnificus* have been elucidated (Lee et al., supra).

Data related to the sequences for each of these exemplary gene products can be found using the following GenBank accession numbers shown in Table 24.

TABLE 24

| Protein | GenBank ID | GI Number | Organism |
|---|---|---|---|
| panD | P0A790 | 67470411 | Escherichia coli |
| panD | Q9X4N0 | 18203593 | Corynebacterium glutanicum |
| panD | P65660.1 | 54041701 | Mycobacterium tuberculosis |
| cadA | AAA23536. | 145458 | Escherichia coli |
| ldcC | AAC73297.1 | 1786384 | Escherichia coli |
| ldc | O50657.1 | 13124043 | Selenomonas ruminantium |
| cadA | AB124819.1 | 44886078 | Vibrio parahaemolyticus |
| AF323910.1:1 . . . 1299 | AAG45222.1 | 12007488 | Nicotiana glutinosa |
| odc1 | P43099.2 | 1169251 | Lactobacillus sp. 30a |
| VV2_1235 | NP_763142.1 | 27367615 | Vibrio vulnificus |

In reaction J (FIG. 1), acetylacrylate is decarboxylated to 2-oxobutene by acetoacrylate decarboxylase. An enzyme catalyzing this transformation has not been identified to date, but similar reactions are catalyzed by the enzymes aconitate decarboxylase, 4-oxalocrotonate decarboxylase and cinnamate decarboxylase.

Aconitate decarboxylase catalyzes the final step in itaconate biosynthesis in a strain of *Candida* and also in the filamentous fungus *Aspergillus terreus* (Bonnarme et al., *J. Bacteriol.*, 177:3573-3578 (1995); Willke et al., *Appl. Microbiol. Biotechnol.*, 56:289-295 (2001)). A cis-aconitate decarboxylase (CAD) (EC 4.1.16), encoded by ATEG_09971, has been identified and extensively studied in *Aspergillus terreus* and other related fungi. Recently, the gene has been cloned and functionally characterized (Kanamasa et al., *Appl. Microbiol. Biotechnol.*, 80:223-229 (2008)) and (WO/2009/014437).

4-oxalocronate decarboxylase has been isolated from numerous organisms and characterized. Genes encoding this enzyme include dmpH and dmpE in *Pseudomonas* sp. (strain 600) (Shingler et al., *J. Bacteriol.*, 174:711-724 (1992)), xylII and xylIII from *Pseudomonas putida* (Kato et al., *Arch. Microbiol.*, 168:457-463 (1997); Stanley et al., *Biochemistry*, 39:3514 (2000); Lian et al., *J. Am. Chem. Soc.*, 116:10403-10411 (1994)) and Reut_B5691 and Reut_B5692 from *Ralstonia eutropha* JMP134 (Hughes et al., *J. Bacteriol.*, 158:79-83 (1984)). The genes encoding the enzyme from *Pseudomonas* sp. (strain 600) have been cloned and expressed in *E. coli* (Shingler et al., supra). Data related to the sequences for each of these exemplary gene products can be found using the following GenBank accession numbers shown in Table 25.

TABLE 25

| Protein | GenBank ID | GI Number | Organism |
|---|---|---|---|
| dmpH | CAA43228.1 | 45685 | Pseudomonas sp. CF600 |
| dmpE | CAA43225.1 | 45682 | Pseudomonas sp. CF600 |
| xylII | YP_709328.1 | 111116444 | Pseudomonas putida |
| xylIII | YP_709353.1 | 111116469 | Pseudomonas putida |
| Reut_B5691 | YP_299880.1 | 73539513 | Ralstonia eutropha JMP134 |
| Reut_B5692 | YP_299881.1 | 73539514 | Ralstonia eutropha JMP134 |
| ATEG_09971 | EAU29420.1 | 114187720 | Aspergillus terreus |

An additional class of decarboxylases has been characterized that catalyze the conversion of cinnamate (phenylacrylate) and substituted cinnamate derivatives to the corresponding styrene derivatives. These enzymes are common in a variety of organisms and specific genes encoding these enzymes that have been cloned and expressed in *E. coli* are: pad1 from *Saccharomyces cerevisae* (Clausen et al., *Gene*, 142:107-112 (1994)), pdc from *Lactobacillus plantarum* (Barthelmebs et al., *Appl. Environ. Microbiol.*, 67:1063-1069 (2001); Rodriguez et al., *J. Agric. Food Chem.*, 56:3068-3072 (2008); Qi et al., *Biochem. J.*, 375:465-470 (2007)), pofK (pad) from *Klebsiella oxytoca* (Uchiyama et al., *Biosci. Biotechnol. Biochem.*, 72:116-123 (2008); Hashidoko et al., *Biosci. Biotech. Biochem.*, 58:217-218 (1994)), *Pedicoccus pentosaceus* (Barthelmebs et al., supra) and padC from *Bacillus subtilis* and *Bacillus pumilus* (Cavin et al., *Appl. Environ. Microbiol.*, 64:1466-1471 (1998)). A ferulic acid decarboxylase from *Pseudomonas fluorescens* also has been purified and characterized (Huang et al., *J. Bacteriol.*, 176:5912-5918 (1994)). Importantly, this class of enzymes has been shown to be stable and does not require either exogenous or internally bound co-factors, thus making these enzymes ideally suitable for biotransformations (Sariaslani, F. S., *Annu. Rev. Microbiol.*, 61:51-69 (2007)). Data related to the sequences for each of these exemplary gene products can be found using the following GenBank accession numbers shown in Table 26.

TABLE 26

| Protein | GenBank ID | GI Number | Organism |
|---|---|---|---|
| pad1 | AAB64980.1 | 1165293 | Saccharomyces cerevisae |
| pdc | AAC45282.1 | 1762616 | Lactobacillus plantarum |
| pad | BAF65031.1 | 149941608 | Klebsiella oxytoca |
| padC | NP_391320.1 | 16080493 | Bacillus subtilis |
| pad | YP_804027.1 | 116492292 | Pedicoccus pentosaceus |
| pad | CAC18719.1 | 11691810 | Bacillus pumilus |

An additional enzyme for decarboxylation is acetoacetate decarboxylase (EC 4.1.1.4), an enzyme that decarboxylates acetoacetate to acetone and has therefore been studied for its role in bacterial solventogenesis. Exemplary bacterial enzymes have been characterized from *Clostridium acetobutylicum* (Benner et al., *J. Am. Chem. So.* 103:993-994 (1981); HIghbarger et al., *Biochemistry* 35:41-46 (1996); Petersen et al., *Appl. Environ. Microbiol.* 56:3491-3498 (1990); Rozzel et al. *J. Am. Chem. Soc.* 106:4937-4941 (1984)) *Clostridium saccharoperbutylacetonicum* (Kosaka, et al., *Biosci. Biotechnol Biochem.* 71:58-68 (2007)) and *Clostridium beijerinckii* (Ravagnani et al. *Mol. Microbiol.* 37:1172-1185 (2000)). Acetoacetate decarboxylase activity has also been demonstrated in *Pseudomonas putida* and *Bacillus polymyxa* but genes are not associated with this activity to date (Matiasek et al., *Curr. Microbiol.* 42: 276-281 (2001)). Bacterial genes in other organisms such as *Clostridium botulinum* and *Bacillus amyloliquefaciens* can be identified by sequence homology. In humans and other mammals, acetoacetate decarboxylase catalyzes the final step of the ketone-body pathway (Kalapos, *Biochim. Biophys. Acta* 1621:122-139 (2003)), but genes associated with this activity have not been identified to date. Data related to the sequences for each of these exemplary gene products can be found using the following GenBank accession numbers shown in Table 27.

TABLE 27

| Protein | GenBank ID | GI Number | Organism |
|---|---|---|---|
| adc | NP_149328.1 | 15004868 | Clostridium acetobutylicum |
| adc | AAP42566.1 | 31075386 | Clostridium saccharoperbutylacetonicum |
| cbei_3835 | YP_001310906.1 | 150018652 | Clostridium beijerinckii |
| CLL_A2135 | YP_001886324.1 | 187933144 | Clostridium botulinum |
| RBAM_030030 | YP_001422565.1 | 154687404 | Bacillus amyloliquefaciens |

All the aforementioned gene candidates can also be used to catalyze the decarboxylation of 2-oxo-4-hydroxypentanoate to 3-hydroxybutyraldehyde in Step N of FIG. 1.

Butenone hydratase (Step G, FIG. 1), 4-hydroxybutyryl-CoA dehydratase (Step A, FIG. 3) and crotonase (Step A, FIG. 3) are hydrolyase-type transformations. Specifically, the hydration of butenone to 4-hydroxy-2-butanone (Step G, FIG. 1) can be accomplished by an enzyme in the hydratase family of enzymes. Enzymes that can carry out this transformation include fumarate hydratase (EC 4.2.1.2), 2-(hydroxymethyl)glutarate dehydratase (EC 4.2.1.-), dimethylmaleate hydratase (EC 4.2.1.85) and citramalate hydrolyase (EC 4.2.1.34).

Fumarate hydratase enzymes naturally catalyze the reversible hydration of fumarate to malate. Although the ability of fumarate hydratase to react with butanone as a substrate has not been described in the literature, a wealth of structural information is available for this enzyme and other researchers have successfully engineered the enzyme to alter activity, inhibition and localization (Weaver, T., *B. Biol.*

*Crystallogr.*, 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., *J. Bacteriol.*, 183:461-467 (2001); Woods et al., *Biochem. Biophys. Acta.*, 954:14-26 (1988); Guest et al., *J. Gen. Microbiol.*, 131: 2971-2984 (1985)). Additional enzymes are found in *Campylobacter jejuni* (Smith et al., *Int. J. Biochem. Cell Biol.*, 31:961-975 (1999)), *Thermus thermophilus* (Mizobata et al., *Arch. Biochem. Biophys.*, 355:49-55 (1998)) and *Rattus norvegicus* (Kobayashi et al., *J. Biochem.*, 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.*, 270:207-213 (2007)). Data related to the sequences for each of these exemplary gene products can be found using the following GenBank accession numbers shown in Table 28.

TABLE 28

| Protein | GenBank ID | GI Number | Organism |
|---|---|---|---|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| fumC | O69294 | 9789756 | Campylobacter jejuni |
| fumC | P84127 | 75427690 | Thermus thermophilus |
| fumH | P14408 | 120605 | Rattus norvegicus |
| fum1 | P93033 | 39931311 | Arabidopsis thaliana |
| fumC | Q8NRN8 | 39931596 | Corynebacterium glutamicum |

TABLE 28-continued

| Protein | GenBank ID | GI Number | Organism |
|---|---|---|---|
| MmcB | YP_001211906 | 147677691 | Pelotomaculum thermopropionicum |
| MmcC | YP_001211907 | 147677692 | Pelotomaculum thermopropionicum |

Two additional hydratase enzymes are 2-(hydroxymethyl)glutarate dehydratase and dimethylmaleate hydratase, enzymes studied for their role in nicontinate catabolism in *Eubacterium barkeri* (formerly *Clostridium barkeri*) (Alhapel et al., *Proc. Natl. Acad. Sci. USA*, 103:12341-12346 (2006)). 2-(Hydroxymethyl)glutarate dehydratase is a [4Fe-4S]-containing enzyme that dehydrates 2-(hydroxymethyl) glutarate to 2-methylene-glutarate. This enzyme is encoded by hmd in *Eubacterium barkeri* (Alhapel et al., supra). Similar enzymes with high sequence homology are found in *Bacteroides capillosus*, *Anaerotruncus colihominis*, and *Natranaerobius thermophilius*. These enzymes are homologous to the alpha and beta subunits of [4Fe-4S]-containing bacterial serine dehydratases (e.g., *E. coli* enzymes encoded by tdcG, sdhB, and sdaA). Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel, et al., supra; Kollmann-Koch et al., *Physiol. Chem.*, 365:847-857 (1984)). Data related to the sequences for each of these exemplary gene products can be found using the following GenBank accession numbers shown in Table 29.

TABLE 29

| Protein | GenBank ID | GI Number | Organism |
| --- | --- | --- | --- |
| hmd | ABC88407.1 | 86278275 | *Eubacterium barkeri* |
| BACCAP_02294 | ZP_02036683.1 | 154498305 | *Bacteroides capillosus* ATCC 29799 |
| ANACOL_02527 | ZP_02443222.1 | 167771169 | *Anaerotruncus colihominis* DSM 17241 |
| NtherDRAFT_2368 | ZP_02852366.1 | 169192667 | *Natranaerobius thermophilus* JW/NM-WN-LF |
| dmdA | ABC88408 | 86278276 | *Eubacterium barkeri* |
| dmdB | ABC88409.1 | 86278277 | *Eubacterium barkeri* |

An additional enzyme is 2-methylmalate dehydratase, also called citramalate hydrolyase, a reversible hydrolyase that catalyzes the alpha, beta elimination of water from citramalate to form mesaconate. This enzyme has been purified and characterized in *Clostridium tetanomorphum* (Wang et al., *J. Biol. Chem.*, 244:2516-2526 (1969)). The activity of this enzyme has also been detected in several bacteria in the genera *Citrobacter* and *Morganella* in the context of the glutamate degradation VI pathway (Kato et al., supra). Genes encoding this enzyme have not been identified in any organism to date.

Hydration of crotonyl-CoA to form 3-hydroxybutyryl-CoA (Step B, FIG. 3) is catalyzed by a crotonase (EC 4.2.1.55). These enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Boynton et al., *J. Bacteriol.*, 178:3015-3024 (1996)), *C. kluyveri* (Hillmer et al., *FEBS Lett.*, 21:351-354 (1972)), and *Metallosphaera sedula* (Berg et al., supra). Enoyl-CoA hydratases, which are involved in fatty acid beta-oxidation and/or the metabolism of various amino acids, can also catalyze the hydration of crotonyl-CoA to form 3-hydroxybutyryl-CoA (Roberts et al., *Arch. Microbiol.*, 117:99-108 (1978); Agnihotri et al., *Bioorg. Med. Chem.*, 11:9-20 (2003); Conrad et al., *J. Bacteriol.*, 118:103-111 (1974)). An exemplary enoyl-CoA hydratase is the gene product of ech from *Pseudomonas putida* (Roberts et al., supra). The enoyl-CoA hydratases, phaA and phaB, of *P. putida* have been indicated to carry out the hydroxylation of double bonds during phenylacetate catabolism (Olivera et al., *Proc. Natl. Acad. Sci USA*, 95:6419-6424 (1998)). The paaA and paaB from *P. fluorescens* catalyze analogous transformations (Olivera et al., supra). Lastly, a number of *Escherichia coli* genes have been shown to demonstrate enoyl-CoA hydratase functionality including maoC (Park et al., *J. Bacteriol.*, 185:5391-5397 (2003)), paaF (Ismail et al., *Eur. J. Biochem.*, 270:3047-3054 (2003); Park et al., *Appl. Biochem. Biotechnol.*, 113-116:335-346 (2004); Park et al., *Biotechnol Bioeng.*, 86:681-686 (2004)) and paaG (Ismail et al., supra; Park et al., supra; Park et al., supra). Data related to the sequences for each of these exemplary gene products can be found using the following GenBank accession numbers shown in Table 30.

TABLE 30

| Protein | GenBank ID | GI Number | Organism |
| --- | --- | --- | --- |
| crt | NP_349318.1 | 15895969 | *Clostridium acetobutylicum* |
| crt1 | YP_001393856 | 153953091 | *Clostridium kluyveri* DSM 555 |
| ech | NP_745498.1 | 26990073 | *Pseudomonas putida* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Haller et al., *Biochemistry* 39:4622-4629 (2000); Martinez-Carrion et a., *J. Biol. Chem.* 240:3538-3546 (1965); Matthies et al., *Appl. Environ. Micriobiol.* 58:1435-1439 (1992)). Knocking out a negative regulator encoded by fadR can be utilized to activate the fadB gene product (Jeng et al., *A. Biochemistry* 13:2898-2903 (1974)). The fadI and fadJ genes encode similar functions and are naturally expressed under anaerobic conditions (Atsumi et al., *Nature* 451:86-89 (2008)). Data related to the sequences for each of these exemplary gene products can be found using the following GenBank accession numbers shown in Table 31.

TABLE 31

| Protein | GenBank ID | GI Number | Organism |
| --- | --- | --- | --- |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

The reversible condensation of 4-hydroxybutyryl-CoA to crotonyl-CoA (Step A, FIG. 3) is catalyzed by the bifunctional enzyme 4-hydroxybutyryl-CoA dehydratase/vinylacetyl-CoA 4-isomerase. This enzyme first dehydrates 4-hydroxybutyryl-CoA to vinylacetyl-CoA, which subsequently rearranges to form crotonoyl-CoA. The enzymes from *Clostridium kluyveri* and *C. aminobutyrium* have been purified, characterized, and sequenced at the N-terminal domain (Scherf et al., *Eur. J. Biochem.*, 215:421-429 (1993); Scherf et al., *Arch. Microbiol.*, 161:239-245 (1994)). The abfD genes from *C. aminobutyrium* and *C. kluyveri* match exactly with these N-terminal amino acid sequences, and have been indicated to encode the 4-hydroxybutyrul-CoA dehydratases/vinylacetyl-CoA Δ-isomerase activities. Similar genes are identified through homology from genome projects, including abfD from *Porphyromonas gingivalis* and Msed_1220 from *Metallosphaera sedula*. Data related to the sequences for each of these exemplary gene products can be found using the following GenBank accession numbers shown in Table 32.

TABLE 32

| Protein | GenBank ID | GI Number | Organism |
| --- | --- | --- | --- |
| abfD | YP_001396399.1 | 153955634 | Clostridium kluyveri |
| abfD | P55792 | 84028213 | Clostridium aminobutyricum |
| abfD | YP_001928843 | 188994591 | Porphyromonas gingivalis |
| Msed_1220 | YP_001191305.1 | 146303989 | Metallosphaera sedula |

Deamination of 2-amino-4-ketopentanoate (FIG. 1, Reaction I) and of 4-aminobutan-2-one (Step F, FIG. 1) can be accomplished by AKP ammonia-lyase and 4-aminobutan-2-one ammonia-lyase respectively. These deaminations are very similar to the deamination of aspartate to fumarate by aspartase. The enzyme has been extensively studied and several crystal structures are available. The *E. coli* enzyme has been shown to react with alternate substrates such as aspartatephenylmethylester, asparagine, benzyl-aspartate and malate (Ma et al., *Ann. N.Y. Acad. Sci.*, 672:60-65 (1992). In a separate study, directed evolution has been implemented on this enzyme to alter substrate specificity (Asano et al., *Biomol. Eng.*, 22:95-101 (2005)). Enzymes with aspartase functionality have also been characterized in *Haemophilus influenzae* (Sjostrom et al., *Biochem. Biophys. Acta.*, 1324:182-190 (1997)), *Pseudomonas fluorescens* (Takagi et al., *J. Biochem.*, 96:545-552 (1984)), *Bacillus subtilus* (Sjostrom et al., supra) and *Serratia marcescens* (Takagi et al., *J. Bacteriol.*, 161:1-6 (1985)). Data related to the sequences for each of these exemplary gene products can be found using the following GenBank accession numbers shown in Table 33.

TABLE 33

| Protein | GenBank ID | GI Number | Organism |
| --- | --- | --- | --- |
| aspA | NP_418562 | 90111690 | Escherichia coli |
| aspA | P44324.1 | 1168534 | Haemophilus influenzae |
| aspA | P07346.1 | 114273 | Pseudomonas fluorescens |
| ansB | P26899.1 | 251757243 | Bacillus subtilus |
| aspA | P33109.1 | 416661 | Serratia marcescens |

A similar ammonia lyase reaction is catalyzed by methylaspartase (EC 4.3.1.2), an enzyme participating in the glutamate fermentation route via mesaconate (Kato et al., supra). This enzyme, also known as beta-methylaspartase and 3-methylaspartate ammonia-lyase, naturally catalyzes the deamination of threo-3-methylasparatate to mesaconate. The 3-methylaspartase from *Clostridium tetanomorphum* has been cloned, functionally expressed in *E. coli*, and crystallized (Asuncion et al., 57:731-733 (2001); Asuncion et al., *J Biol Chem.* 277:8306-8311 (2002); Botting et al., 27:2953-2955 (1988); Goda et al., 31:10747-10756 (1992)). In *Citrobacter amalonaticus*, this enzyme is encoded by BAA28709 (Kato et al., *Arch. Microbiol* 168:457-463 (1997)). 3-Methylaspartase has also been crystallized from *E. coli* YG1002 (Asano et al., *FEMS Microbiol Lett.* 118: 255-258 (1994)) although the protein sequence is not listed in public databases such as GenBank. Data related to the sequences for each of these exemplary gene products can be found using the following GenBank accession numbers shown in Table 34.

TABLE 34

| Protein | GenBank ID | GI Number | Organism |
| --- | --- | --- | --- |
| mal | AAB24070.1 | 259429 | Clostridium tetanomorphum |
| BAA28709 | BAA28709.1 | 3184397 | Citrobacter amalonaticus |

In some embodiments, the 2-amino-4-ketopentanoate (AKP) thiolase encoded by one or more genes selected from the group consisting of ortA (α), ortB (β), Amet_2368 (α), Amet_2369 (β), Teth514_1478 (α), Teth514_1479 (β), TTE1235 (α), and thrC (β).

In some embodiments, the AKP dehydrogenase is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the 2-amino-4-hydroxypentanoate aminotransferase is encoded by one or more genes selected from the group consisting of aspC, AAT2, ASP5, got2, avtA, lysN, AadAT-II, dat, lat, ygjG, spuC, SkyPYD4, SkUGA1, UGA1, Abat, Abat, Gta-1, gabT, and puuE.

In some embodiments, the 2-amino-4-hydroxypentanoate oxidoreductase (deaminating) is encoded by one or more genes selected from the group consisting of gdhA, gdh, gdhA1, rocG, gdh1, gdh2, GDH, GDH2, ldh and nadX.

In some embodiments, the 2-oxo-4-hydroxypentanoate decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, pofK (pad), padC, pad, adc, cbei_3835, CLL_A2135, RBAM_030030, In some embodiments, the 3-hydroxybutyraldehdye reductase is encoded by one or more genes selected from the group consisting of alrA, ADH2, yqhD, bdh I, bdh II, adhA, 4hbd, adhI, P84067, mmsb, dhat, and 3hidh.

In some embodiments, the AKP aminotransferase is encoded by one or more genes selected from the group consisting of aspC, AAT2, ASP5, got2, avtA, lysN, AadAT-II, dat, lat, ygjG, spuC, SkyPYD4, SkUGA1, UGA1, Abat, Gta-1, gabT, and puuE.

In some embodiments, the AKP oxidoreductase (deaminating) is encoded by one or more genes selected from the group consisting of gdhA, gdh, gdhA1, rocG, gdh1, gdh2, GDH, GDH2, ldh and nadX. In some embodiments, the 2,4-dioxopentanoate decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, padC, and pad, adc, cbei_3835, CLL_A2135, RBAM_030030.

In some embodiments, the 3-oxobutyraldehyde reductase (ketone reducing) is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the 3-oxobutyraldehyde reductase (aldehyde reducing) is encoded by one or more genes selected from the group consisting of alrA, ADH2, yqhD, bdh I, bdh II, adhA, 4hbd, adhI, P84067, mmsb, dhat, and 3hidh.

In some embodiments, the 4-hydroxy-2-butanone reductase is encoded by one or more genese selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the AKP decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, pofK(pad), padC, pad.

In some embodiments, the 4-aminobutan-2-one aminotransferase is encoded by one or more genes selected from the group consisting of aspC, AAT2, ASP5, got2, avtA, lysN, AadAT-II, dat, lat, ygjG, spuC, SkyPYD4, SkUGA1, UGA1, Abat, Gta-1, gabT, and puuE.

In some embodiments, the 4-aminobutan-2-one oxidoreductase (deaminating) is encoded by one or more genes selected from the group consisting of gdhA, gdh, gdhA1, rocG, gdh1, gdh2, GDH, GDH2, ldh, nadX, kdd and lysDH.

In some embodiments, the 4-aminobutan-2-one ammonia-lyase is encoded by one or more genes selected from the group consisting of aspA, ansB, mal and BAA28709.

In some embodiments, the butenone hydratase is encoded by one or more genes selected from the group consisting of fumA, fumB, fumC, fumH, fum1, MmcB, MmcC, hmd, BACCAP_02294, ANACOL_02527, NtherDRAFT_2368, dmdA, dmdB, crt, crt1, ech paaA, paaB, phaA, phaB, maoC, paaF, paaG, abfD, Msed_1220, fadA, fadB, fadI, fadJ, and fadR.

In some embodiments, the AKP ammonia-lyase is encoded by one or more genes selected from the group consisting of aspA, ansB, mal and BAA28709.

In some embodiments, the acetylacrylate decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, pofK (pad), padC, pad, adc, cbei_3835, CLL_A2135, RBAM_030030)

In some embodiments, the acetoacetyl-CoA reductase (CoA-dependent, aldehyde forming) is encoded by one or more genes selected from the group consisting of acr1, sucD, bphG, bld, adhE, Msed_0709, mcr, asd-2, Saci_2370, Ald, and eutE.

In some embodiments, the acetoacetyl-CoA reductase (CoA-dependent, alcohol forming) is encoded by one or more genes selected from the group consisting of adhE, adhE2, mcr, Rcas_2929, NAP1_02720, MGP2080_00535, and FAR.

In some embodiments, the acetoacetyl-CoA reductase (ketone reducing) is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the 3-hydroxybutyryl-CoA reductase (aldehyde forming) is encoded by one or more genes selected from the group consisting of acr1, sucD, bphG, bld, adhE, Msed_0709, mcr, asd-2, Saci_2370, Ald, and eutE.

In some embodiments, the 3-hydroxybutyryl-CoA reductase (alcohol forming) is encoded by one or more genes selected from the group consisting of adhE, adhE2, mcr, Rcas_2929, NAP1_02720, MGP2080_00535, and FAR.

In some embodiments, the 4-hydroxybutyryl-CoA dehydratase is encoded by one or more genes selected from the group consisting of fumA, fumB, fumC, fumH, fum1, MmcB, MmcC, hmd, BACCAP 02294, ANACOL 02527, NtherDRAFT 2368, dmdA, dmdB, crt, crt1, ech, paaA, paaB, phaA, phaB, maoC, paaF, paaG, abfD, Msed_1220, fadA, fadB, fadI, fadJ, and fadR.

In some embodiments, the crotonase is encoded by one or more genes selected from the group consisting of fumA, fumB, fumC, fumH, fum1, MmcB, MmcC, hmd, BACCAP_02294, ANACOL_02527, NtherDRAFT_2368, dmdA, dmdB, crt, crt1, ech paaA, paaB, phaA, phaB, maoC, paaF, paaG, abfD, Msed_1220, fadA, fadB, fadI, fadJ, and fadR.

The non-naturally occurring microbial organisms of the invention can be produced by introducing expressible nucleic acids encoding one or more of the enzymes or proteins participating in one or more 1,3-butanediol biosynthetic pathways. Depending on the host microbial organism chosen for biosynthesis, nucleic acids for some or all of a particular 1,3-butanediol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve 1,3-butanediol biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 1,3-butanediol.

Depending on the 1,3-butanediol biosynthetic pathway constituents of a selected host microbial organism, the non-naturally occurring microbial organisms of the invention will include at least one exogenously expressed 1,3-butanediol pathway-encoding nucleic acid and up to all encoding nucleic acids for one or more 1,3-butanediol biosynthetic pathways. For example, 1,3-butanediol biosynthesis can be established in a host deficient in a pathway enzyme or protein through exogenous expression of the corresponding encoding nucleic acid. In a host deficient in all enzymes or proteins of an 1,3-butanediol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 1,3-butanediol can be included.

Given the teachings and guidance provided herein, those skilled in the art will understand that the number of encoding nucleic acids to introduce in an expressible form will, at least, parallel the 1,3-butanediol pathway deficiencies of the selected host microbial organism. Therefore, a non-naturally occurring microbial organism of the invention can have one, two, three, four, five, up to all nucleic acids encoding the enzymes or proteins constituting an 1,3-butanediol biosynthetic pathway disclosed herein. In some embodiments, the non-naturally occurring microbial organisms also can include other genetic modifications that facilitate or optimize 1,3-butanediol biosynthesis or that confer other useful functions onto the host microbial organism. One such other functionality can include, for example, augmentation of the synthesis of one or more of the 1,3-butanediol pathway precursors such as acetyl-CoA.

Generally, a host microbial organism is selected such that it produces the precursor of an 1,3-butanediol pathway, either as a naturally produced molecule or as an engineered product that either provides de novo production of a desired precursor or increased production of a precursor naturally produced by the host microbial organism. For example, acetyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of an 1,3-butanediol pathway.

In some embodiments, a non-naturally occurring microbial organism of the invention is generated from a host that contains the enzymatic capability to synthesize 1,3-butanediol. In this specific embodiment it can be useful to increase the synthesis or accumulation of an 1,3-butanediol pathway product to, for example, drive 1,3-butanediol pathway reactions toward 1,3-butanediol production. Increased synthesis or accumulation can be accomplished by, for example, overexpression of nucleic acids encoding one or more of the above-described 1,3-butanediol pathway enzymes or proteins. Over expression the enzyme or enzymes and/or protein or proteins of the 1,3-butanediol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 1,3-butanediol, through overexpression of one, two, three, four, five, that is, up to all nucleic acids encoding 1,3-butanediol biosynthetic pathway enzymes or proteins. In addition, a non-naturally occurring organism can be generated by mutagenesis of an endogenous gene that results in an increase in activity of an enzyme in the 1,3-butanediol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, 1,3-butanediolbiosynthetic pathway onto the microbial organism. Alternatively, encoding nucleic acids can be introduced to produce an intermediate microbial organism having the biosynthetic capability to catalyze some of the required reactions to confer 1,3-butanediol biosynthetic capability. For example, a non-naturally occurring microbial organism having 1,3-butanediol biosynthetic pathway can comprise at least two exogenous nucleic acids encoding desired enzymes or proteins. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention and so forth, as desired, so long as the combination of enzymes and/or proteins of the desired biosynthetic pathway results in production of the corresponding desired product. Similarly, any combination of four, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of 1,3-butanediol as described herein, the non-naturally occurring microbial organisms and methods of the invention also can be utilized in various combinations with each other and with other microbial organisms and methods well known in the art to achieve product biosynthesis by other routes. For example, one alternative to produce 1,3-butanediol other than use of the 1,3-butanediol producers is through addition of another microbial organism capable of converting 1,3-butanediol pathway intermediate to 1,3-butanediol. One such procedure includes, for example, the fermentation of a microbial organism that produces 1,3-butanediol pathway intermediate. The 1,3-butanediol pathway intermediate can then be used as a substrate for a second microbial organism that converts the 1,3-butanediol pathway intermediate to 1,3-butanediol. The 1,3-butanediol pathway intermediate can be added directly to another culture of the second organism or the original culture of the 1,3-butanediol pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 1,3-butanediol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 1,3-butanediol can be accomplished by constructing a microbial organism that contains biosynthetic pathways for conversion of one pathway intermediate to another pathway intermediate or the product. Alternatively, 1,3-butanediol also can be biosynthetically produced from microbial organisms through co-culture or co-fermentation using two organisms in the same vessel, where the first microbial organism produces 1,3-butanediol intermediate and the second microbial organism converts the intermediate to 1,3-butanediol.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 1,3-butanediol.

Sources of encoding nucleic acids for 1,3-butanediol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 1,3-butanediol biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of 1,3-butanediol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 1,3-butanediol biosynthetic pathway exists in an unrelated species, 1,3-butanediol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms can differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 1,3-butanediol.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*. *E. coli* is a particularly useful host organism since it is a well characterized microbial organism suitable for genetic engineering. Other particularly useful host organisms include yeast such as *Saccharomyces cerevisiae*.

Methods for constructing and testing the expression levels of a non-naturally occurring 1,3-butanediol-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of 1,3-butanediol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 1,3-butanediol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention provides a method for producing 1,3-BDO that includes culturing the non-naturally occurring microbial organism disclosed herein, under conditions and for a sufficient period of time to produce 1,3-BDO, including organisms that incorporate one, two, three, four, five, up to all exogenous nucleic acids encoding enzymes that complete a 1,3-BDO pathway. The 1,3-BDO pathways include a set of 1,3-BDO pathway enzymes, where the set of 1,3-BDO pathway enzymes are identified as above, namely: (a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase; (b) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase; (c) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase; (d) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase; (e) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase; (f) (1) a 2-amino-4-ketopentanoate (AKP) thiolase; (2) an AKP decarboxylase; (3) a 4-aminobutan-2-one ammonia-lyase; (4) a butanone hydratase; and (5) a 4-hydroxy-2-butanone reductase; (g) (1) a 2-amino-4-ketopentanoate (AKP) thiolase; (2) an AKP ammonia-lyase; (3) an acetylacrylate decarboxylase; (4) a butanone hydratase; and (5) a 4-hydroxy-2-butanone reductase; (h) (1) an acetoacetyl-CoA reductase (CoA-dependent, aldehyde forming); (2) a 3-oxobutyraldehyde reductase (ketone reducing); and (3) a 3-hydroxybutyraldehyde reductase; (i) (1) an acetoacetyl-CoA reductase (CoA dependent, alcohol forming) and (2) a 4-hydroxy-2-butanone reductase; (j) (1) an acetoacetyl-CoA reductase (CoA-dependent, aldehyde forming); (2) a 3-oxobutyraldehyde reductase (aldehyde reducing); and (3) a 4-hydroxy-2-butanone reductase; (k) (1) an acetoacetyl-CoA reductase (ketone reducing) and (2) a 3-hydroxybutyryl-CoA reductase (alcohol forming); (l) (1) an acetoacetyl-CoA reductase (ketone reducing); (2) a 3-hydroxybutyryl-CoA reductase (aldehyde forming); and (3) a 3-hydroxybutyraldehyde reductase; (m) (1) a 4-hydroxybutyryl-CoA dehydratase; (2) a crotonase; and (3) a 3-hydroxybutyryl-CoA reductase (alcohol forming); and (n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase.

Suitable purification and/or assays to test for the production of 1,3-butanediol can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see, for example, WO/2008/115840 and Hanai et al., *Appl. Environ. Microbiol.* 73:7814-7818 (2007)).

The 1,3-butanediol can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the 1,3-butanediol producers can be cultured for the biosynthetic production of 1,3-butanediol.

For the production of 1,3-butanediol, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in United States Publication No. US-2009-0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In addition to renewable feedstocks such as those exemplified above, the 1,3-butanediol microbial organisms of the invention also can be modified for growth on syngas as its source of carbon. In this specific embodiment, one or more proteins or enzymes are expressed in the 1,3-butanediol producing organisms to provide a metabolic pathway for utilization of syngas or other gaseous carbon source.

Organisms of the present invention can utilize, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 1,3-butanediol.

Accordingly, given the teachings and guidance provided herein, those skilled in the art will understand that a non-naturally occurring microbial organism can be produced that secretes the biosynthesized compounds of the invention when grown on a carbon source such as, syngas, CO and/or CO2. Such compounds include, for example, 1,3-butanediol and any of the intermediate metabolites in the 1,3-butanediol pathway. All that is required is to engineer in one or more of the required enzyme or protein activities to achieve biosynthesis of the desired compound or intermediate including, for example, inclusion of some or all of the 1,3-butanediol biosynthetic pathways. Accordingly, the invention provides a non-naturally occurring microbial organism that produces and/or secretes 1,3-butanediol when grown on a carbohydrate or other carbon source and produces and/or secretes any of the intermediate metabolites shown in the 1,3-butanediol pathway when grown on a carbohydrate or other carbon source. The 1,3-butanediol producing microbial organisms of the invention can initiate synthesis from an intermediate, for example, acetyl-CoA.

The non-naturally occurring microbial organisms of the invention are constructed using methods well known in the art as exemplified herein to exogenously express at least one nucleic acid encoding an 1,3-butanediol pathway enzyme or protein in sufficient amounts to produce 1,3-butanediol. It is understood that the microbial organisms of the invention are cultured under conditions sufficient to produce 1,3-butanediol. Following the teachings and guidance provided herein, the non-naturally occurring microbial organisms of the invention can achieve biosynthesis of 1,3-butanediol resulting in intracellular concentrations between about 0.1-2000 mM or more. Generally, the intracellular concentration of 1,3-butanediol is between about 3-1800 mM, particularly between about 5-1700 mM and more particularly between about 8-1600 mM, including about 100 mM, 200 mM, 500 mM, 800 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application No. US 2009/0047719, filed Aug. 10, 2007. Any of these conditions can be employed with the non-naturally occurring microbial organisms as well as other anaerobic conditions well known in the art. Under such anaerobic conditions, the 1,3-butanediol producers can synthesize 1,3-butanediol at intracellular concentrations of 5-10 mM or more as well as all other concentrations exemplified herein. It is understood that, even though the above description refers to intracellular concentrations, 1,3-butanediol producing microbial organisms can produce 1,3-butanediol intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 1,3-butanediol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 1,3-butanediol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 1,3-butanediol. Generally, and as with non-continuous culture procedures, the continuous and/or near-continuous production of 1,3-butanediol will include culturing a non-naturally occurring 1,3-butanediol producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 1,3-butanediol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 1,3-butanediol producers of the invention for continuous production of substantial quantities of 1,3-butanediol, the 1,3-butanediol producers also can be, for example, simultaneously subjected to chemical synthesis procedures to convert the product to other compounds or the product can be separated from the fermentation culture and sequentially subjected to chemical conversion to convert the product to other compounds, if desired.

In some embodiments, syngas can be used as a carbon feedstock. Important process considerations for a syngas fermentation are high biomass concentration and good gas-liquid mass transfer (Bredwell et al., *Biotechnol Prog.*, 15:834-844 (1999). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Fermentation products such as alcohols, organic acids, and residual glucose along with residual methanol are quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids. The growth rate is determined by measuring optical density using a spectrophotometer (600 nm). All piping in these systems is glass or metal to maintain anaerobic conditions. The gas sparging is performed with glass frits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

In order to achieve the overall target productivity, methods of cell retention or recycle are employed. One method to increase the microbial concentration is to recycle cells via a tangential flow membrane from a sidestream. Repeated batch culture can also be used, as previously described for production of acetate by *Moorella* (Sakai et al., *J Biosci. Bioeng*, 99:252-258 (2005)). Various other methods can also be used (Bredwell et al., *Biotechnol Prog.*, 15:834-844 (1999); Datar et al., *Biotechnol Bioeng*, 86:587-594 (2004)). Additional optimization can be tested such as overpressure at 1.5 atm to improve mass transfer (Najafpour et al., *Enzyme and Microbial Technology*, 38[1-2], 223-228 (2006)).

Once satisfactory performance is achieved using pure $H_2$/CO as the feed, synthetic gas mixtures are generated containing inhibitors likely to be present in commercial syngas. For example, a typical impurity profile is 4.5% $CH_4$, 0.1% $C_2H_2$, 0.35% $C_2H_6$, 1.4% $C_2H_4$, and 150 ppm nitric oxide (Datar et al., *Biotechnol Bioeng*, 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed et al., *Biotechnol Bioeng*, 97:1080-1086 (2007)). Cultures are tested in shake-flask cultures before moving to a fermentor. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, an adaptive evolution procedure is utilized to adapt cells to tolerate one or more impurities.

Advances in the field of protein engineering make it feasible to alter any of the enzymes disclosed herein to act efficiently on substrates not known to be natural to them. Below are several examples of broad-specificity enzymes from diverse classes of interest and and methods that have been used for evolving such enzymes to act on non-natural substrates.

One class of enzymes in the pathways disclosed herein is the oxidoreductases that interconvert ketones or aldehydes to alcohols (1.1.1). Enzymes in this class that can operate on a wide range of substrates. An alcohol dehydrogenase (1.1.1.1) purified from the soil bacterium *Brevibacterium* sp KU 1309 (Hirano et al., *J. Biosci. Bioeng.* 100:318-322 (2005)) was shown to operate on a plethora of aliphatic as well as aromatic alcohols with high activities. Table 33 shows the activity of the enzyme and its $K_m$ on different alcohols. The enzyme is reversible and has very high activity on several aldehydes also as shown in Table 34.

TABLE 33

| SUBSTRATE | RELATIVE ACTIVITY (%) | $K_M$ (MM) |
|---|---|---|
| 2-Phenylethanol | 100 | 0.025 |
| (S)-2-Phenylpropanol | 156 | 0.157 |
| (R)-2-Phenylpropanol | 63 | 0.020 |
| Benzyl alcohol | 199 | 0.012 |
| 3-Phenylpropanol | 135 | 0.033 |
| Ethanol | 76 | |
| 1-Butanol | 111 | |
| 1-Octanol | 101 | |
| 1-Dodecanol | 68 | |
| 1-Phenylethanol | 46 | |
| 2-Propanol | 54 | |

In this Table, the activity of 2-phenylethanol, corresponding to 19.2 U/mg, was taken as 100%.

TABLE 34

| SUBSTRATE | RELATIVE ACTIVITY (%) | $K_M$ (MM) |
|---|---|---|
| Phenylacetaldehyde | 100 | 0.261 |
| 2-Phenylpropionaldehyde | 188 | 0.864 |
| 1-Octylaldehyde | 87 | |
| Acetophenone | 0 | |

Lactate dehydrogenase (1.1.1.27) from *Ralstonia eutropha* is another enzyme that has been demonstrated to have high activities on several 2-oxoacids such as 2-oxobutyrate, 2-oxopentanoate and 2-oxoglutarate (a C5 compound analogous to 2-oxoadipate) (Steinbuchel et al., supra). Column 2 in Table 35 demonstrates the activities of ldhA from *R. eutropha* (formerly *A. eutrophus*) on different substrates (Steinbuchel et al., supra).

TABLE 35

| Substrate | Activity of L(+)-lactate dehydrogenase from *A. eustrophus* % | L(+)-lactate dehydrogenase from rabbit muscle | D(−)-lactate dehydrogenase from *L. leischmanii* |
|---|---|---|---|
| Glyoxylate | 8.7 | 23.9 | 5.0 |
| Pyruvate | 100.0 | 100.0 | 100.0 |
| 2-Oxobutyrate | 107.0 | 18.6 | 1.1 |
| 2-Oxovalerate | 125.0 | 0.7 | 0.0 |
| 3-Methyl-2-oxobutyrate | 28.5 | 0.0 | 0.0 |
| 3-Methyl-2-oxovalerate | 5.3 | 0.0 | 0.0 |
| 4-Methyl-2-oxopentanoate | 39.0 | 1.4 | 1.1 |

TABLE 35-continued

| Substrate | Activity of L(+)-lactate dehydrogenase from A. eustrophus % | L(+)-lactate dehydrogenase from rabbit muscle | D(-)-lactate dehydrogenase from L. leischmanii |
|---|---|---|---|
| Oxaloacetate | 0.0 | 33.1 | 23.1 |
| 2-Oxoglutarate | 79.6 | 0.0 | 0.0 |
| 3-Fluoropyruvate | 33.6 | 74.3 | 40.0 |

Oxidoreductases that can convert 2-oxoacids to their acyl-CoA counterparts (1.2.1) have been shown to accept multiple substrates as well. For example, branched-chain 2-keto-acid dehydrogenase complex (BCKAD), also known as 2-oxoisovalerate dehydrogenase (1.2.1.25), participates in branched-chain amino acid degradation pathways, converting 2-keto acids derivatives of valine, leucine and isoleucine to their acyl-CoA derivatives and $CO_2$. In some organisms including Rattus norvegicus (Paxton et al., Biochem. J. 234:295-303 (1986)) and Saccharomyces cerevisiae (Sinclair et al., Biochem. Mol. Biol. Int. 31:911-922 (1993)), this complex has been shown to have a broad substrate range that includes linear oxo-acids such as 2-oxobutanoate and alpha-ketoglutarate, in addition to the branched-chain amino acid precursors.

Members of yet another class of enzymes, namely aminotransferases (2.6.1), have been reported to act on multiple substrates. Aspartate aminotransferase (aspAT) from Pyrococcus fursious has been identified, expressed in E. coli and the recombinant protein characterized to demonstrate that the enzyme has the highest activities towards aspartate and alpha-ketoglutarate but lower, yet significant activities towards alanine, glutamate and the aromatic amino acids (Ward et al., Archaea. 1:133-141 (2002)). In another instance, an aminotransferase identified from Leishmania mexicana and expressed in E. coli Vernal et al., FEMS Microbiol. Lett. 229:217-222 (2003)) was reported to have a broad substrate specificity towards tyrosine (activity considered 100% on tyrosine), phenylalanine (90%), tryptophan (85%), aspartate (30%), leucine (25%) and methionine (25%) respectively (Vernal et al., Mol. Biochem. Parasitol. 96:83-92 (1998)). Similar broad specificity has been reported for a tyrosine aminotransferase from Trypanosoma cruzi, even though both of these enzymes have a sequence homology of only 6%. Note that the latter enzyme can accept leucine, methionine as well as tyrosine, phenylalanine, tryptophan and alanine as efficient amino donors (Nowicki et al., Biochim. Biophys. Acta 1546: 268-281 (2001)).

In contrast to these examples where the enzymes naturally have broad substrate specificities, numerous enzymes have been modified using directed evolution to broaden their specificity towards their non-natural substrates. Alternatively, the substrate preference of an enzyme has also been changed using directed evolution. For example, it has been reported that the enantioselectivity of a lipase from Pseudomonas aeruginosa was improved significantly. This enzyme hydrolyzed p-nitrophenyl 2-methyldecanoate with only 2% enantiomeric excess (ee) in favor of the (S)-acid. However, after four successive rounds of error-prone mutagenesis and screening, a variant was produced that catalyzed the requisite reaction with 81% ee Reetz et al., Angew. Chem. Int. Ed Engl. 36:2830-2832 (1997)).

Directed evolution methods have made possible the modification of an enzyme to function on an array of unnatural substrates. The substrate specificity of the lipase in P. aeruginosa was broadened by randomization of amino acid residues near the active site. This allowed for the acceptance of alpha-substituted carboxylic acid esters by this enzyme Reetz et al., Angew. Chem. Int. Ed Engl. 44:4192-4196 (2005)). In another successful attempt, DNA shuffling was employed to create an Escherichia coli aminotransferase that accepted β-branched substrates, which were poorly accepted by the wild-type enzyme (Yano et al., Proc. Natl. Acad. Sci. U.S.A 95:5511-5515 (1998)). Specifically, at the end of four rounds of shuffling, the activity of aspartate aminotransferase for valine and 2-oxovaline increased by up to five orders of magnitude, while decreasing the activity towards the natural substrate, aspartate, by up to 30-fold. Recently, an algorithm was used to design a retro-aldolase that could be used to catalyze the carbon-carbon bond cleavage in a non-natural and non-biological substrate, 4-hydroxy-4-(6-methoxy-2-naphthyl)-2-butanone. These algorithms used different combinations of four different catalytic motifs to design new enzymes and 20 of the selected designs for experimental characterization had four-fold improved rates over the uncatalyzed reaction (Jiang et al., Science 319:1387-1391 (2008)). Thus, not only are these engineering approaches capable of expanding the array of substrates on which an enzyme can act, but allow the design and construction of very efficient enzymes. For example, a method of DNA shuffling (random chimeragenesis on transient templates or RACHITT) was reported to lead to an engineered monooxygenase that had an improved rate of desulfurization on complex substrates as well as 20-fold faster conversion of a non-natural substrate (Coco et al. Nat. Biotechnol. 19:354-359 (2001)). Similarly, the specific activity of a sluggish mutant triosephosphate isomerase enzyme was improved up to 19-fold from 1.3 fold (Hermes et al., Proc. Natl. Acad. Sci. U.S.A 87:696-700 (1990)). This enhancement in specific activity was accomplished by using random mutagenesis over the whole length of the protein and the improvement could be traced back to mutations in six amino acid residues.

The effectiveness of protein engineering approaches to alter the substrate specificity of an enzyme for a desired substrate has also been demonstrated. Isopropylmalate dehydrogenase from Thermus thermophilus was modified by changing residues close to the active site so that it could now act on malate and D-lactate as substrates (Fujita et al., Biosci. Biotechnol Biochem. 65:2695-2700 (2001)). In this study as well as in others, it was pointed out that one or a few residues could be modified to alter the substrate specificity. A case in point is the dihydroflavonol 4-reductase for which a single amino acid was changed in the presumed substrate-binding region that could preferentially reduce dihydrokaempferol Johnson et al., Plant J. 25:325-333 (2001)). The substrate specificity of a very specific isocitrate dehydrogenase from Escherichia coli was changed form isocitrate to isopropylmalate by changing one residue in the active site (Doyle et al., Biochemistry 40:4234-4241 (2001)). In a similar vein, the cofactor specificity of a $NAD^+$-dependent 1,5-hydroxyprostaglandin dehydrogenase was altered to $NADP^+$ by changing a few residues near the N-terminal end Cho et al., Arch. Biochem. Biophys. 419:139-146 (2003)). Sequence analysis and molecular modeling analysis were used to identify the key residues for modification, which were further studied by site-directed mutagenesis.

A fucosidase was evolved from a galactosidase in E. coli by DNA shuffling and screening (Zhang et al., Proc Natl

*Acad Sci US.A* 94:4504-4509 (1997)). Similarly, aspartate aminotransferase from *E. coli* was converted into a tyrosine aminotransferase using homology modeling and site-directed mutagenesis (Onuffer et al., *Protein Sci.* 4:1750-1757 (1995)). Site-directed mutagenesis of two residues in the active site of benzoylformate decarboxylase from *P. putida* reportedly altered the affinity ($K_m$) towards natural and non-natural substrates Siegert et al., *Protein Eng Des Sel* 18:345-357 (2005)). Cytochrome c peroxidase (CCP) from *Saccharomyces cerevisiae* was subjected to directed molecular evolution to generate mutants with increased activity against the classical peroxidase substrate guaiacol, thus changing the substrate specificity of CCP from the protein cytochrome c to a small organic molecule. After three rounds of DNA shuffling and screening, mutants were isolated which possessed a 300-fold increased activity against guaiacol and up to 1000-fold increased specificity for this substrate relative to that for the natural substrate (Iffland et al., *Biochemistry* 39:10790-10798 (2000)).

In some cases, enzymes with different substrate preferences than both the parent enzymes have been obtained. For example, biphenyl-dioxygenase-mediated degradation of polychlorinated biphenyls was improved by shuffling genes from two bacteria, *Pseudomonas pseudoalcaligens* and *Burkholderia cepacia* (Kumamaru et al., *Nat. Biotechnol* 16, 663-666 (1998)). The resulting chimeric biphenyl oxygenases showed different substrate preferences than both the parental enzymes and enhanced the degradation activity towards related biphenyl compounds and single aromatic ring hydrocarbons such as toluene and benzene which were originally poor substrates for the enzyme.

It is not only possible to change the enzyme specificity but also to enhance the activities on those substrates on which the enzymes naturally have low activities. One study demonstrated that amino acid racemase from *P. putida* that had broad substrate specificity (on lysine, arginine, alanine, serine, methionine, cysteine, leucine and histidine among others) but low activity towards tryptophan could be improved significantly by random mutagenesis Kino et al., *Appl. Microbiol. Biotechnol.* 73:1299-1305 (2007)). Similarly, the active site of the bovine BCKAD was engineered to favor alternate substrate acetyl-CoA (Meng et al. *Biochemistry* 33:12879-12885 (1994)). An interesting aspect of these approaches is that even when random methods have been applied to generate these mutated enzymes with efficacious activities, the exact mutations or structural changes that confer the improvement in activity can be identified. For example, in the aforementioned study, the mutations that facilitated improved activity on tryptophan could be traced back to two different positions.

Directed evolution has also been used to express proteins that are difficult to express. For example, by subjecting the horseradish peroxidase to random mutagenesis and gene recombination, mutants could be extracted that had more than 14-fold activity than the wild type (Lin et al., *Biotechnol. Prog.* 15:467-471 (1999)).

A final example of directed evolution shows the extensive modifications to which an enzyme can be subjected to achieve a range of desired functions. The enzyme, lactate dehydrogenase from *Bacillus stearothermophilus* was subjected to site-directed mutagenesis, and three amino acid substitutions were made at sites that were indicated to determine the specificity towards different hydroxyacids (Clarke et al., *Biochem. Biophys. Res. Commun.* 148:15-23 (1987)). After these mutations, the specificity for oxaloacetate over pyruvate was increased to 500 in contrast to the wild type enzyme that had a catalytic specificity for pyruvate over oxaloacetate of 1000. This enzyme was further engineered using site-directed mutagenesis to have activity towards branched-chain substituted pyruvates (Wilks et al., *Biochemistry* 29:8587-8591 (1990)). Specifically, the enzyme had a 55-fold improvement in $K_{cat}$ for alpha-ketoisocaproate. Three structural modifications were made in the same enzyme to change its substrate specificity from lactate to malate. The enzyme was highly active and specific towards malate (Wilks et al., *Science* 242:1541-1544 (1988)). The same enzyme from *B. stearothermophilus* was subsequently engineered to have high catalytic activity towards alpha-keto acids with positively charged side chains, such as those containing ammonium groups (Hogan et al., *Biochemistry* 34:4225-4230 (1995)). Mutants with acidic amino acids introduced at position 102 of the enzyme favored binding of such side chain ammonium groups. The results obtained proved that the mutants showed up to 25-fold improvements in $k_{cat}/K_m$ values for omega-amino-alpha-keto acid substrates. This enzyme was also structurally modified to function as a phenyllactate dehydrogenase instead of a lactate dehydrogenase (Wilks et al., *Biochemistry* 31:7802-7806 (1992)). Restriction sites were introduced into the gene for the enzyme which allowed a region of the gene to be excised. This region coded for a mobile surface loop of polypeptide (residues 98-110) which normally seals the active site vacuole from bulk solvent and is a major determinant of substrate specificity. The variable length and sequence loops were inserted into the cut gene and used to synthesize hydroxyacid dehydrogenases with altered substrate specificities. With one longer loop construction, activity with pyruvate was reduced one-million-fold but activity with phenylpyruvate was largely unaltered. A switch in specificity ($k_{cat}/K_m$) of 390,000-fold was achieved. The 1700:1 selectivity of this enzyme for phenylpyruvate over pyruvate is that required in a phenyllactate dehydrogenase.

As indicated above, directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert, E. G., F. Baganz, H. C. Hailes, J. M. Ward, G. J. Lye, J. M. Woodley, and P. A. Dalby, 2005, Directed evolution of biocatalytic processes. Biomol. Eng 22:11-19; Huisman, G. W. and J. J. Lalonde, 2007, Enzyme evolution for chemical process applications, p. 717-742. In R. N. Patel (ed.), Biocatalysis in the pharmaceutical and biotechnology industries. CRC Press; Otten, L. G. and W. J. Quax. 2005. Directed evolution: selecting today's biocatalysts. Biomol. Eng 22:1-9; and Sen, S., D. Venkata, V, and B. Mandal, 2007, Developments in directed evolution for improving enzyme functions. Appl Biochem. Biotechnol 143:212-223.) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard, L., D. Come, D. Kell, J. Rowland, and M. Winson, 2005, A general model of error-prone PCR. J Theor. Biol 234:497-509.) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii, R., M. Kitaoka, and K. Hayashi, 2004, One-step random mutagenesis by error-prone rolling circle amplification. Nucleic Acids Res 32:e145; and Fujii, R., M. Kitaoka, and K. Hayashi, 2006, Error-prone rolling circle amplification: the simplest random mutagenesis protocol. Nat. Protoc. 1:2493-2497.) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, W. P. 1994, DNA shuffling by random fragmentation and reassembly: in vitro recombination for molecular evolution. Proc Natl Acad Sci US.A 91:10747-10751; and Stemmer, W. P. 1994. Rapid evolution of a protein in vitro by DNA shuffling. Nature 370:389-391.) typically involves digestion of 2 or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious random neutral mutations that might confer antigenicity.

Staggered Extension (StEP) (Zhao, H., L. Giver, Z. Shao, J. A. Affholter, and F. H. Arnold, 1998, Molecular evolution by staggered extension process (StEP) in vitro recombination. Nat. Biotechnol 16:258-261.) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao, Z., H. Zhao, L. Giver, and F. H. Arnold, 1998, Random-priming in vitro recombination: an effective tool for directed evolution. Nucleic Acids Res 26:681-683.) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov, A. A., Z. Shao, and F. H. Arnold. 1999. Recombination and chimeragenesis by in vitro heteroduplex formation and in vivo repair. Nucleic Acids Res 27:e18; and Volkov, A. A., Z. Shao, and F. H. Arnold. 2000. Random chimeragenesis by heteroduplex recombination. Methods Enzymol. 328:456-463.) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco, W. M., W. E. Levinson, M. J. Crist, H. J. Hektor, A. Darzins, P. T. Pienkos, C. H. Squires, and D. J. Monticello, 2001, DNA shuffling method for generating highly recombined genes and evolved enzymes. Nat. Biotechnol 19:354-359.) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee, S. H., E. J. Ryu, M. J. Kang, E.-S. Wang, Z. C. Y. Piao, K. J. J. Jung, and Y. Shin, 2003, A new approach to directed gene evolution by recombined extension on truncated templates (RETT). J. Molec. Catalysis 26:119-129.) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist, P. L. and M. D. Gibbs, 2007, Degenerate oligonucleotide gene shuffling. Methods Mol. Biol 352:191-204; Bergquist, P. L., R. A. Reeves, and M. D. Gibbs, 2005, Degenerate oligonucleotide gene shuffling (DOGS) and random drift mutagenesis (RNDM): two complementary techniques for enzyme evolution. Biomol. Eng 22:63-72; Gibbs, M. D., K. M. Nevalainen, and P. L. Bergquist, 2001, Degenerate oligonucleotide gene shuffling (DOGS): a method for enhancing the frequency of recombination with family shuffling. Gene 271:13-20.) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc Natl Acad Sci U.S.A.* 96:3562-3567 (1999); Ostermeier et al., 1999 *Nat. Biotechnol.* 17:1205-1209 (1999)) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is almost the same as ITCHY except that phosphothioate dNTPs are used to generate truncations. (Lutz, S., M. Ostermeier, and S. J. Benkovic, 2001, Rapid generation of incremental truncation libraries for protein engineering using alpha-phosphothioate nucleotides. Nucleic Acids Res 29:E16.) Relative to ITCHY, THIO-ITCHY can be easier to optimize, provide more reproducibility, and adjustability.

SCRATCHY-ITCHY combined with DNA shuffling is a combination of DNA shuffling and ITCHY; therefore, allowing multiple crossovers. (Lutz et al., *Proc Natl Acad Sci U.S.A.* 98:11248-11253 (2001).) SCRATCHY combines the best features of ITCHY and DNA shuffling. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng.* 22:63-72 (2005).) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J.* 3:74-82 (2008); Wong *Nucleic Acids Res* 32:e26; Wong et al., *Anal. Biochem.* 341:187-189 (2005).) Using this technique it can be possible to generate a large library of mutants within 2-3 days using simple methods. This is very non-directed compared to mutational bias of DNA polymerases. Differences in this approach makes this technique complementary (or alternative) to epPCR.

In Synthetic Shuffling, overlapping oligonucleotides are designed to encode "all genetic diversity in targets" and allow a very high diversity for the shuffled progeny. (Ness, et al., *Nat. Biotechnol* 20:1251-1255 (2002).) In this technique, one can design the fragments to be shuffled. This aids in increasing the resulting diversity of the progeny. One can design sequence/codon biases to make more distantly related sequences recombine at rates approaching more closely related sequences and it doesn't require possessing the template genes physically.

Nucleotide Exchange and Excision Technology NexT exploits a combination of dUTP incorporation followed by treatment with uracil DNA glycosylase and then piperidine to perform endpoint DNA fragmentation. (Muller et al., *Nucleic Acids Res* 33:e117 (2005)) The gene is reassembled using internal PCR primer extension with proofreading polymerase. The sizes for shuffling are directly controllable using varying dUPT::dTTP ratios. This is an end point reaction using simple methods for uracil incorporation and cleavage. One can use other nucleotide analogs such as 8-oxo-guanine with this method. Additionally, the technique works well with very short fragments (86 bp) and has a low error rate. Chemical cleavage of DNA means very few unshuffled clones.

In Sequence Homology-Independent Protein Recombination (SHIPREC) a linker is used to facilitate fusion between 2 distantly/unrelated genes; nuclease treatment is used to generate a range of chimeras between the two. Result is a single crossover library of these fusions. (Sieber, V., C. A.

Martinez, and F. H. Arnold. 2001. Libraries of hybrid proteins from distantly related sequences. Nat. Biotechnol 19:456-460.) This produces a limited type of shuffling; mutagenesis is a separate process. This technique can create a library of chimeras with varying fractions of each of 2 unrelated parent genes. No homology is needed. SHIPREC was tested with a heme-binding domain of a bacterial CP450 fused to N-terminal regions of a mammalian CP450; this produced mammalian activity in a more soluble enzyme.

In Gene Site Saturation Mutagenesis (GSSM) the starting materials are a supercoiled dsDNA plasmid with insert and 2 primers degenerate at the desired site for mutations. (Kretz, K. A., T. H. Richardson, K. A. Gray, D. E. Robertson, X. Tan, and J. M. Short, 2004, Gene site saturation mutagenesis: a comprehensive mutagenesis approach. Methods Enzymol. 388:3-11.) Primers carry the mutation of interest and anneal to the same sequence on opposite strands of DNA; mutation in the middle of the primer and ~20 nucleotides of correct sequence flanking on each side. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (i.e., one codon). The technique facilitates the generation of all possible replacements at one site with no nonsense codons and equal or near-equal representation of most possible alleles. It does not require prior knowledge of structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson, J. F., J. U. Bowie, R. M. Breyer, J. C. Hu, K. R. Knight, W. A. Lim, M. C. Mossing, D. A. Parsell, K. R. Shoemaker, and R. T. Sauer, 1991, Random mutagenesis of protein sequences using oligonucleotide cassettes. Methods Enzymol. 208:564-586; and Reidhaar-Olson, J. F. and R. T. Sauer, 1988, Combinatorial cassette mutagenesis as a probe of the informational content of protein sequences. Science 241:53-57.) Simultaneous substitutions at 2 or 3 sites are possible using this technique. Additionally, the method tests a large multiplicity of possible sequence changes at a limited range of sites. It has been used to explore the information content of lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz, M. T., S. Wilensek, D. Zha, and K. E. Jaeger, 2001, Directed Evolution of an Enantioselective Enzyme through Combinatorial Multiple-Cassette Mutagenesis. Angew. Chem. Int. Ed Engl. 40:3589-3591.) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional is mutator plasmids allow increases of 20- to 4000-× in random and natural mutation frequency during selection and to block accumulation of deleterious mutations when selection is not required. (Selifonova, O., F. Valle, and V. Schellenberger, 2001, Rapid evolution of novel traits in microorganisms. Appl Environ Microbiol 67:3645-3649.) This technology is based on a plasmid-derived mutD5 gene, which encodes a mutant subunit of DNA polymerase III. This subunit binds to endogenous DNA polymerase III and compromises the proofreading ability of polymerase III in any of the strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows plasmid curing at 41° C. It should be noted that mutator strains have been explored for quite some time (e.g., see Winter and coworkers, 1996, *J. Mol. Biol.* 260, 359-3680. In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal, A., N. Beyaz, L. Haber, G. Cappuccilli, H. Yee, R. R. Bhatt, T. Takeuchi, R. A. Lerner, and R. Crea, 2005, A general method for greatly improving the affinity of antibodies by using combinatorial libraries. Proc Natl Acad Sci US.A 102:8466-8471.) Rather than saturating each site with all possible amino acid changes, a set of 9 is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and should increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (on the world-wide web at www.verenium.com/Pages/Technology/EnzymeTech/TechEnzyTGR.html) Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM, a large range of mutations can be tested for improved activity. The method allows "blending" and "fine tuning" of DNA shuffling, e.g. codon usage can be optimized.

In Silico Protein Design Automation PDA is an optimization algorithm that anchors the structurally defined protein backbone possessing a particular fold, and searches sequence space for amino acid substitutions that can stabilize the fold and overall protein energetics. (Hayes, R. J., J. Bentzien, M. L. Ary, M. Y. Hwang, J. M. Jacinto, J.

Vielmetter, A. Kundu, and B. I. Dahiyat, 2002, Combining computational and experimental screening for rapid optimization of protein properties. Proc Natl Acad Sci US.A 99:15926-15931.) This technology allows in silico structure-based entropy predictions in order to search for structural tolerance toward protein amino acid variations. Statistical mechanics is applied to calculate coupling interactions at each position—structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). Choice of sequence variants to test is related to predictions based on most favorable thermodynamics and ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves 1) Use knowledge of structure/function to choose a likely site for enzyme improvement. 2) Saturation mutagenesis at chosen site using Stratagene QuikChange (or other suitable means). 3) Screen/select for desired properties. 4) With improved clone(s), start over at another site and continue repeating. (Reetz, M. T. and J. D. Carballeira, 2007, Iterative saturation mutagenesis (ISM) for rapid directed evolution of functional enzymes. Nat. Protoc. 2:891-903; and Reetz, M. T., J. D. Carballeira, and A. Vogel, 2006, Iterative saturation mutagenesis on the basis of B factors as a strategy for increasing protein thermostability. Angew. Chem. Int. Ed Engl. 45:7745-7751.) This is a proven methodology assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,3-butanediol.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. 2002/0168654, WO 2002/055995, and U.S. 2009/0047719.

Another computational method for identifying and designing metabolic alterations favoring biosynthetic production of a product is a metabolic modeling and simulation system termed SimPheny®. This computational method and system is described in, for example, U.S. 2003/0233218, filed Jun. 14, 2002, and in WO/2003/106998. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also included within the definition of the invention provided herein. Accordingly, the following examples are intended to illustrate but not limit the present invention.

Example I 1,3-Butanediol Synthesis Via Alanine

This example describes the generation of a microbial organism capable of producing 1,3-butanediol using the alanine pathway in FIG. 1 via Steps A, B, C, D and H.

Escherichia coli is used as a target organism to engineer a 1,3-butanediol-producing pathway as shown in FIG. 1. *E. coli* provides a good host for generating a non-naturally occurring microorganism capable of producing 1,3-butanediol. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 1,3-butanediol, nucleic acids encoding the enzymes utilized in the alanine pathway as described previously, are expressed in *E. coli* using well known molecular biology techniques (see, for example, Sambrook, supra, 2001; Ausubel supra, 1999; Roberts et al., supra, 1989).

In particular, the ortA (YP_001086914.1), ortB (YP_001086915.1), dat (P19938), and pdc (P06672) genes encoding the AKP thiolase, AKP aminotransferase and 2,4-dioxopentanoate decarboxylase activities, respectively, are cloned into the pZE13 vector (Expressys, Ruelzheim, Germany) under the PA1/lacO promoter. In addition, the yqhD (NP_417484.1) and adh (AAA23199.2) genes encoding 3-oxobutyraldehye reductase (aldehyde reducing) and 4-hydroxy,2-butanone reductase, respectively are cloned into the pZA33 vector (Expressys, Ruelzheim, Germany) under the PA1/lacO promoter. The two sets of plasmids are transformed into *E. coli* strain MG1655 to express the proteins and enzymes required for 1,3-butanediol synthesis via the alanine pathway. Note that *E. coli* possesses the ability to form D-alanine.

The resulting genetically engineered organism is cultured in glucose containing medium following procedures well known in the art (see, for example, Sambrook et al., supra, 2001). The expression of alanine pathway genes is corroborated using methods well known in the art for determining polypeptide expression or enzymatic activity, including for example, Northern blots, PCR amplification of mRNA, immunoblotting. Enzymatic activities of the expressed enzymes are confirmed using assays specific for the individually activities. The ability of the engineered *E. coli* strain to produce 1,3-butanediol is confirmed using HPLC, gas chromatography-mass spectrometry (GCMS) or liquid chromatography-mass spectrometry (LCMS).

Microbial strains engineered to have a functional 1,3-butanediol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of 1,3-butanediol. One modeling method is the bilevel optimization approach, OptKnock (Burgard et al., *Biotechnol. Bioengineer*. 84:647-657 (2003)), which is applied to select gene knockouts that collectively result in better production of 1,3-butanediol. Adaptive evolution also can be used to generate better producers of, for example, alanine or 2-amino-4-oxopentanoate intermediates or the 1,3-butanediol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 1,3-butanediol producer to further increase production.

For large-scale production of 1,3-butanediol, the above alanine pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example II 1,3-BDO Synthesis Using Acetoacetyl-CoA as the Intermediate

This Example describes the generation of a microbial organism capable of producing 1,3-butanediol using acetoacetyl-CoA as the precursor (Steps G, H and I in FIG. 2).

*Escherichia coli* is used as a target organism to engineer the pathway through Steps G (conversion of acetoacetyl-CoA into 3-hydroxybutyryl-CoA), H (conversion of 3-hydroxybutyryl-CoA into 3-hydroxybutyraldehyde) and I (conversion of 3-hydroxybutyraldehyde into 1,3-butanediol) in FIG. 2. *E. coli* provides a good host for generating a non-naturally occurring microorganism capable of producing 1,3-butanediol. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 1,3-butanediol, nucleic acids encoding the enzymes utilized in the disclosed pathway (Steps G, H and I) as described previously, are expressed in *E. coli* using well known molecular biology techniques (see, for example, Sambrook, supra, 2001; Ausubel supra, 1999; Roberts et al., supra, 1989). Note that *E. coli* has a native thiolase encoded by atoB (Accession number: NP_416728.1) that condenses two molecules of acetyl-CoA to form acetoacetyl-CoA.

Further, hbd (NP_349314.1) encoding acetoacetyl-CoA reductase (ketone reducing), is cloned into the pZE13 vector (Expressys, Ruelzheim, Germany) under the PA1/lacO promoter. The plasmid is transformed into *E. coli* strain MG1655 to express the enzyme required for the formation of 3-hydroxybutyryl-CoA via acetoacetyl-CoA. An aldehyde dehydrogenase (selected from Table A below) that converts 3-hydroxybutyryl-CoA into 3-hydroxybutyraldehyde, and an alcohol dehydrogenase (selected from Table B below) that further reduces 3-hydroxybutyraldehyde into 1,3-BDO are also cloned into the pZE13 vector under the PA1/lacO promoter.

The resulting genetically engineered organism is cultured in glucose containing medium following procedures well known in the art (see, for example, Sambrook et al., supra, 2001). The expression of the pathway genes is corroborated using methods well known in the art for determining polypeptide expression or enzymatic activity, including, for example, Northern blots, PCR amplification of mRNA, immunoblotting. Enzymatic activities of the expressed enzymes are confirmed using assays specific for the individually activities. The ability of the engineered E. coli strain to produce 1,3-butanediol is confirmed using HPLC, gas chromatography-mass spectrometry (GCMS) or liquid chromatography-mass spectrometry (LCMS).

Microbial strains engineered to have a functional 1,3-butanediol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of 1,3-butanediol. One modeling method is the bilevel optimization approach, OptKnock (Burgard et al., *Biotechnol. Bioengineer.* 84:647-657 (2003)), which is applied to select gene knockouts that collectively result in better production of 1,3-butanediol. Adaptive evolution also can be used to generate better producers of, for example, the acetyl-CoA intermediate or the 1,3-butanediol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 1,3-butanediol producer to further increase production.

For large-scale production of 1,3-butanediol, the recombinant organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids (Lin et al., *Biotechnol. Bioeng.*, 90:775-779 (2005)).

Several aldehyde dehydrogenases were tested for activity on 3-hydroxybutyryl-CoA. Crude lysates of bacteria, each strain carrying one out of six genes listed in Table A below encoding for an aldehyde dehydrogenase was tested for activity on 3-hydroxybutyryl-CoA by measuring the release of CoA moiety. The genes that were tested and were found to have significant activity on 3-HBCoA encode the proteins with the following accession and GI numbers:

TABLE A

| Protein | GenBank ID | GI Number | Organism |
|---|---|---|---|
| bld | AAP42563.1 | 31075383 | *Clostridium saccharoperbutylacetonicum* |
| ald | ACL06658.1 | 1. 218764192 | *Desulfatibacillum alkenivorans* AK-01 |
| ald | YP_001452373 | 2. 157145054 | *Citrobacter koseri* ATCC BAA-895 |
| pduP | 3. NP_460996.1 | 4. 16765381 | *Salmonella enterica Typhimurium* |
| pduP | 5. ABJ64680.1 | 6. 116099531 | *Lactobacillus brevis* ATCC 367 |
| 7. BselDRAFT_1651 | 8. ZP_02169447 | 9. 163762382 | *Bacillus selenitireducens* MLS10 |

Figure 4:
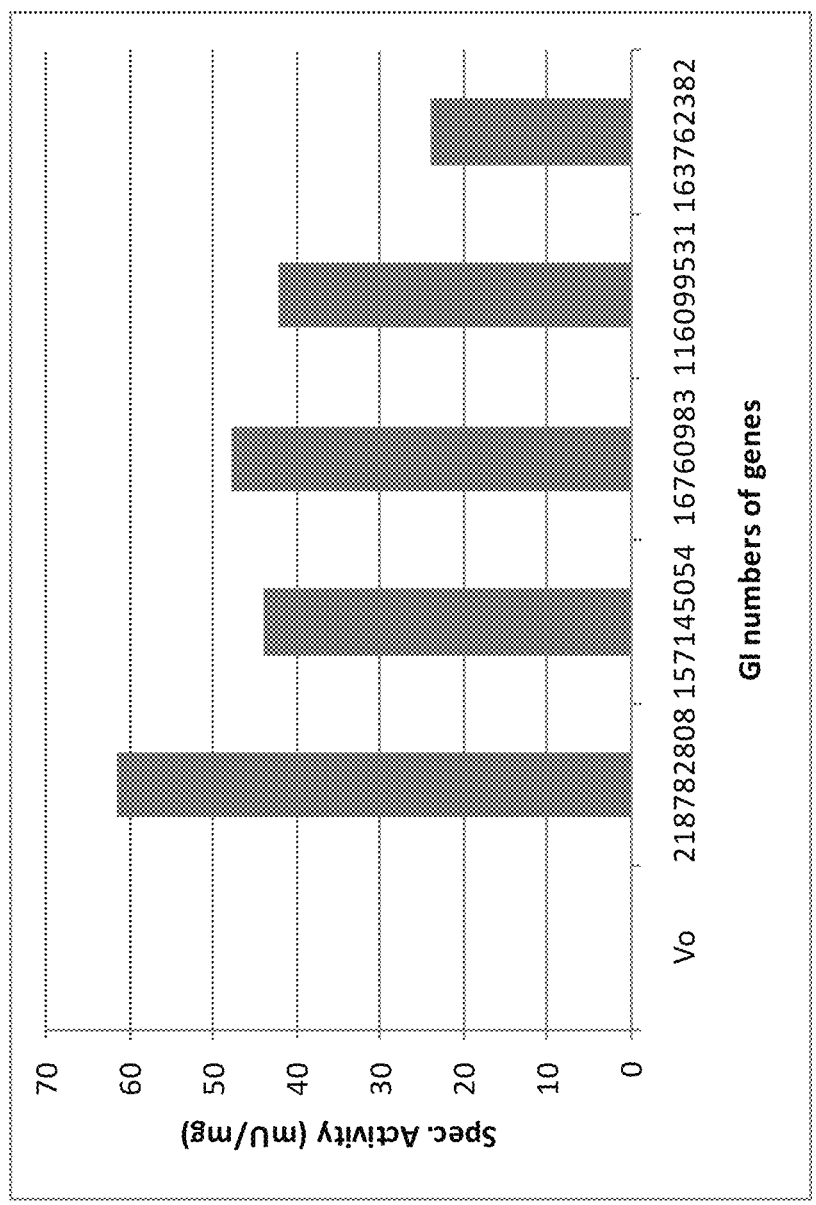
FIG. 4 shows aldehyde dehydrogenases showing significant activity on 3-hydroxybutyl-CoA.

To correct for background activity in the lysate, measured activities were compared to a negative control without ALD gene (vector only, "Vo"). FIG. 4 shows the specific activity of each of the tested genes on 3-hydroxybutyryl-CoA. The gene ids are shown on the x-axis.

Figure 5:
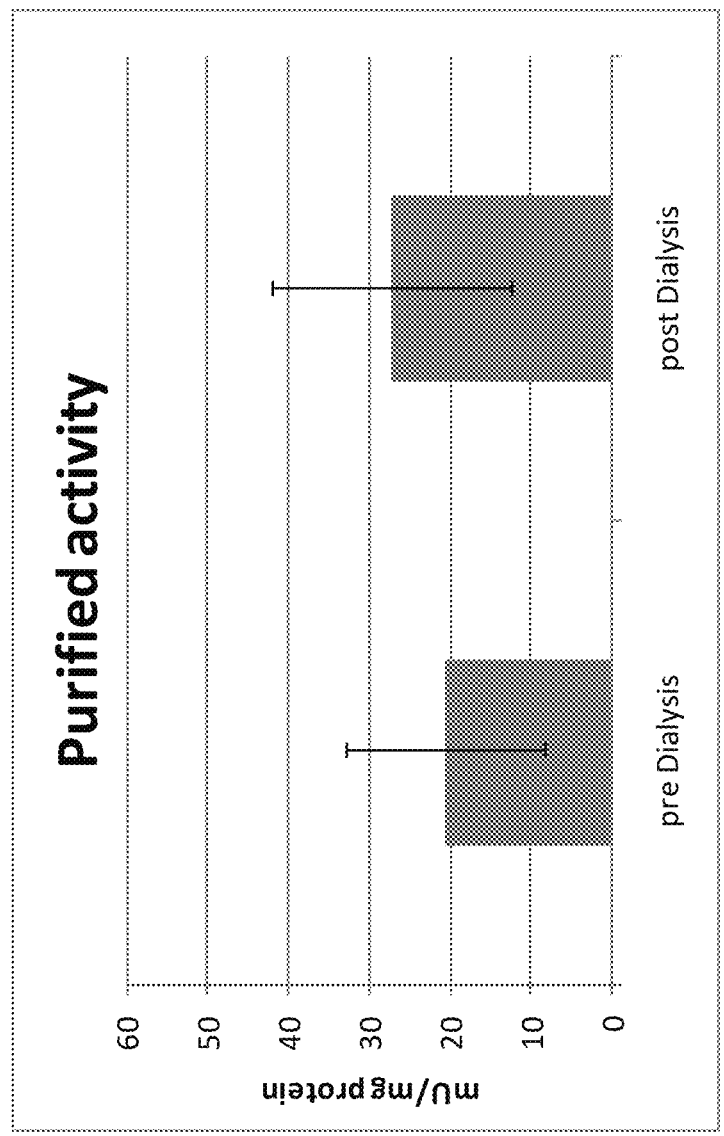
FIG. 5 shows the specific activity of bld from *Clostridium saccharoperbutylacetonicum* on 3-Hydroxybutyryl-CoA before and after dialysis.

Further, bld (GenBank ID: AAP42563.1, GI number: 31075383) was also tested for activity on 3-HBCoA. The following FIG. 5 shows the activity of the gene on 3-hydroxybutyryl-CoA before and after dialysis.

Alcohol dehydrogenases that were tested for activity on 3-hydroxybutyraldehyde and demonstrated to have significant activity are listed below.

TABLE B

| Protein | GenBank ID | GI Number | Organism |
|---|---|---|---|
| Bdh (Cbei_2181) | YP_001309304 | 150017050 | *Clostridium beijerinckii* |
| Bdh (Cbei_1722) | YP_001309535.1 | 150016596 | *Clostridium beijerinckii* |
| Bdh (Cbei_2421) | YP_001309535.1 | 150017281 | *Clostridium beijerinckii* |

The following protocol was used to demonstrate alcohol dehydrogenase activity (i.e., conversion of 3-hydroxybutyraldehyde to 1,3-BDO) and combined aldehyde and alcohol dehydrogenase activities (i.e., conversion of 3-hydroxybutyryl-CoA into 1,3-BDO).

Chemically competent cells were transformed with plasmids containing either an aldehyde dehydrogenase or an alcohol dehydrogenase (listed in Tables A and B above). Colonies from the plates were picked and grown in LB plus 100 ug/ml carbenecillin overnight, then 0.6 mL was used to inoculate 60 mL culture of each alcohol dehydrogenase, or 1.5 mL was used to inoculate a 500 mL culture of each aldehyde dehydrogenase. Cells were grown at 37° C. to an O.D. of ~0.7 and induced with IPTG. The cultures were incubated at 30° C. during protein expression for 4 hours. The cell cultures were divided into 30 ml aliquots, centrifuged and the cell pellets were stored at −80° C. A sample of the cell culture was used to estimate final cell density.

Combinations of alcohol dehydrogenases and aldehyde dehydrogenases were screened in a 96-well plate format with 3-hydroxybutyryl-CoA as a substrate plus a control (no substrate). Alternatively, for testing the alcohol dehydrogenases activity, only the alcohol dehydrogenases were added with and without the substrate, 3-hydroxybutyraldehyde. Preparation of cell lysates was performed on ice in the coldroom (4° C.). Final cell density was used to calculate the quantity of Bug Buster cell lysis reagent for each cell pellet. Lysozyme (10 uL) and benzonase (10 uL) were added to 35 ml bugbuster and gently inverted to mix. First, 50 μm of dithiothreitol (100 mM stock) was added to the pellet, then 0.5 ml per O.D. of 1.0 (at 600 nm) of the Bug Buster plus enzyme mixture was added to the cell pellet and gently mixed to resuspend.

To each well, 50 ul of 1 M MOPS (pH=7.5), and 25 ul of cofactor mixture (4 mM NADH and 4 mM NADPH), both 100 uL aldehyde dehydrogenase cell lysate, 150 uL alcohol dehydrogenase cell lysate or only 150 uL alcohol dehydrogenase cell lysate was added and gently mixed. Then, the relevant substrate was added to the wells. 25 mg of 3-hydroxybutyryl CoA was resuspended in 250 uL water and 5 ul was added to each well testing for both alcohol and aldehyde dehydrogenase activities for a final concentration of 1.8 mM. For testing only the alcohol dehydrogenase activity, 50 uL of 3-hydroxybutyraldehyde (prepared by mixing 0.6 ml acetaldehyde in 5 ml water plus catalytic base (one pellet of NaOH) Guthrie, J. P. (reference attached) was added to each well. The final concentration of 3-hydroxybutyraldehyde in each well was approximately 50 mM. The 96-deepwell plate was sealed with a plastic PCR seal and incubated at 30° C. shaking overnight (18 hours total). Because protein and cell debris form precipitates during the incubation period, the plates were centrifuged for 10 min at 4500×g, and the supernate was filtered through a Whatman 96-well filter plate (0.45 μm) prior to LC-MS analysis. Samples were analyzed for 1,3-butanediol formation.

Figure 6:
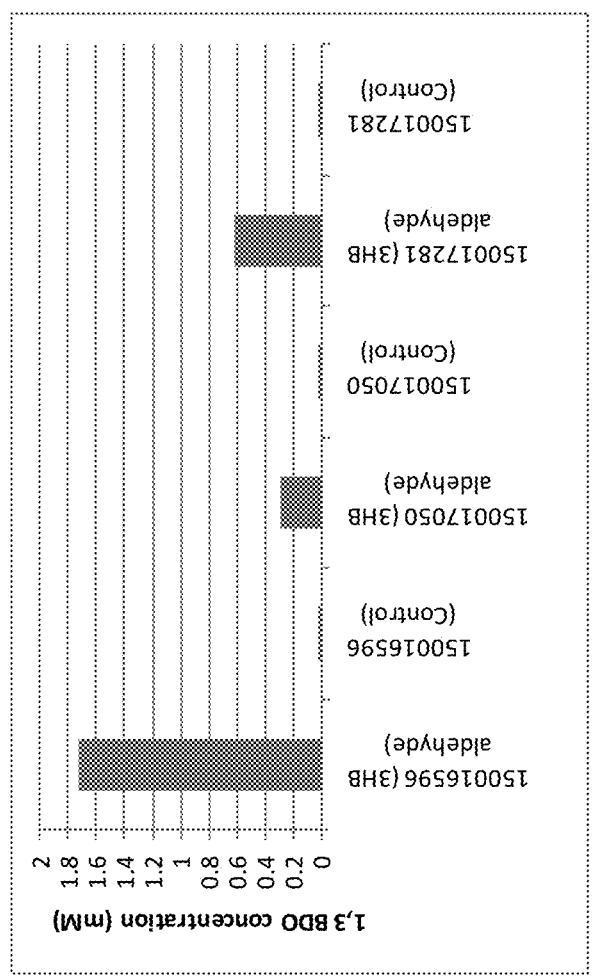
FIG. 6 shows 1,3-BDO concentrations when 3-hydroxybutyraldehyde was added as a substrate and in the control samples with no substrate. The GI numbers for the alcohol dehydrogenases are shown.

FIG. 6 shows 1,3-BDO concentrations when 3-hydroxybutyraldehyde was added as a substrate and in the control samples with no substrate. The GI numbers for the alcohol dehydrogenases are shown.

Figure 7:
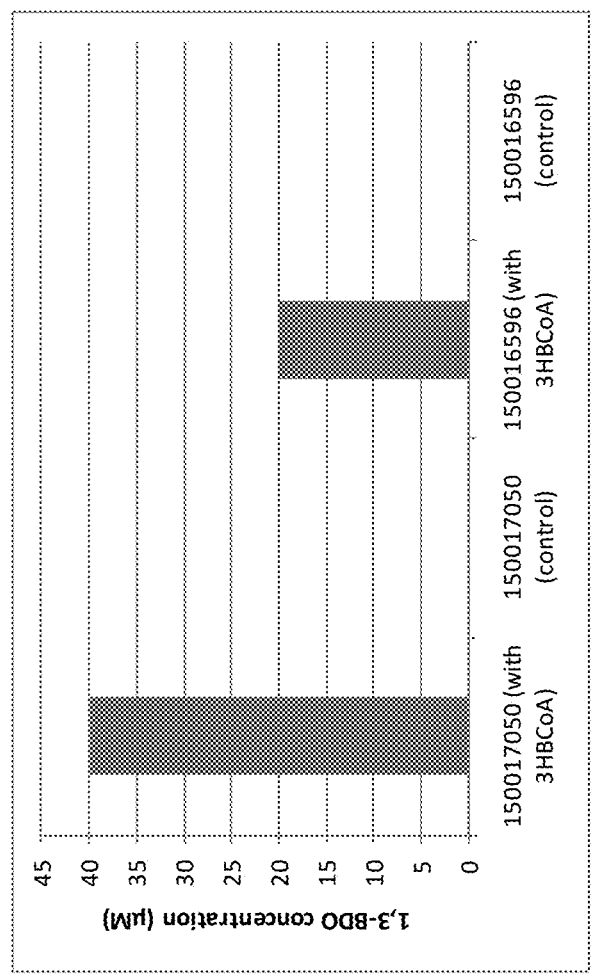
FIG. 7 shows 1,3-BDO concentrations when 3-hydroxybutyryl-CoA was added as a substrate and in the control samples with no substrate. The GI numbers for the alcohol dehydrogenases are shown. The GI number for the aldehyde dehydrogenase tested in conjunction is 163762382.

FIG. 7 shows 1,3-BDO concentrations when 3-hydroxybutyryl-CoA was added as a substrate and in the control samples with no substrate. The GI numbers for the alcohol dehydrogenases are shown. The GI number for the aldehyde dehydrogenase tested in conjunction is 163762382.

Example III 1,3-BDO Synthesis Using 4-Hydroxybutyryl-CoA as the Intermediate

This Example describes the generation of a microbial organism capable of producing 1,3-butanediol using 4-hydroxybutyryl-CoA as the precursor (Steps A, B and E in FIG. 3).

Escherichia coli is used as a target organism to engineer the pathway through Steps A, B and E in FIG. 3. E. coli provides a good host for generating a non-naturally occurring microorganism capable of producing 1,3-butanediol. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce 1,3-butanediol, nucleic acids encoding the enzymes utilized in the disclosed pathway (Steps A, B and E) as described previously, are expressed in E. coli using well known molecular biology techniques (see, for example, Sambrook, supra, 2001; Ausubel supra, 1999; Roberts et al., supra, 1989). A recombinant strain that has been engineered to produce significant quantities of 4-hydroxybutyryl-CoA has been described by the applicants previously (Burk et al. (US 20090075351) and will be used for inserting the proposed pathway to 1,3-butanediol.

Further, abfD (YP_3001396399.1), crt (NP_349318.1) and adhE2 (AAK09379.1) genes encoding 4-hydroxybutyryl-CoA dehydratase, crotonase and 3-hydroxybutyryl-CoA reductase (alcohol forming) activities respectively, are cloned into the pZE13 vector (Expressys, Ruelzheim, Germany) under the PA1/lacO promoter. The plasmid is transformed into the recombinant E. coli strain producing 4-hydroxybutyryl-CoA to express the proteins and enzymes required for 1,3-butanediol synthesis from this metabolite.

The resulting genetically engineered organism is cultured in glucose containing medium following procedures well known in the art (see, for example, Sambrook et al., supra, 2001). The expression of the pathway genes is corroborated using methods well known in the art for determining polypeptide expression or enzymatic activity, including, for example, Northern blots, PCR amplification of mRNA, immunoblotting. Enzymatic activities of the expressed enzymes are confirmed using assays specific for the individually activities. The ability of the engineered E. coli strain to produce 1,3-butanediol is confirmed using HPLC, gas chromatography-mass spectrometry (GCMS) or liquid chromatography-mass spectrometry (LCMS).

Microbial strains engineered to have a functional 1,3-butanediol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of 1,3-butanediol. One modeling method is the bilevel optimization approach, OptKnock (Burgard et al., *Biotechnol. Bioengineer.* 84:647-657 (2003)), which is applied to select gene knockouts that collectively result in better production of 1,3-butanediol. Adaptive evolution also can be used to generate better producers of, for example, the acetyl-CoA intermediate or the 1,3-butanediol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 1,3-butanediol producer to further increase production.

For large-scale production of 1,3-butanediol, the recombinant organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as $H_2SO_4$. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids (Lin et al., *Biotechnol Bioeng.* 90:775-779 (2005))

TABLE 36

(Ref: FIG. 1)

| Step | EC class | Desired substrate | Desired product | Enzyme name | Gene name | GenBank ID (if available) | Organism | Known Substrates |
|---|---|---|---|---|---|---|---|---|
| A | 2.3.1.b | D-alanine | 2-amino-4-oxo-pentanoate | AKP Thiolase | ortA | YP_001086914.1 | *Clostridium difficile* 630 | D-alanine |
| | | | | | ortB | YP_001086915.1 | *Clostridium difficile* 630 | D-alanine |
| | | | | | Amet_2368 | YP_001320181.1 | *Alkaliphilus metalliredigenes* QYF | D-alanine |
| | | | | | Amet_2369 | YP_001320182.1 | *Alkaliphilus metalliredigenes* QYF | D-alanine |
| | | | | | Teth514_1478 | YP_001663101.1 | *Thermoanaerobacter* sp. X514 | D-alanine |
| | | | | | Teth514_1479 | YP_001663102.1 | *Thermoanaerobacter* sp. X514 | D-alanine |
| B | 2.6.1.a | 2-amino-4-oxo-pentanoate | 2,4-oxo-pentanoate | 2-amino-4-oxopentanoate aminotransferase or oxidoreductase (deaminating) | aspC | NP_415448.1 | *Escherichia coli* | L-aspartate |
| | | | | | avtA | YP_026231.1 | *Escherichia coli* | L-alanine, L-valine |
| | | | | | AAT2 | P23542.3 | *Saccharomyces cerevisae* | L-aspartate |
| | | | | | dat | P19938 | *Bacillus* sp. YM-1 | D-alanine, D-2-aminobutanoate, D-aspartate |
| | | | | | dat | O07597 | *Bacillus subtilis* | D-alanine, D-2-aminobutanoate, D-aspartate |
| | | | | | ldh | P0A393 | *Bacillus cereus* | L-leucine, L-valine, 2-aminobutanoate, L-isoleucine |
| | | | | | nadX | NP_229443.1 | *Thermotoga maritima* | L-aspartate |
| C | 4.1.1.a | 2,4-dioxo-pentanoate | 3-oxobutanal | 2,4-dioxo-pentanoate decarboxylase | pdc | P06672.1 | *Zymomonas mobilus* | 2-ketobutyrate |
| | | | | | pdc1 | P06169 | *Saccharomyces cerevisae* | 2-ketobutyrate, 3-hydroxypyruvate |
| | | | | | mdlC | P20906.2 | *Pseudomonas putdia* | 2-ketobutyrate |
| | | | | | kgd | O50463.4 | *Mycobacterium tuberculosis* | alpha-ketoglutarate |
| D | 1.1.1.a | 3-oxobutyraldehyde | 4-hydroxy, 2-butanone | 3-oxobutyraldehyde reductase (aldehyde reducing) | alrA | BAB12273.1 | *Acinetobacter* sp. Strain M-1 | C2-C14 aldehydes |

TABLE 36-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| | | | | | ADH2 | NP_014032.1 | *Saccharymyces cerevisiae* | propionaldehyde, isobutyraldehyde, butyraldehyde, 2-methylbu-tyraldehyde, 3-methylbu-tyraldehyde, 2-phenylac-etaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |
| | | | | | ADHI | AAR91477.1 | *Geobacillus thermogluco-sidasius* M10EXG | ethanol, 1-butanol, 1-pentanol, 1-heptanol, 1-hexanol, 1-octanol, 2-propanol |
| | | | | | mmsb | P28811.1 | *Pseudomonas aeruginosa* | 3-hydroxybu-tyraldehydre, malonic semialdehyde, methylmalonate semialdehyde |
| | | | | | P84067 | P84067 | *Thermus thermophilus* | methylmalonate semialdehyde |
| E | 4.1.1.a | 2-amino-4-oxo-pentanoate | 4-ami-nobutan-2-one | 2-amino-4-oxopentanoate decarboxylase | lysA | NP_417315.1 | *Escherichia coli* | meso-diaminopimelate |
| | | | | | lysA | AAA25361.1 | *Mycobacterium tuberculosis* | meso-diaminopimelate |
| | | | | | lysA | BAC92756.1 | *Methylophilus methylotrophus* | meso-diaminopimelate |
| | | | | | odc1 | AA59967.1 | *Homo sapiens* | D-ornithine |
| | | | | | panD | P0A790 | *Escherichia coli* | L-aspartate |
| | | | | | panD | Q9X4N0 | *Corynebacterium glutanicum* | L-aspartate |
| | | | | | panD | P65660 | *Mycobacterium tuberculosis* | L-aspartate |
| F | 4.3.1.a | 4-ami-nobutan-2-one | butenone | 4-ami-nobutan-2-one ammonia lyase | aspA | NP_418562 | *Escherichia coli* K12 subsp. MG1655 | L-aspartate |
| | | | | | aspA | P44324.1 | *Haemophilus influenzae* | L-aspartate |
| | | | | | aspA | P07346.1 | *Pseudomonas fluorescens* | L-aspartate |
| | | | | | ansB | P26899.1 | *Bacillus subtilus* | L-aspartate |
| | | | | | aspA | P33109.1 | *Serratia marcescens* | L-aspartate |
| G | 4.2.1.a | butenone | 4-hydroxy,2-butanone | butenone hydratase | fumA | P0AC33 | *Escherichia coli* K12 | fumarate |
| | | | | | fumC | P05042 | *Escherichia coli* K12 | fumarate |
| | | | | | fumC | O69294 | *Campylobacter jejuni* | fumarate |
| | | | | | fumC | P84127 | *Thermus thermophilus* | fumarate |
| | | | | | fumH | P14408 | *Rattus norvegicus* | fumarate |
| | | | | | hmd | ABC88407.1 | *Eubacterium barkeri* | 2-methylene-glutarate |
| | | | | | dmdA | ABC88408 | *Eubacterium barkeri* | dimethylmaleate |
| | | | | | dmdB | ABC88409.1 | *Eubacterium barkeri* | dimethylmaleate |

TABLE 36-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| H | 1.1.1.a | 4-hydroxy, 2-butanone | 1,3-butanediol | 4-hydroxy, 2-butanone reductase | bdh | AAA58352.1 | *Homo sapiens* | 3-oxobutyrate |
| | | | | | adh | AAA23199.2 | *Clostridium beijerinckii* NRRL B593 | acetone |
| | | | | | adhA | AAC25556 | *Pyrococuus furiosus* | 2-pentanaol, pyruvaldehyde |
| | | | | | ldh | YP_725182.1 | *Ralstonia eutropha* | lactate, 2-oxobutyrate, 2-oxopentaonotae, 2-oxoglutarate |
| | | | | | adh | P14941.1 | *Thermoanaerobacter brockii* HTD4 | acetone |
| I | 4.3.1.a | 2-amino-4-oxo-pentanoate | acetylacrylate | 2-amino-4-oxopentanoate ammonia lyase | aspA | NP_418562 | *Escherichia coli* K12 subsp. MG1655 | L-aspartate |
| | | | | | aspA | P44324.1 | *Haemophilus influenzae* | L-aspartate |
| | | | | | aspA | P07346.1 | *Pseudomonas fluorescens* | L-aspartate |
| | | | | | ansB | P26899.1 | *Bacillus subtilus* | L-aspartate |
| | | | | | aspA | P33109.1 | *Serratia marcescens* | L-aspartate |
| J | 4.1.1.a | acetylacrylate | butenone | acetylacrylate decarboxylase | xylII | YP_709328.1 | *Pseudomonas putida* | 4-oxalocrotonate |
| | | | | | xylIII | YP_709353.1 | *Pseudomonas putida* | 4-oxalocrotonate |
| | | | | | dmpH | CAA43228.1 | *Pseudomonas* sp. CF600 | 4-oxalocrotonate |
| | | | | | dmpE | CAA43225.1 | *Pseudomonas* sp. CF600 | 4-oxalocrotonate |
| | | | | | pdc | U63827 | *Lactobacillus plantarum* | cinnamate and derivatives |
| | | | | | pad | AB330293 | *Klebsiella oxytoca* | cinnamate and derivatives |
| K | 2.6.1.a | 4-aminobutan-2-one | 3-oxobutanal | 4-aminobutan-2-one aminotransferase or oxidoreductase (deaminating) | SkyPYD4 | ABF58893 | *Saccharomyces kluyveri* | beta-alanine |
| | | | | | gabT | P22256 | *Escherichia coli* | 4-aminobutyrate |
| | | | | | Abat | P50554 | *Rattus norvegicus* | 3-amino-2-methylpropionate |
| | | | | | UGA1 | NP_011533 | *Saccharomyces cerevisae* | 4-aminobutyrate |
| | | | | | kdd | AAL93966.1 | *Fusobacterium nucleatum* | 3,5-diaminohexanoate |
| | | | | | lysDH | BAB39707 | *Geobacillus stearothermophilus* | L-lysine |
| L | 1.1.1.a | 2-amino-4-oxo-pentanoate | 2-amino-4-hydroxy-pentanoate | 2-amino-4-oxopentanoate dehydrogenase | thrA | AAC73113 | *Escherichia coli* | aspartate semialdehyde |
| | | | | | hom6 | CAA89671 | *Saccharomyces cerevisae* | aspartate semialdehyde |
| | | | | | hom2 | CAD63186 | *Lactobacillus plantarum* | aspartate semialdehyde |
| | | | | | akthr2 | O81852 | *Arabidopsis thaliana* | aspartate semialdehyde |
| | | | | | hom1 | CAD64819 | *Lactobacillus plantarum* | aspartate semialdehyde |
| M | 2.6.1.a | 2-amino-4-hydroxy-pentanoate | 2-oxo-4-hydroxy-pentanoate | 2-amino-4-hydroxy-pentanoate aminotransferase or oxidoreductase (deaminating) | aspC | NP_415448.1 | *Escherichia coli* | L-aspartate |

TABLE 36-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| | | | | | avtA | YP_026231.1 | *Escherichia coli* | L-alanine, L-valine |
| | | | | | AAT2 | P23542.3 | *Saccharomyces cerevisae* | L-aspartate |
| | | | | | dat | P19938 | *Bacillus* sp. YM-1 | D-alanine, D-2-aminobutanoate, D-aspartate |
| | | | | | dat | O07597 | *Bacillus subtilis* | D-alanine, D-2-aminobutanoate, D-aspartate |
| | | | | | ldh | P0A393 | *Bacillus cereus* | L-leucine, L-valine, 2-aminobutanoate, L-isoleucine |
| | | | | | nadX | NP_229443.1 | *Thermotoga maritima* | L-aspartate |
| N | 4.1.1.a | 2-oxo-4-hydroxy-pentanoate | 3-hydroxybutanal | 2-oxo-4-hydroxy-pentanoate | pdc | P06672.1 | *Zymomonas mobilus* | 2-ketobutyrate |
| | | | | | pdc1 | P06169 | *Saccharomyces cerevisae* | 2-ketobutyrate, 3-hydroxypyruvate |
| | | | | | mdlC | P20906.2 | *Pseudomonas putdia* | 2-ketobutyrate |
| | | | | | kgd | O50463.4 | *Mycobacterium tuberculosis* | alpha-ketoglutarate |
| O | 1.1.1.a | 3-oxobu-tyraldehyde | 3-hydroxybu-tyraldehyde | 3-oxobutyraldehyde reductase (ketone reducing) | bdh | AAA58352.1 | *Homo sapiens* | 3-oxobutyrate |
| | | | | | adh | AAA23199.2 | *Clostridium beijerinckii* NRRL B593 | acetone |
| | | | | | adhA | AAC25556 | *Pyrococuus furiosus* | 2-pentanaol, pyruvaldehyde |
| | | | | | ldh | YP_725182.1 | *Ralstonia eutropha* | lactate, 2-oxobutyrate, 2-oxopentaonotae, 2-oxoglutarate |
| | | | | | adh | P14941.1 | *Thermoanaerobacter brockii* HTD4 | acetone |
| P | 1.1.1.a | 3-hydroxybu-tyraldehyde | 1,3-butanediol | 3-hydroxybu-tyraldehyde reductase | alrA | BAB12273.1 | *Acinetobacter* sp. Strain M-1 | C2-C14 aldehydes |
| | | | | | ADH2 | NP_014032.1 | *Saccharymyces cerevisiae* | propionaldehyde, isobutyraldehyde, butyraldehyde, 2-methylbutyraldehyde, 3-methylbutyraldehyde, 2-phenylacetaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |
| | | | | | ADHI | AAR91477.1 | *Geobacillus thermoglucosidasius* M10EXG | ethanol, 1-butanol, 1-pentanol, 1-heptanol, 1-hexanol, 1-octanol, 2-propanol |

TABLE 36-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| | | | | | mmsb | P28811.1 | *Pseudomonas aeruginosa* | 3-hydroxybutyraldehyde, malonic semialdehyde, methylmalonate semialdehyde |
| | | | | | P84067 | P84067 | *Thermus thermophilus* | methylmalonate semialdehyde |

TABLE 37

(Ref: FIG. 2)

| Step | EC class | Desired substrate | Desired product | Enzyme name | Gene name | GenBank ID (if available) | Organism | Known Substrates |
|---|---|---|---|---|---|---|---|---|
| A | 1.2.1.b | acetoacetyl-CoA | 3-oxobutyraldehyde | acetoacetyl-CoA reductase (aldehdye forming) | Ald | AAT66436 | *Clostridium beijerinckii* | butyryl-CoA |
| | | | | | sucD | NP_904963.1 | *Porphyromonas gingivalis* | succinyl-CoA |
| | | | | | bphG | BAA03892.1 | *Pseudomonas* sp | acetaldehyde, propionaldehyde, butyraldehyde, isobutyraldehyde and formaldehyde |
| | | | | | Msed_0709 | YP_001190808.1 | *Metallosphaera sedula* | malonyl-CoA |
| | | | | | mcr | NP_378167 | *Sulfolobus tokodaii* | malonyl-CoA, methylmalonyl-CoA |
| B | 1.1.1.a | 3-oxobutyraldehyde | 3-hydroxybutyraldehyde | 3-oxobutyraldehyde reductase (ketone-reducing) | bdh | AAA58352.1 | *Homo sapiens* | 3-oxobutyrate |
| | | | | | adh | AAA23199.2 | *Clostridium beijerinckii* NRRL B593 | acetone |
| | | | | | adhA | AAC25556 | *Pyrococcus furiosus* | 2-pentanaol, pyruvaldehyde |
| | | | | | ldh | YP_725182.1 | *Ralstonia eutropha* | lactate, 2-oxobutyrate, 2-oxopentaonotae, 2-oxoglutarate |
| | | | | | adh | P14941.1 | *Thermoanaerobacter brockii* HTD4 | acetone |
| C | 1.1.1.a | 3-hydroxybutyraldehyde | 1,3-butanediol | 3-hydroxybutyraldehyde reductase | alrA | BAB12273.1 | *Acinetobacter* sp. Strain M-1 | C2-C14 aldehydes |
| | | | | | ADH2 | NP_014032.1 | *Saccharymyces cerevisiae* | propionaldehyde, isobutyraldehyde, butyraldehyde, 2-methylbutyraldehyde, 3-methylbutyraldehyde, 2-phenylacetaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |

TABLE 37-continued (Ref: FIG. 2)

| Step | EC class | Desired substrate | Desired product | Enzyme name | Gene name | GenBank ID (if available) | Organism | Known Substrates |
|---|---|---|---|---|---|---|---|---|
| | | | | | 4hbd | YP_726053.1 | *Ralstonia eutropha* H16 | succinate semialdehyde |
| | | | | | ADHI | AAR91477.1 | *Geobacillus thermoglucosidasius* M10EXG | ethanol, 1-butanol, 1-pentanol, 1-heptanol, 1-hexanol, 1-octanol, 2-propanol |
| | | | | | mmsb | P28811.1 | *Pseudomonas aeruginosa* | 3-hydroxybutyr-aldehyde, malonic semialdehyde, methylmalonate semialdehyde |
| | | | | | P84067 | P84067 | *Thermus thermophilus* | methylmalonate semialdehyde |
| D | 1.1.1.c | acetoacetyl-CoA | 4-hydroxy, 2-butanone | acetoacetyl-CoA reductase (alcohol-forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| E | 1.1.1.a | 3-oxobutyr-aldehyde | 4-hydroxy, 2-butanone | 3-oxobutyraldehdye reductase (aldehyde reducing) | alrA | BAB12273.1 | *Acinetobacter* sp. Strain M-1 | C2-C14 aldehydes |
| | | | | | ADH2 | NP_014032.1 | *Saccharymyces cerevisiae* | propionaldehyde, isobutyraldehyde, butyraldehyde, 2-methylbutyraldehyde, 3-methylbutyraldehyde, 2-phenylacetaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |
| | | | | | ADHI | AAR91477.1 | *Geobacillus thermoglucosidasius* M10EXG | ethanol, 1-butanol, 1-pentanol, 1-heptanol, 1-hexanol, 1-octanol, 2-propanol |
| | | | | | mmsb | P28811.1 | *Pseudomonas aeruginosa* | 3-hydroxybutyraldehyde, malonic semialdehyde, methylmalonate semialdehyde |
| | | | | | P84067 | P84067 | *Thermus thermophilus* | methylmalonate semialdehyde |
| F | 1.1.1.a | 4-hydroxy, 2-butanone | 1,3-butanediol | 4-hydroxy, 2-butanone reductase | bdh | AAA58352.1 | *Homo sapiens* | 3-oxobutyrate |
| | | | | | adh | AAA23199.2 | *Clostridium beijerinckii* NRRL B593 | acetone |
| | | | | | adhA | AAC25556 | *Pyrococuus furiosus* | 2-pentanaol, pyruvaldehyde |
| | | | | | ldh | YP_725182.1 | *Ralstonia eutropha* | lactate, 2-oxobutyrate, 2-oxopentaonotae, 2-oxoglutarate |

TABLE 37-continued (Ref: FIG. 2)

| Step | EC class | Desired substrate | Desired product | Enzyme name | Gene name | GenBank ID (if available) | Organism | Known Substrates |
|---|---|---|---|---|---|---|---|---|
| | | | | | adh | P14941.1 | *Thermoanaerobacter brockii* HTD4 | acetone |
| G | 1.1.1.a | acetoacetyl-CoA | 3-hydroxybutyryl-CoA | acetaocetyl CoA reductase (ketone reducing) | hbd | NP_349314.1 | *Clostridium acetobutylicum* | acetoacetyl-CoA |
| | | | | | hbd | AAM14586.1 | *Clostridium beijerinckii* | acetoacetyl-CoA |
| | | | | | Hbd2 | EDK34807.1 | *Clostridium kluyveri* | acetoacetyl-CoA |
| | | | | | Hbd1 | EDK32512.1 | *Clostridium kluyveri* | acetoacetyl-CoA |
| | | | | | Msed_1423 | YP_001191505 | *Metallosphaera sedula* | 3-hydroxybutyryl-CoA (suspected) |
| | | | | | Msed_0399 | YP_001190500 | *Metallosphaera sedula* | 3-hydroxybutyryl-CoA (suspected) |
| | | | | | Msed_0389 | YP_001190490 | *Metallosphaera sedula* | 3-hydroxybutyryl-CoA (suspected) |
| | | | | | Msed_1993 | YP_001192057 | *Metallosphaera sedula* | 3-hydroxybutyryl-CoA (suspected) |
| | | | | | fadB | P21177.2 | *Escherichia coli* | 3-oxoacyl-CoA |
| | | | | | fadJ | P77399.1 | *Escherichia coli* | 3-oxoacyl-CoA |
| H | 1.2.1.b | 3-hydroxybutyryl-CoA | 3-hydroxybutyraldehyde | 3-hydroxy-butyryl-CoA redcutase (aldehyde forming) | Ald | AAT66436 | *Clostridium beijerinckii* | butyryl-CoA |
| | | | | | sucD | NP_904963.1 | *Porphyromonas gingivalis* | succinyl-CoA |
| | | | | | bphG | BAA03892.1 | *Pseudomonas* sp | acetaldehyde, propionaldehyde, butyraldehyde, isobutyraldehyde and formaldehyde |
| | | | | | Msed_0709 | YP_001190808.1 | *Metallosphaera sedula* | malonyl-CoA |
| | | | | | mcr | NP_378167 | *Sulfolobus tokodaii* | malonyl-CoA, methylmalonyl-CoA |
| I | 1.1.1.c | 3-hydroxybutyryl-CoA | 1,3-butanediol | 3-hydroxy-butyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |

TABLE 38

(Ref: FIG. 3)

| Step | EC class | Desired substrate | Desired product | Enzyme name | Gene name | GenBank ID (if available) | Organism | Known Substrates |
|---|---|---|---|---|---|---|---|---|
| A | 4.2.1.a | 4-hydroxybutyryl-CoA | crotonyl-CoA | 4-hydroxybutyryl-CoA dehydratase | abfD | YP_001396399.1 | *Clostridium kluyveri* DSM 555 | 4-hydroxybutyryl-CoA |
| | | | | | abfD | P55792 | *Clostridium aminobutyricum* | 4-hydroxybutyryl-CoA |
| | | | | | abfD | YP_001928843 | *Porphyromonas gingivalis* ATCC 33277 | 4-hydroxybutyryl-CoA |
| B | 4.2.1.a | crotonyl-CoA | 3-hydroxybutyryl-CoA | crotonase | crt | NP_349318.1 | *Clostridium acetobutylicum* | 3-hydroxybutyryl-CoA |
| | | | | | crt1 | YP_001393856 | *Clostridium kluyveri* DSM 555 | 3-hydroxybutyryl-CoA |

TABLE 38-continued (Ref: FIG. 3)

| Step | EC class | Desired substrate | Desired product | Enzyme name | Gene name | GenBank ID (if available) | Organism | Known Substrates |
|---|---|---|---|---|---|---|---|---|
| | | | | | crt | YP_001929291.1 | *Porphyromonas gingivalis* ATCC 33277 | example based on sequence similarity |
| | | | | | paaA | NP_745427.1 | *Pseudomonas putida* | enoyl-CoA, cis-dihydrodiol derivative of phenylacetyl-CoA |
| | | | | | paaB | NP_745426.1 | *Pseudomonas putida* | enoyl-CoA, cis-dihydrodiol derivative of phenylacetyl-CoA |
| | | | | | phaA | ABF82233.1 | *Pseudomonas fluorescens* | enoyl-CoA, cis-dihydrodiol derivative of phenylacetyl-CoA |
| | | | | | phaB | ABF82234.1 | *Pseudomonas fluorescens* | enoyl-CoA, cis-dihydrodiol derivative of phenylacetyl-CoA |
| | | | | | maoC | NP_415905.1 | *Escherichia coli* | enoyl-CoA, cis-dihydrodiol derivative of phenylacetyl-CoA |
| | | | | | paaF | NP_415911.1 | *Escherichia coli* | enoyl-CoA, cis-dihydrodiol derivative of phenylacetyl-CoA |
| | | | | | paaG | NP_415912.1 | *Escherichia coli* | enoyl-CoA, cis-dihydrodiol derivative of phenylacetyl-CoA |
| C | 1.2.1.b | 3-hydroxybutyryl-CoA | 3-hydroxy-butyraldehyde | 3-hydroxy-butyryl-CoA reductase (aldehyde forming) | Ald | AAT66436 | *Clostridium beijerinckii* | butyryl-CoA |
| | | | | | sucD | NP_904963.1 | *Porphyromonas gingivalis* | succinyl-CoA |
| | | | | | bphG | BAA03892.1 | *Pseudomonas* sp | acetaldehyde, propionaldehyde, butyraldehyde, isobutyraldehyde and formaldehyde |
| | | | | | Msed_0709 | YP_001190808.1 | *Metallosphaera sedula* | malonyl-CoA |
| | | | | | mcr | NP_378167 | *Sulfolobus tokodaii* | malonyl-CoA, methylmalonyl-CoA |
| D | 1.1.1.a | 3-hydroxy-butyraldehyde | 1,3-butanediol | 3-hydroxy-butyraldehyde reductase | alrA | BAB12273.1 | *Acinetobacter* sp. Strain M-1 | C2-C14 aldehydes |
| | | | | | ADH2 | NP_014032.1 | *Saccharymyces cerevisiae* | propionaldehyde, isobutyraldehyde, butyraldehyde, 2-methylbutyr-aldehyde, 3-methylbutyr-aldehyde, 2-phenylacet-aldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |

TABLE 38-continued (Ref: FIG. 3)

| Step | EC class | Desired substrate | Desired product | Enzyme name | Gene name | GenBank ID (if available) | Organism | Known Substrates |
|------|----------|-------------------|-----------------|-------------|-----------|---------------------------|----------|------------------|
|      |          |                   |                 |             | ADHI      | AAR91477.1                | *Geobacillus thermoglucosidasius* M10EXG | ethanol, 1-butanol, 1-pentanol, 1-heptanol, 1-hexanol, 1-octanol, 2-propanol |
|      |          |                   |                 |             | mmsb      | P28811.1                  | *Pseudomonas aeruginosa* | 3-hydroxy-butyraldehyde, malonic semialdehyde, methylmalonate semialdehyde |
|      |          |                   |                 |             | P84067    | P84067                    | *Thermus thermophilus* | methylmalonate semialdehyde |
| E    | 1.1.1.c  | 3-hydroxybutyryl-CoA | 1,3-butanediol | 3-hydroxy-butyryl-CoA reductase (alcohol forming) | adhE2 | AAK09379.1 | *Clostridium acetobutylicum* | butanoyl-CoA |
|      |          |                   |                 |             | mcr       | AAS20429.1                | *Chloroflexus aurantiacus* | malonyl-CoA |
|      |          |                   |                 |             | FAR       | AAD38039.1                | *Simmondsia chinensis* | long chain acyl-CoA |

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

Msed_1220, fadA, fadB, fadI, fadJ, and fadR, wherein each of said genes encode an enzyme capable of catalyzing hydration of crotonyl-CoA to form 3-hydroxybutyryl-CoA.

3. The non-naturally occurring microbial organism of claim 1, further comprising at least one exogenous nucleic acid encoding:

What is claimed is:

1. A non-naturally occurring microbial organism comprising a set of enzymes that convert 4-hydroxbutyryl-CoA to 1,3-butanediol (1,3-BDO),
   wherein said microbial organism comprises at least one heterologous nucleic acid encoding a crotonase that converts crotonoyl-CoA to 3-Hydroxybutyryl-CoA, and
   wherein the crotonase is expressed in a sufficient amount to produce 1,3-BDO.

2. The non-naturally occurring microbial organism of claim 1, wherein said crotonase is encoded by one or more genes selected from the group consisting of crt, crt1, ech, paaA, paaB, phaA, phaB, maoC, paaF, paaG, abfD, (a) a 3-hydroxybutyryl-CoA reductase (aldehyde forming) that converts 3-hydroxybutyryl-CoA to 3-hydroxy-butyraldehyde; or (b) a 3-hydroxybutyraldehyde reductase that converts 3-hydroxybutyraldehyde to 1,3-butanediol.

4. The non-naturally occurring microbial organism of claim 3 comprising at least one exogenous nucleic acid encoding the 3-hydroxybutyryl-CoA reductase (aldehyde forming) that converts 3-hydroxybutyryl-CoA to 3-hydroxy-butyraldehyde and at least one exogenous nucleic acid encoding the 3-hydroxybutyraldehyde reductase that converts 3-hydroxybutyraldehyde to 1,3-butanediol.

5. The non-naturally occurring microbial organism of claim 3, wherein said 3-hydroxybutyraldehdye reductase is encoded by one or more genes selected from the group consisting of alrA, ADH2, yqhD, bdh I, bdh II, adhA, 4hbd, adhI, P84067, mmsb, dhat, and 3hidh.

6. The non-naturally occurring microbial organism of claim 3, wherein said 3-hydroxybutyryl-CoA reductase (aldehyde forming) is encoded by one or more genes selected from the group consisting of acr 1, sucD, bphG, bld, adhE, Msed_0709, mcr, asd-2, Sad 2370, Ald, and eutE.

7. The non-naturally occurring microbial organism of claim 1, further comprising at least one exogenous nucleic acid encoding a 3-hydroxybutyryl-CoA reductase (alcohol forming) that converts 3-hydroxybutyryl-CoA to 1,3-butanediol.

8. The non-naturally occurring microbial organism of claim 7, wherein said 3-hydroxybutyryl-CoA reductase (alcohol forming) is encoded by one or more genes selected from the group consisting of adhE, adhE2, mcr, Rcas_2929, NAP1_02720, MGP2080_00535, and FAR.

9. The non-naturally occurring microbial organism of claim 1 further comprising at least one exogenous nucleic acid encoding a 4-hydroxybutyryl-CoA dehydratase that converts 4-hydroxybutyryl-CoA to crotonyl-CoA.

10. The non-naturally occurring microbial organism of claim 9, wherein said 4-hydroxybutyryl-CoA dehydratase is encoded by one or more genes selected from the group consisting of fumA, fumB, fumC, fumH, fum1, MmcB, MmcC, hmd, BACCAP_02294, ANACOL_02527, NtherDRAFT_2368, dmdA, dmdB, crt, crt1, ech paaA, paaB, phaA, phaB, maoC, paaF, paaG, abfD, Msed_1220, fadA, fadB, fadI, fadJ, and fadR.

11. The non-naturally occurring microbial organism of claim 1, wherein said non-naturally occurring microbial organism is in a substantially anaerobic culture medium.

12. The non-naturally occurring microbial organism of claim 1, wherein said microbial organism is a bacterium.

13. The non-naturally occurring microbial organism of claim 12, wherein said bacteria is *E. coli*.

14. A culture medium comprising the non-naturally occurring microbial organism of claim 1.

15. The culture medium of claim 14 further comprising 1,3-BDO.

16. A method for producing 1,3-BDO, comprising culturing the non-naturally occurring microbial of claim 1 under conditions and for a sufficient period of time to produce 1,3-BDO.

17. The method of claim 16 further comprising separating 1,3-BDO from other components in the culture.

18. The method of claim 17, wherein the separating comprises extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, absorption chromatography, or ultrafiltration.

19. The method of claim 17, wherein the separating comprises distillation.

20. The non-naturally occurring microbial organism of claim 1, wherein the microbial organism comprises three exogenous nucleic acids, each encoding an enzyme of the set.

21. The non-naturally occurring microbial organism of claim 1, wherein at least one exogenous nucleic acid is a heterologous nucleic acid.

22. The non-naturally occurring microbial organism of claim 1, wherein the microbial organism comprises four exogenous nucleic acids, each encoding an enzyme of the set.

* * * * *

```
SEQUENCE LISTING

<160> NUMBER OF SEQ ID NOS: 1

<210> SEQ ID NO 1
<211> LENGTH: 20
<212> TYPE: PRT
<213> ORGANISM: Euglena gracilis

<400> SEQUENCE: 1

Met Thr Tyr Lys Ala Pro Val Lys Asp Val Lys Phe Leu Leu Asp Lys
1               5                   10                  15

Val Phe Lys Val
            20
```